US008108149B2

(12) United States Patent
Clark et al.

(10) Patent No.: US 8,108,149 B2
(45) Date of Patent: Jan. 31, 2012

(54) METHOD AND DEVICE FOR DIAGNOSING AND TREATING INSULIN-LIKE GROWTH FACTOR DEFICIENCY DISORDERS

(75) Inventors: Ross Graham Clark, Devonport, Auckland (NZ); Gillian Clark, legal representative, North Shore (NZ); George M. Bright, San Mateo, CA (US); Sam Liao, Costa Mesa, CA (US)

(73) Assignee: Tercica, Inc., Brisbane, CA (US)

(*) Notice: Subject to any disclaimer, the term of this patent is extended or adjusted under 35 U.S.C. 154(b) by 1423 days.

(21) Appl. No.: 11/215,746

(22) Filed: Aug. 29, 2005

(65) Prior Publication Data

US 2006/0064249 A1    Mar. 23, 2006

Related U.S. Application Data

(60) Provisional application No. 60/605,850, filed on Aug. 30, 2004.

(51) Int. Cl.
*G01N 33/48* (2006.01)
*G06G 7/48* (2006.01)
*A61K 38/18* (2006.01)

(52) U.S. Cl. .................. 702/19; 703/11; 514/7.6
(58) Field of Classification Search .............. None
See application file for complete search history.

(56) References Cited

U.S. PATENT DOCUMENTS

| | | |
|---|---|---|
| 4,988,675 A | 1/1991 | Froesch et al. |
| 5,068,224 A | 11/1991 | Fryklund et al. |
| 5,077,276 A * | 12/1991 | Ballard et al. .................. 514/12 |
| 5,093,317 A | 3/1992 | Lewis et al. |
| 5,106,832 A | 4/1992 | Froesch et al. |
| 5,126,324 A | 6/1992 | Clark et al. |
| 5,187,151 A | 2/1993 | Clark et al. |
| 5,202,119 A | 4/1993 | Clark et al. |
| 5,273,961 A | 12/1993 | Clark |
| 5,374,620 A | 12/1994 | Clark et al. |
| 5,466,670 A | 11/1995 | Dunger et al. |

(Continued)

FOREIGN PATENT DOCUMENTS

WO    WO 93/23071    11/1993

(Continued)

OTHER PUBLICATIONS

Ito et al. (The Journal of Clinical Investigation, 1971, 50, 1621-1627).*

(Continued)

*Primary Examiner* — Marjorie Moran
*Assistant Examiner* — Larry D Riggs, II
(74) *Attorney, Agent, or Firm* — Paula A. Borden, Ph. D.; Bozicevic Field & Francis LLP

(57) ABSTRACT

The present invention provides standard deviation score (SDS) calculators, which SDS calculators are useful for transforming insulin-like growth factor-1 (IGF-1) concentrations to IGF-1 standard deviation scores. In one embodiment, IGF-1 blood levels are calculated so as to take into account IGFBP-3 blood levels (and, optionally, IGF-2 blood levels) to provide an IGF-1 production rate, which can be used to calculate an IGF-1 production rate SDS. The IGF-1 SDS and IGF-1 production rate SDS are particularly useful in assessing the stimulated rate of IGF-1 production in response to, for example, growth hormone therapy.

9 Claims, 20 Drawing Sheets

U.S. PATENT DOCUMENTS

| | | | |
|---|---|---|---|
| 5,569,648 A | | 10/1996 | Lewis et al. |
| 5,681,814 A | | 10/1997 | Clark et al. |
| 5,824,642 A | * | 10/1998 | Attie et al. .................... 514/12 |

FOREIGN PATENT DOCUMENTS

| | | |
|---|---|---|
| WO | WO 94/06461 | 3/1994 |

OTHER PUBLICATIONS

Mehta et al. (Disease Markers, 2003, 2004, 1-10).*

Mizuno et al. (Pharmaceutical Research, 2001, 18,(8), 1203-1209).*

Rajaram et al. (Endocrine Reviews, 1997, 18(6), 801-831).*

Blum, et al. Improvement of diagnostic criteria in growth hormone insensitivity syndrome: solutions and pitfalls. Acta Paediatr Suppl, 1994, 399, pp. 117-124.

Selva, et al. Reproducibility in patterns of IGF generation with special references to idiopathic short stature. Horm Res, 2003, vol. 60, 237-246.

Brabant et al. Serum insulin-like growth factor I reference values for an automated chemiluminescence immunoassay system: results from a multicenter study. (2003) *Hormone Res*. 60:53-60.

Buckway et al. The IGF-I generation test revisited: a marker of GH sensitivity. (2001) *J Clin Endocrinol Metab*. 86(11):5176-83.

Chawla, Structural variants of human growth hormone: biochemical, genetic, and clinical aspects. 1983, Annu. Rev. Med. 34: 519.

Clemmons DR et al., Factors controlling blood concentration of somatomedin C.1984, Clin Endocrinol Metab 13:113.

Clemmons DR et al., Evaluation of acromegaly by radioimmunoassay of somatomedin-C.1979, N Engl J Med 301:1138.

Clemmons DR et al., Somatomedin-C/insulin-like growth factor I in acromegaly. 1986, Clin Endocrinol Metab 15:629.

Edwards et al., A newly defined property of somatotropin: priming of macrophages for production of superoxide anion. 1988, Science 239: 769.

Gharib et al. American Association of Clinical Endocrinologists medical guidelines for clinical practice for growth hormone use in adults and children—2003 update. (2003) Endocr. Pract. 9:64-76.

Hughes and Friesen, The nature and regulation of the receptors for pituitary growth hormone. Annu. Rev. Physiol. 47: 469.

Isaksson et al., Mode of action of pituitary growth hormone on target cells. 1985, Annu. Rev. Physiol. 47: 483.

Juul et al. European audit of current practice in diagnosis and treatment of childhood growth hormone deficiency. (2002) *Hormone Res*. 58:233-241.

Jorge et al., Poor reproducibility of IGF-I and IGF binding protein-3 generation test in children with short stature and normal coding region of the GH receptor gene.2002, J Clin Endocrinol Metab 87:469.

Jorgensen et al., Short-term tools to measure responsiveness to growth hormone replacement. 2001, Horm Res 55 Suppl 2:40.

Kuczmarski et al. 2000 CDC Growth Charts for the United States: methods and development. (2002) *Vital Health Stat*. 246:1-190.

Kamp et al., 2002, Biochemical markers of growth hormone (GH) sensitivity in children with idiopathic short stature: individual capacity of IGF-I generation after high-dose GH treatment determines the growth response to GH.Clin Endocrinol (Oxf) 57:315-25.

Lupu et al., 2001, Roles of growth hormone and insulin-like growth factor 1 in mouse postnatal growth.Dev Biol 229: 141-62.

Löfqvist et al. Reference values for IGF-I throughout childhood and adolescence: a model that accounts simultaneously for the effect of gender, age, and puberty. (2001) *J Clin Endocrinol Metab*. 86(12):5870-6.

Mauras et al. Pharmacokinetics of insulin-like growth factor I in hypopituitarism: correlation with binding proteins. (1999) *Am. J. Physiol*. 277:E579.

Mizuno et al. Kinetic analysis of the disposition of insulin-like growth factor 1 in healthy volunteers. (2001) Pharm. Res. 18:1203.

Ross et al. The role of insulin, growth hormone and IGF-I as anabolic agents in the critically ill. (1993) *Intensive Care Med*. 19 Suppl. 2: S54-57.

Rosenfeld and HWA. Toward a molecular basis for idiopathic short stature. (2004) *J. Clin. Endocrinol. Metab*. 89:1066-1067.

Rosenfeld et al., Is growth hormone deficiency a viable diagnosis?1997, J Clin Endocrinol Metab 82: 349.

Rosenfeld et al., Diagnostic controversy: the diagnosis of childhood growth hormone deficiency revisited.1995, J Clin Endocrinol Metab 80:1532.

Rudman et al., The relation between growth velocity and serum somatomedin C concentration.1981, J Clin Endocrinol Metab 52:622.

Saggese et al., Diagnosis and treatment of growth hormone deficiency in children and towards a consensus. Ten years after the Availability of Recombinant Human Growth Hormone Workshop held in Pisa, Italy, Mar. 27-28, 1998. Horm Res 50:320.

Salmon WD Jr. et al., A hormonally controlled serum factor which stimulates sulfate incorporation by cartilage in vitro.1957, J Lab Clin Med, 49:825.

Thorner and Vance. Growth hormone, 1988.Growth hormone, 1988. J. Clin. Invest. 82: 745.

Tillmann et al., Biochemical tests in the diagnosis of childhood growth hormone deficiency. 1997, J Clin Endocrinol Metab 82: 531-5.

Van Wyk JJ. The Somatomedins: biological actions and physiological control mechanisms in Hormonal Proteins and Peptides, ed CH Li, 12:81-175, Orlando, FL:Academic Press.

Vance and Mauras, Growth hormone therapy in adults and children. 1999, N Engl J Med 341:1206.

Woods et al., Extensive Personal Experience. 1997, J Clin Endocrinol Metab 82: 3529.

Wilson et al. Update of guidelines for the use of growth hormone in children: the Lawson Wilkins Pediatric Endocrinology Society Drug and Therapeutics Committee. (2003) *J. Pediatr*. 143:415-421.

\* cited by examiner

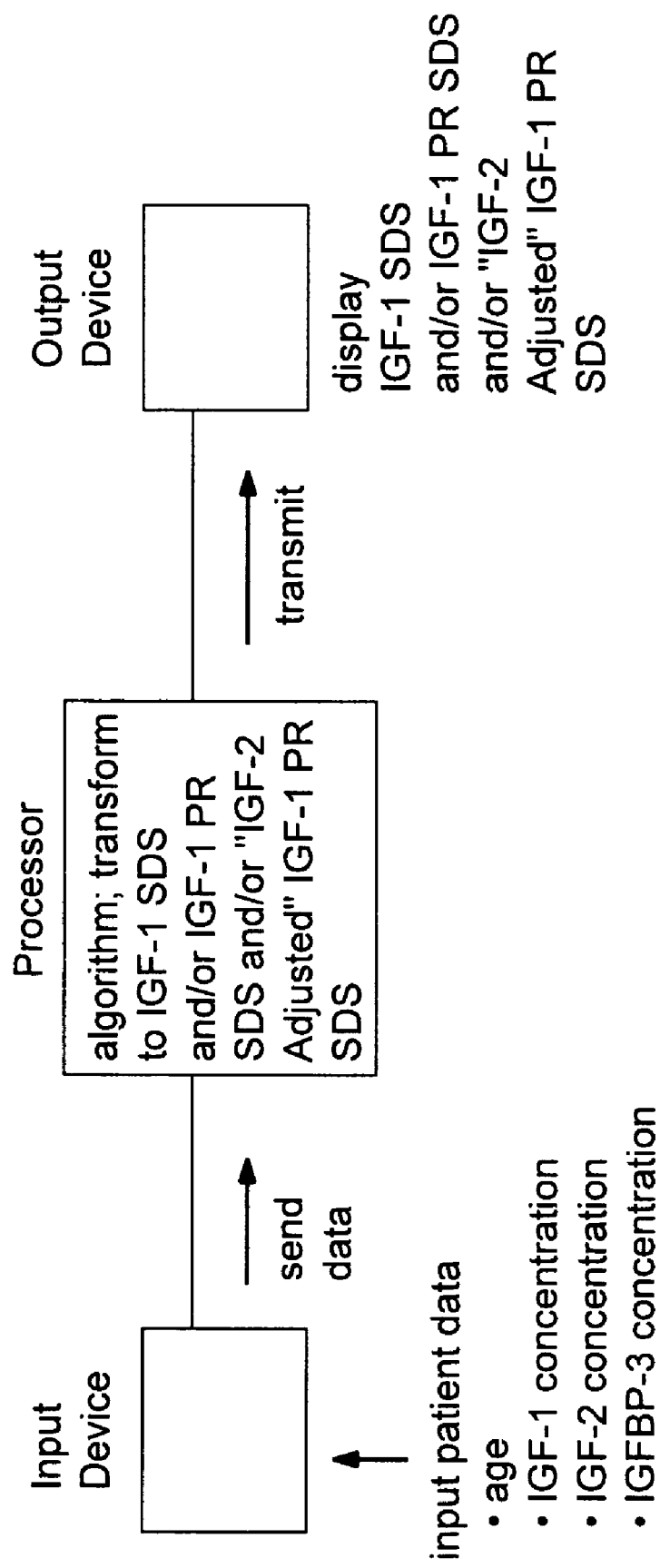

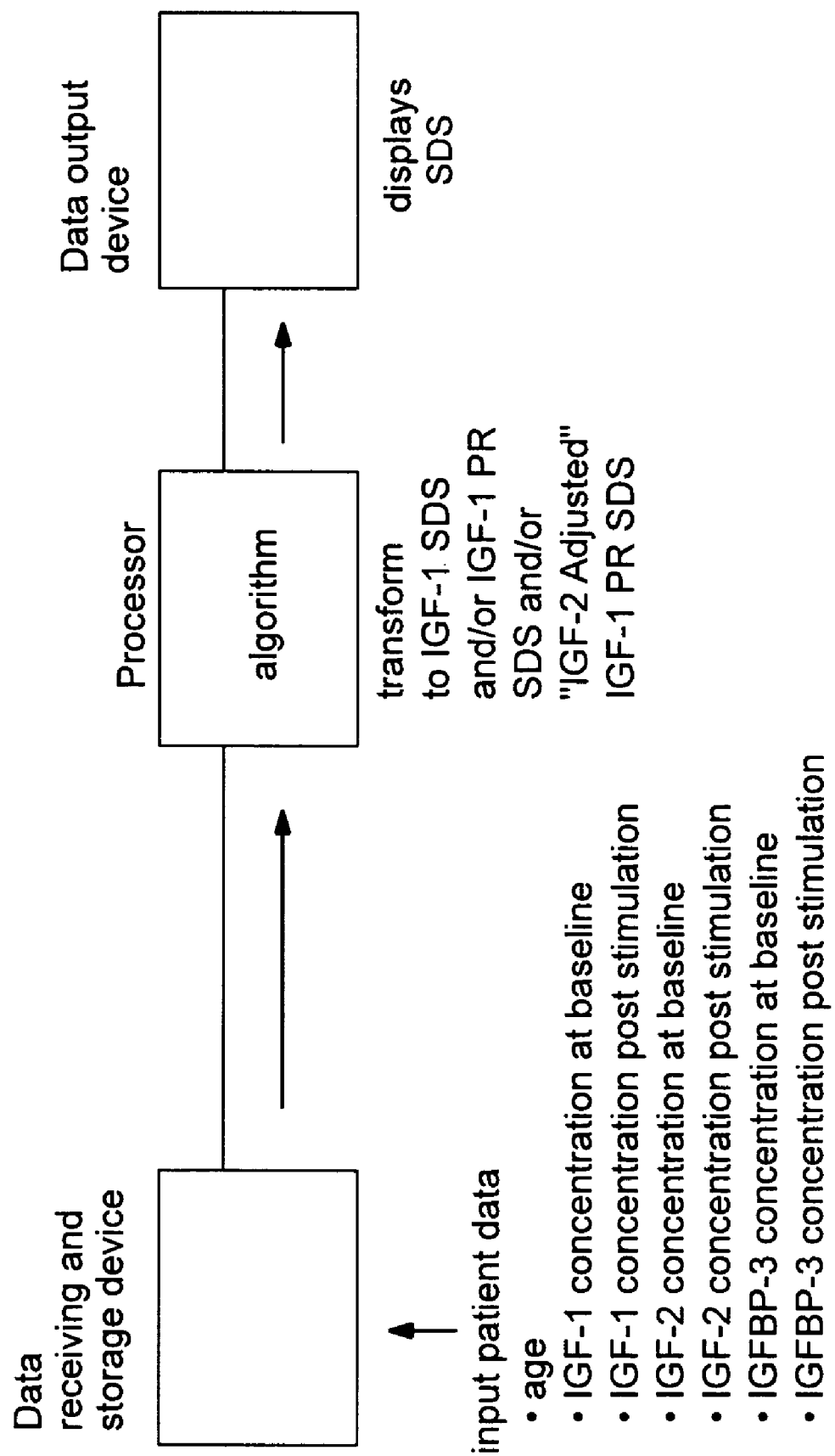

METHOD AND DEVICE FOR DIAGNOSING AND TREATING INSULIN-LIKE GROWTH FACTOR DEFICIENCY DISORDERS

CROSS-REFERENCE

This application claims the benefit of U.S. Provisional Application No. 60/605,850, filed Aug. 30, 2004, which application is incorporated herein by reference in its entirety.

APPENDIX A-APPENDIX H

The present application incorporates by reference Appendix A-Appendix H contained on two compact discs filed concurrently herewith, which compact discs are labeled "Copy 1—Appendix A-Appendix H" and "Copy 2—Appendix A-Appendix H". The details of Appendix A-Appendix H are further described later in this disclosure. These compact discs were created on 29 Aug. 2005. Appendix A is 10 kilobytes in size, Appendix B is 844 kilobytes in size, Appendix C is 932 kilobytes in size, Appendix D is 18 kilobytes in size, Appendix E is 18 kilobytes in size, Appendix F is 12 kilobytes in size, Appendix G is 11 kilobytes in size, Appendix H is 4 kilobytes in size.

FIELD OF THE INVENTION

The present invention is in the field of use of insulin-like growth factor-1 to treat disorders of IGF-1 deficiency and IGF-1 production including those of short stature and metabolic disorders.

BACKGROUND OF THE INVENTION

Human insulin-like growth factor-1 (IGF-1) is a 7649-dalton polypeptide belonging to a family of somatomedins with insulin-like metabolic actions and the differentiative, mitogenic, and anti-apopototic biological activities that modulate the actions of growth hormone (GH). IGF-1 mediates the effects of GH on post-natal growth in humans. Like GH, IGF-1 is a potent anabolic protein. IGF-1 has hypoglycemic effects similar to those of insulin, and also promotes positive nitrogen balance. It is estimated that approximately 20,000 children in the United States have growth failure due to growth hormone deficiency and a large number have IGF-1 deficiency in the presence of normal GH secretion. In addition, a larger number of adults also have these hormone deficient states.

IGF-1 deficiency (IGFD) can be due to a resistance to GH action or as a result of GH deficiency (GHD). IGFD that is due to resistance to GH action is termed primary IGFD, while IGFD resulting from GHD is termed secondary IGFD. Currently, production of GH following administration of a GH secretagogue or of an agent that stimulates GH secretion is used as an indication of GHD. There is currently no single test that can distinguish between individuals having primary IGFD and secondary IGFD, or assign an appropriate therapy such as GH, IGF-1 or combination therapy of GH and IGF-1. As a result, many individuals may receive inappropriate or ineffective treatment.

Accordingly, there is a need in the art to improve the diagnosis of IGF-1 deficiency, and particularly a need for improved diagnostic methods that allow discrimination between primary IGFD and secondary IGFD, and to discover how responsive patients are to therapy with GH. Such diagnostics facilitate selection of therapies appropriate for the disease or disorder. Currently, IGF-1 deficiency is established on the basis of measuring blood IGF-1 levels and comparing them to the blood IGF-1 levels obtained from a large number of individuals to establish an IGF-1 standard deviation score (IGF-1 SDS).

The present invention addresses this need by providing, for example, improved methods of establishing that a patient is IGF-1 deficient not only based on their blood concentration of IGF-1 but also on their ability to produce IGF-1 both before and after their blood GH levels are increased. The invention also provides advantages related to such improved diagnostics.

Literature

U.S. Pat. Nos. 5,273,961; 5,466,670; 5,126,324; 5,187,151; 5,202,119; 5,374,620; 5,106,832; 4,988,675; 5,106,832; 5,068,224; 5,093,317; and 5,569,648; Ross et al. (1993) *Intensive Care Med.* 19 Suppl. 2: S54-57; Buckway et al. (2001) *J Clin Endocrinol Metab.* 86(11):5176-83; Kuczmarski et al. (2002) *Vital Health Stat.* 246:1-190; Brabant et al. (2003) *Hormone Res.* 60:53-60; Mauras et al. (1999) *Am. J. Physiol.* 277:E579-E584; Mizuno et al. (2001) *Pharm. Res.* 18:1203-1209; Wilson et al. (2003) *J. Pediatr.* 143:415-421; Gharib et al. (2003) *Endocr. Pract.* 9:64-76; Juul et al. (2002) *Hormone Res.* 58:233-241; Rosenfeld and Hwa (2004) *J. Clin. Endocrinol. Metab.* 89:1066-1067; Löfqvist et al. (2001) *J Clin Endocrinol Metab.* 86(12):5870-6.

Chawla, 1983, Annu. Rev. Med. 34: 519; Edwards et al., 1988, Science 239: 769; Isaksson et al., 1985, Annu. Rev. Physiol. 47: 483; Thorner and Vance, 1988, J. Clin. Invest. 82: 745; Hughes and Friesen, 1985, Annu. Rev. Physiol. 47: 469; Van Wyk J J. The Somatomedins: biological actions and physiological control mechanisms in Hormonal Proteins and Peptides, ed C H Li, 12:81-175, Orlando, Fla.: Academic Press; Salmon W D Jr. et al., 1957, J Lab Clin Med, 49:825-36; Clemmons D R et al., 1984, Clin Endocrinol Metab 13:113-43; Clemmons D R et al., 1979, N Engl J Med 301: 1138-42; Clemmons D R et al., 1986, Clin Endocrinol Metab 15:629-51; (Lupu et al., 2001, Dev Biol 229: 141-62; Vance and Mauras, 1999, N Engl J Med 341:1206-16; Rosenfeld et al., 1997, J Clin Endocrinol Metab 82: 349-351; (Tillmann et al., 1997, J Clin Endocrinol Metab 82: 531-5; Rosenfeld et al., 1995, J Clin Endocrinol Metab 80:1532-40; Saggese et al., 1998, Horm Res 50:320-40; Rudman et al., 1981, J Clin Endocrinol Metab 52:622-7; Kamp et al., 2002, Clin Endocrinol (Oxf) 57:315-25; Jorge et al., 2002, J Clin Endocrinol Metab 87:469-72; Jorgensen et al., 2001, Horm Res 55 Suppl 2:40-3; Woods et al., 1997, J Clin Endocrinol Metab 82: 3529-35.

SUMMARY OF THE INVENTION

The present invention provides standard deviation score (SDS) calculators, which SDS calculators are useful for transforming insulin-like growth factor-1 (IGF-1) concentrations or IGF-1 production rates to IGF-1 standard deviation scores. In one embodiment, IGF-1 production rates are calculated by taking into account IGFBP-3 blood levels (and, optionally, IGF-2 blood levels) to provide an IGF-1 production rate, which can be used to calculate an IGF-1 production rate SDS (IGF-1 PR SDS). The IGFBP-3 adjusted IGF-1 levels are particularly useful in assessing the rate of IGF-1 production in response to, for example, growth hormone therapy.

Accordingly, the present invention provides standard deviation score (SDS) calculators, which SDS calculators are useful for transforming insulin-like growth factor-1 (IGF-1) concentrations to IGF-1 standard deviation scores. In one embodiment, the IGF-1 PR SDS can be calculated by taking into account IGFBP-3 levels, so as to provide an IGF-1 PR SDS. The invention further provides computer program products for carrying out such transformations, as well as systems and devices for transforming an IGF-1 concentration to an IGF-1 SDS or to an IGF-1 PR SDS. The present invention further provides methods of diagnosing primary IGFD and secondary IGFD and patients in need of combination therapy with GH and IGF-1 as well as kits, devices, and systems for carrying out a subject diagnostic method. The present invention further provides methods of treating IGFD, the methods generally involving determining an IGF-1 SDS and/or an IGF-1 PR SDS; and, based on the IGF-1 SDS and/or IGF-1 PR SDS, administering an effective amount of IGF-1, an agent that increases a blood level of growth hormone (GH), or an effective combination of IGF-1 and an agent that increases a blood level of GH.

In addition, the invention also provides methods and systems for determining the amount of IGF-1 produced by a patient, which method takes into account IGFBP-3 blood levels at both pre-treatment and post-treatment. This is generally accomplished by measuring both the blood IGF-1 concentration and the blood IGFBP-3 concentration at baseline, and calculating an IGF-1 production rate by taking blood IGFBP-3 concentration into account. Then following administration of an agent to increase blood GH levels, the blood IGF-1 concentration and the blood IGFBP-3 concentrations are again measured, the IGF-production rate again calculated taking IGFBP-3 concentration into account. The stimulated rate of IGF-1 production is calculated by subtracting the IGF-1 production rate at baseline from the IGF-1 production rate after treatment. In one embodiment, the IGF-1 production rate at each of baseline and post-therapy are each used in the SDS calculator above to provide a baseline IGF-1 PR SDS and a post-therapy IGF-1 PR SDS, and a change in the IGF-1 PR SDS can be calculated. In addition since IGF-2 also binds to IGFBP-3, the invention also contemplates adjusting the IGFBP-3 concentration prior to calculation of an IGF-1 production rate, which can then be used to calculate an "IGF-2 Adjusted" IGF-1 PR SDS.

The stimulated rate of IGF-1 production, adjusted for IGFBP-3 and, optionally, adjusted for IGF-2, can be used to establish if IGF-1 production is abnormal. In addition the change in IGF-1 production and/or IGF-1 PR SDS can be calculated to determine what an appropriate therapy might be to restore IGF-1 blood concentrations. In embodiments where rhIGF-1 is the appropriate therapy, the replacement dose of rhIGF-1 or an effective combination of rhIGF-1 and an agent that increases a blood level of GH, can be directly calculated to restore blood IGF-1 levels to an appropriate level.

The present invention features a computer program product including a computer readable storage medium having a computer program stored thereon, wherein the computer program, when read by a computer, executes transformation of an insulin-like growth factor-1 (IGF-1) concentration in blood to an IGF-1 standard deviation score (SDS). In some embodiments, the program calculates the IGF-1 SDS using the algorithm:

$$\text{IGF-1 SDS} = (x^p - \text{mean}_{age}) \div \text{SD}_{age},$$

wherein x is the IGF-1 concentration in blood.

In some embodiments, the transformation of IGF-1 concentration in blood to an IGF-1 SDS comprises transformation of the IGF-1 concentration in blood to an IGF-1 clearance rate in blood using an IGF-1 binding protein-3 (IGFBP-3) concentration in blood. In certain embodiments, the IGF-1 concentration in blood or the IGF-1 production rate in blood is adjusted for a blood concentration of insulin-like growth factor-2 (IGF-2). In other embodiments, the computer program further executes transformation of the IGF-1 clearance rate to an IGF-1 production rate. In further embodiments, the IGF-1 production rate is calculated using the algorithm:

$$\text{IGF-1}_{production\ rate} = (\text{IGF-1}_{blood\ conc.})(\text{clearance rate of (IGF-1)}).$$

In certain embodiments, the computer program executes transformation of the IGF-1 production rate to an IGF-1 production rate SDS (IGF-1 PR SDS). In further embodiments, computer program calculates the IGF-1 PR SDS using the algorithm:

$$\text{IGF-1 PR SDS} = (x^p - \text{mean}_{age}) \div \text{SD}_{age}$$

wherein x is the IGF-1 production rate in blood. In some embodiments, the computer program further includes an algorithm for computing IGF-1 concentration in blood at baseline to provide a first IGF-1 SDS, computing IGF-1 concentration in blood in response to growth hormone (GH) administration to provide a second IGF-1 SDS, and computing a change in IGF-1 SDS between said first and second IGF-1 SDS.

In some embodiments, the computer program further includes an algorithm for computing IGF-1 production rate in blood at baseline to provide a first IGF-1 PR SDS, computing IGF-1 production rate in response to growth hormone (GH) administration to provide a second IGF-1 PR SDS, and computing a change in IGF-1 PR SDS between said first and second IGF-1 PR SDS.

Another feature of the present invention is a diagnostic system for diagnosing an insulin-like growth factor-1 deficiency (IGFD) in a subject, the system including a central computing environment, an input device, operatively connected to the computing environment, to receive patient data, wherein the patient data include age, and insulin-like growth factor-1 (IGF-1) blood concentration, an output device, operatively connected to the computing environment, to provide information to a user, and an algorithm executed by the central computing environment, wherein the algorithm is executed based on the data received by the input device, and wherein the algorithm executes transformation of the IGF-1 blood concentration to an IGF-1 standard deviation score (SDS), wherein the SDS is communicated to the output device. In certain embodiments, the system further includes a data storage means.

In some embodiments, the algorithm is of the formula:

$$\text{IGF-1 SDS} = (x^p - \text{mean}_{age}) \div \text{SD}_{age}$$

wherein x is the IGF-1 blood concentration. In other embodiments, the central computing environment executes transformation of the IGF-1 concentration in blood to an IGF-1 clearance rate in blood based on an IGF-1 binding protein-3 (IGFBP-3) concentration in blood. In further embodiments, the IGF-1 concentration in blood or the IGF-1 production rate in blood is adjusted for a blood concentration of insulin-like growth factor-2 (IGF-2). In some embodiments, the central computing environment executes transformation of the IGF-1 clearance rate to an IGF-1 production rate.

In some embodiments, the central computing environment calculates the IGF-1 production rate using the algorithm:

$$\text{IGF-1}_{production\ rate} = (\text{IGF-1}_{blood\ conc.})(\text{clearance rate of (IGF-1)}).$$

In other embodiments, the central computing environment executes transformation of the IGF-1 production rate to an IGF-1 production rate SDS (IGF-1 PR SDS). In further embodiments, the central computing environment calculates the IGF-1 PR SDS using the algorithm:

$$\text{IGF-1 PR SDS} = (x^p - \text{mean}_{age}) \div \text{SD}_{age}$$

wherein x is the IGF-1 production rate in blood. In other embodiments, the central computing environment further includes an algorithm for computing IGF-1 concentration in blood at baseline to provide a first IGF-1 SDS, computing IGF-1 concentration in blood in response to growth hormone (GH) administration to provide a second IGF-1 SDS, and computing a change in IGF-1 SDS between said first and second IGF-1 SDS. In further embodiments, the output device further includes a differential diagnosis means, wherein a change in IGF-1 SDS of at least +1.0 indicates a diagnosis of responsiveness to GH therapy and indicates treatment with GH, a change in IGF-1 SDS less than +1.0 indicates non-responsiveness to GH therapy and indicates treatment with IGF-1; and a change in IGF-1 SDS of about +0.5 to +1.5 indicates treatment with a combination of GH and IGF-1.

In other embodiments, the central computing environment further includes an algorithm for computing IGF-1 production rate in blood at baseline to provide a first IGF-1 PR SDS, computing IGF-1 production rate in response to growth hormone (GH) administration to provide a second IGF-1 PR SDS, and computing a change in IGF-1 PR SDS between said first and second IGF-1 PR SDS. In further embodiments, the output device further includes a differential diagnosis means, wherein a change in IGF-1 PR SDS of at least +1.0 indicates a diagnosis of responsiveness to GH therapy and indicates treatment with GH, a change in IGF-1 PR SDS less than +1.0 indicates non-responsiveness to GH therapy and indicates treatment with IGF-1, and a change in IGF-1 PR SDS of about +0.5 to +1.5 indicates treatment with a combination of GH and IGF-1.

Yet another feature of the invention is a portable apparatus for diagnosing an insulin-like growth factor-1 deficiency (IGFD) in a patient, including a means for receiving and storing patient data, wherein the data comprise age of the patient and insulin-like growth factor-1 (IGF-1).concentration in a biological sample from the patient, a data output means, and an algorithm stored within the apparatus, which algorithm executes transformation of the IGF-1 blood concentration, received from the receiving means, to an IGF-1 standard deviation score (SDS), which SDS is transmitted to the data output means, wherein the output means displays the SDS to a user.

In some embodiments, the apparatus further includes a device for measuring the IGF-1 concentration in the biological sample; and a means for communicating the measured IGF-1 concentration to the receiving and storage means. In some embodiments, the device includes an enzyme-linked immunosorbent assay, a chemiluminescent assay, or a radio-immunoassay. In some embodiments, the program calculates the IGF-1 SDS using the algorithm:

$$\text{IGF-1 SDS} = (x^p - \text{mean}_{age}) \div \text{SD}_{age}$$

wherein x is the IGF-1 concentration in blood.

In other embodiments, the apparatus further includes an algorithm executes transformation of the IGF-1 concentration in blood to an IGF-1 clearance rate in blood based on an IGF-1 binding protein-3 (IGFBP-3) concentration in blood. In certain embodiments, the IGF-1 concentration in blood or the IGF-1 production rate in blood is adjusted for a blood concentration of insulin-like growth factor-2 (IGF-2). In other embodiments, the algorithm executes transformation of the IGF-1 clearance rate to an IGF-1 production rate. In some embodiments, the algorithm for calculating the IGF-1 production rate is:

$$\text{IGF-1}_{production\ rate} = (\text{IGF-1}_{blood\ conc.})(\text{clearance rate of (IGF-1)}).$$

In other embodiments, the program executes transformation of the IGF-1 production rate to an IGF-1 production rate SDS (IGF-1 PR SDS). In further embodiments, the algorithm for calculating the IGF-1 PR SDS is:

$$\text{IGF-1 PR SDS} = (x^p - \text{mean}_{age}) \div \text{SD}_{age}$$

wherein x is the IGF-1 production rate in blood.

In still other embodiments, the apparatus further includes an algorithm for computing IGF-1 concentration in blood at baseline to provide a first IGF-1 SDS, computing IGF-1 concentration in blood in response to growth hormone (GH) administration to provide a second IGF-1 SDS, and computing a change in IGF-1 SDS between said first and second IGF-1 SDS. In some embodiments, the apparatus further includes an algorithm for computing IGF-1 production rate in blood at baseline to provide a first IGF-1 PR SDS, computing IGF-1 production rate in response to growth hormone (GH) administration to provide a second IGF-1 PR SDS, and computing a change in IGF-1 PR SDS between said first and second IGF-1 PR SDS.

Yet another feature of the presnet invention is a method of diagnosing primary and secondary insulin-like growth factor-1 deficiency (IGFD) in a subject, including transforming an insulin-like growth factor-1 (IGF-1) blood concentration to an IGF-1 standard deviation score (SDS), wherein the transformation comprises applying an algorithm of the formula $$\text{IGF-1 SDS} = (x^p - \text{mean}_{age}) \div \text{SD}_{age}$$

wherein x is the IGF-1 blood concentration; and making a diagnosis of primary or secondary IGFD based on the SDS. In some embodiments, the IGF-1 SDS is derived using the system of the present invention In some embodiments, the method further includes transforming the IGF-1 concentration in blood to an IGF-1 production rate, and then transforming the IGF-1 production rate to an IGF-1 production rate standard deviation score (IGF-1 PR SDS) by applying an algorithm of the formula $$\text{IGF-1 PR SDS} = (x^p - \text{mean}_{age}) \div \text{SD}_{age}$$

wherein x is the IGF-1 production rate. In further embodiments, the transforming of IGF-1 concentration in blood to IGF-1 production rate is by using the algorithm:

$$\text{IGF-1}_{production\ rate} = (\text{IGF-1}_{blood\ conc.})(\text{clearance rate of IGF-1}).$$

Yet another feature of the present invention is a method of treating an insulin-like growth factor-1 deficiency (IGFD) disorder in an individual, including determining a standard deviation score, wherein the standard deviation score is an IGF-1 standard deviation score (SDS) calculated using an IGF-1 blood concentration in a biological sample from the individual; administering to the individual, based on the standard deviation score, an effective amount of IGF-1, an IGF-1 analog, an IGF-1 variant, or an agent that increases the blood concentration of growth hormone (GH), or a combination thereof, said administering being effective to treat IGFD in the individual.

In some embodiments, the standard deviation score is an IGF-1 production rate standard deviation score (IGF-1 PR SDS), which IGF-1 PR SDS is based on an IGF-1 production rate calculated from the IGF-1 blood concentration in the biological sample from the individual. In other embodiments, the administering includes administering to the individual an agent that increases blood concentration of GH and at least one of IGF-1, an IGF-1 analog, and an IGF-1 variant. In some embodiments, the IGFD disorder is short stature. In other embodiments, the IGFD disorder is a metabolic disorder.

Yet another feature of the present invention provides a method of diagnosing primary and secondary insulin-like growth factor-1 deficiency (IGFD) in a subject, including determining a baseline insulin-like growth factor-1 (IGF-1) standard deviation score (SDS), wherein the baseline IGF-1 SDS is an IGF-1 production rate standard deviation score (IGF-1 $SDS_{baseline\ production\ rate}$) calculated using an IGF-1 blood concentration and an IGF-1 clearance rate in a first blood sample taken from the individual, administering to the individual an amount of growth hormone (GH) effective to stimulate IGF-1 production in a normal subject of the same age and gender as the individual, determining a post-GH therapy IGF-1 SDS, wherein the post-GH therapy IGF-1 SDS is an IGF-1 production rate standard deviation score (IGF-1 $SDS_{post-therapy\ production\ rate}$) calculated using an IGF-1 blood concentration and an IGF-1 clearance rate in a second blood sample taken from the individual at a time after said administration of GH at which IGF-1 production would be stimulated in a normal subject in response to said administration of GH; and diagnosing primary or secondary IGFD in the individual based on a comparison of IGF-1 $SDS_{baseline\ production\ rate}$ and IGF-1 $SDS_{post-therapy\ production\ rate}$. In some embodiments, the comparison is performed by subtracting IGF-1 $SDS_{baseline\ production\ rate}$ from IGF-1 $SDS_{post-therapy\ production\ rate}$ to obtain a change in IGF-1 PR SDS. In some embodiments, the IGF-1 $SDS_{baseline\ production\ rate}$ and IGF-1 $SDS_{post-therapy\ production\ rate}$ are each calculated using the system of the present invention.

In some embodiments, a change in IGF-1 PR SDS less than +1.0 indicates a diagnosis of primary IGFD. In further embodiments, the method further includes the step of administering to the subject an amount of IGF-1 effective for the treatment of primary IGFD in the subject.

In other embodiments, a change in IGF-1 PR SDS between +0.5 and +1.5 indicates a diagnosis of a combination of primary and secondary IGFD. In further embodiments, the method further includes the step of administering to the subject an amount of IGF-1 and an amount of GH that in combination are effective for the treatment of primary and secondary IGFD in the subject.

In still other embodiments, a change in IGF-1 PR SDS at least +1.0 indicates a diagnosis of secondary IGFD. In further embodiments, the method further includes the step of administering to the subject an amount of GH effective for the treatment of secondary IGFD in the subject.

BRIEF DESCRIPTION OF THE DRAWINGS

FIGS. 2A-2C depict exemplary embodiments of a subject system.

FIG. 3 depicts an embodiment of a subject apparatus.

DEFINITIONS

Figure 1:
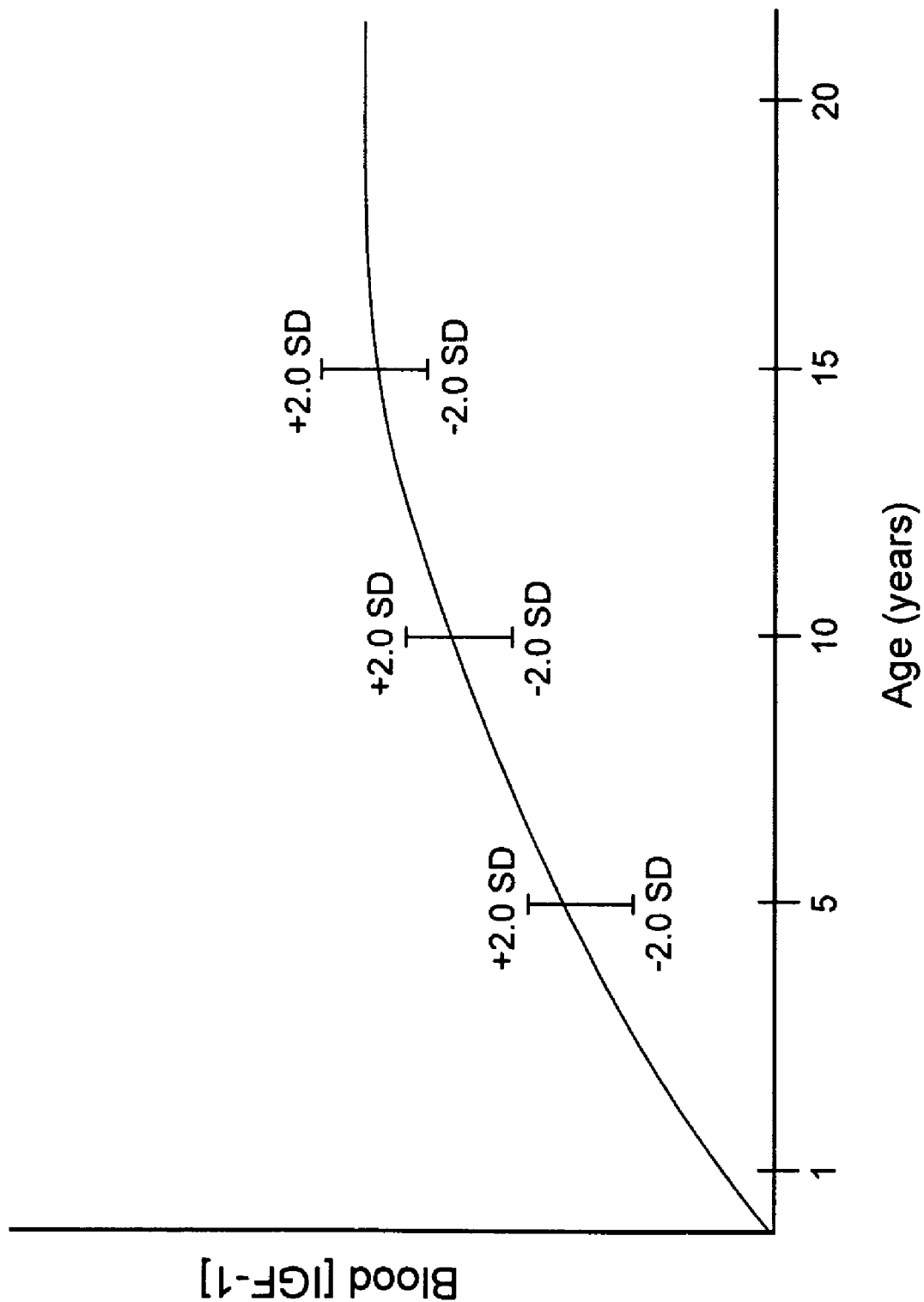
FIG. 1 depicts an exemplary plot of blood IGF-1 concentration vs. age, in years.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease, disorder, or condition, and/or adverse affect attributable to the disease. "Treatment," as used herein, covers any treatment of a disease, disorder, or condition in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease. "Treatment" also includes providing positive benefits to a subject, including physical, mental, and emotional benefits. In particular embodiments, the terms treatment," "treating," and the like, refer increasing the growth rate of an individual, increasing the final adult height of an individual, etc.

The terms "individual," "host," "subject," and "patient," used interchangeably herein, refer to a mammal, particularly a human.

The term "therapeutically effective amount" is meant an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "binds specifically," in the context of antibody binding, refers to high avidity and/or high affinity binding of an antibody to a specific polypeptide i.e., epitope of a polypeptide, e.g., an IGF-1 polypeptide. For example, antibody binding to an epitope on an IGF-1 polypeptide or fragment thereof is stronger than binding of the same antibody to any other epitope, particularly those which may be present in molecules in association with, or in the same sample, as the specific polypeptide of interest, e.g., binds more strongly to an IGF-1 epitope than to a epitope of a non-IGF-1 polypeptide so that by adjusting binding conditions the antibody binds almost exclusively to the specific IGF-1 polypeptide epitope and not to any other, non-IGF-1, epitope, or to any other polypeptide which does not comprise the epitope. Antibodies that bind specifically to an IGF-1 polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

As used herein, "IGF-1" refers to insulin-like growth factor-1 from any species, including bovine, ovine, porcine, equine, and human. The term "IGF-1" also includes naturally-occurring IGF-1 (e.g., IGF-1 isolated from a naturally-occurring source of IGF-1); synthetic IGF-1; and recombinant IGF-1.

The term "IGF-1 concentration in blood" or the term "IGFBP-3 concentration in blood" refers to a concentration of IGF-1 or IGFBP-3, respectively, obtained in whole blood or in a fluid obtained from blood, such as plasma or serum.

As used herein, "IGF-2" refers to insulin-like growth factor-2 from any species, including bovine, ovine, porcine, equine, and human. The term "IGF-2" also includes naturally-occurring IGF-1 (e.g., IGF-2 isolated from a naturally-occurring source of IGF-1); synthetic IGF-2; and recombinant IGF-2.

The term "IGF-2 concentration in blood" or the term refers to a concentration of IGF-2 obtained in whole blood or in a fluid obtained from blood, such as plasma or serum.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "body fluid" and "bodily fluid," used interchangeably herein, refer to a biological sample of liquid from a mammal, e.g., from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts. Particular bodily fluids that are interest in the context of the present invention include serum, plasma, and blood.

A "computer-based system" refers to the hardware means, software means, and data storage means used to analyze information. The minimum hardware of a subject computer-based system comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

By "clinical assay" is meant an assay or test that is performed on a sample obtained from an individual or patient (also referred to herein as host or subject) in order to provide information on current or future health or condition, diagnosis, treatment, prevention, and/or monitoring of a condition of the individual or patient.

The term "evaluate" is used herein broadly to refer not only to the diagnosis or detection of a given condition of interest, but also to the monitoring of a condition over a given period of time. As such, in certain embodiments one uses the subject methods to diagnose a subject for the presence of a given condition, i.e., to determine whether a subject has a given condition (e.g., IGFD, including primary IGFD, secondary IGFD, severe primary IGFD, etc.). In yet other embodiments, one uses the subject methods to monitor, predict, or track, i.e., watch or observe, the progression of a condition in a subject over a period of time.

The term "production" as used in the context of "IGF-1 production" (e.g., in an unstimulated state or a stimulated response such as to administration of growth hormone to an individual) refers to IGF-1 levels in serum of a patient produced in response to GH, which can be assessed by quantitative or qualitative measure. IGF-1 in its active state (e.g., unbound to IGF-1 binding protein) can be present in the blood stream as a as a result of de novo production and/or as a result of release from an inactive state (e.g., due to release from an IGF-1 binding protein). As such, IGF-1 production also including assessing IGF-1 blood concentrations, taking into account blood IGF-2 concentrations, taking into account IGFBP-3 blood concentrations (and, optionally, IGF-2 concentrations), to provide an "IGFBP-3 adjusted. IGF-1" blood production rate. Adjusted IGF-1 blood concentration for clearance based on IGFBP-3 concentrations provide an IGF-1 production rate and are particularly useful in determining the IGF-1 generated in a patient in an unstimulated state or in response to stimulation or therapy (e.g., with growth hormone (GH) or other agent). In some embodiments, the change in IGF-1 SDS is generated based on IGF-1 blood concentration unadjusted for either IGFBP-3 or IGF-2. In other embodiments, the change in IGF-1 PR SDS is generated based on the amount of IGF-1 and IGFBP-3 in the blood. In yet other embodiments, the change in "IGF-2 adjusted" IGF-1 PR SDS is generated based on an adjusted amount of IGF-1 taking into account the amount of IGFBP-3 in the blood as well as the amount of IGF-2 in the blood.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during the pre-selected time period (e.g., an 8 hour interval) never falls to zero. Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

An "IGF-1 deficiency disorder" is any condition that would benefit from treatment with an IGF, including but not limited to, for example, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, undesirable symptoms associated with aging such as obesity and increased fat mass-to-lean ratios, immunological disorders such as immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth. Disorders of bone or cartilage growth in children, including short stature, and in children and adults disorders of cartilage and bone in children and adults, including arthritis and osteoporosis. The disorder being treated may be a combination of two or more of the above disorders (e.g., osteoporosis that is a sequela of a catabolic state). Specific disorders of interest targeted for treatment herein are diabetes and obesity, heart dysfunctions, kidney disorders, neurological disorders, bone disorders, whole body growth disorders, and immunological disorders.

As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. An example of a hyperglycemic disorder is diabetes, especially Type 1 and Type II diabetes. "Diabetes" itself refers to a progressive disease of carbohydrate metabolism involving inadequate production or utilization of insulin and is characterized by hyperglycemia and glycosuria.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an assay" includes a plurality of such assays and reference to "the IGF-1 polypeptide" includes reference to one or more IGF-1 polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a standard deviation score (SDS) calculator, which SDS is useful for transforming insulin-like growth factor-1 (IGF-1) concentrations to IGF-1 standard deviation scores. The present invention further provides a system and device for transforming an IGF-1 concentration to an IGF-1 SDS. The present invention also provides for assessing IGF-1 blood concentrations, taking into account blood IGF-2 concentrations, taking into account IGFBP-3 blood concentrations (and, optionally, IGF-2 concentrations), to provide an "IGFBP-3 adjusted IGF-1" blood production rate. Adjusted IGF-1 blood concentration for clearance based on IGFBP-3 concentrations provide an IGF-1 production rate and are particularly useful in determining the IGF-1 generated in a patient in an unstimulated state or in response to stimulation or therapy (e.g., with growth hormone (GH) or other agent).

Determination of an IGF-1 SDS permits a diagnosis of primary IGF-1 deficiency (IGFD) or secondary IGFD. The present invention further provides methods of diagnosing primary IGFD and secondary IGFD. The first method generally involves converting an IGF-1 concentration in a biological sample to an IGF-1 SDS; and, based on the IGF-1 SDS, making a diagnosis of primary or secondary IGFD. The second method generally involves adjusting the IGF-1 blood level to take into account a blood level of IGFBP-3, to provide an IGF-1 production rate. The IGF-1 production rate is particularly useful in calculating the amount of IGF-1 generated in a patient before and after IGF-1 generation is stimulated. Further, the IGF-1 production rate can be used in the IGF-1 SDS calculator to provide an IGF-1 production rate SDS (IGF-1 PR SDS). Further, the IGF-2 blood level can be used to further modify the IGF-1 production rate which can be used in the IGF-1 SDS calculator to provide an "IGF-2 adjusted" IGF-1 PR SDS.

The present invention further provides kits, devices, and systems for carrying out a subject diagnostic method. The present invention further provides methods of treating IGFD, the methods generally involving determining an IGF-1 SDS; and, based on the IGF-1 SDS, or based on the amount of IGF-1 generated (by determining the IGF-1 production rate before or after IGF-1 generation is stimulated by administration of an agent, e.g., growth hormone), administering an effective amount of IGF-1, an agent that increases a blood level of growth hormone (GH), or an effective combination of IGF-1 and an agent that increases a blood level of GH.

Transforming an IGF-1 Concentration to an IGF-1 SDS

The instant invention provides a method of calculating blood IGF-1 standard deviation score (SDS). In one embodiment, the values of the IGF-1 blood concentration are used in combination with the IGFBP-3 blood concentration to calculate the IGF-1 clearance and thus the IGF-1 production rate which is then modified using the SDS calculator. In another embodiment, the IGF-1 blood concentration, the IGFBP-3 blood concentration, and the IGF-2 blood concentration are used to provide an "IGFBP-3/IGF-2 adjusted" IGF-1 production rate. These adjusted IGF-1 values can be used in the SDS calculator of the invention.

The SDS value is useful for determining whether a given IGF-1 blood concentration for an individual of a particular age is within the normal range, or outside of the normal range. FIG. 1 depicts an exemplary plot of blood IGF-1 concentration versus age, in years. A similar plot of the IGF-1 production rate SDS can also be constructed, as can the "IGF-2 adjusted" IGF-1 PR SDS.

The instant invention provides a method of predicting whether an individual having IGFD is suffering from primary or secondary IGFD, whether or not they will respond to treatment with GH, an agent that increases blood levels of GH, or a combination of IGF-1 and an agent that increases blood levels of GH. The method generally involves calculating the standard deviation score for the individual based on the age of the individual, the gender of the individual, and the blood IGF-1 concentration of the individual. The SDS for the individual is calculated using the following formula:

$$SDS_{age}=(x^p-mean_{age})\div SD_{age}.$$

wherein x is blood concentration of IGF-1, p is a power transformation, and $SD_{age}$ is a value obtained from a smooth mean curve generated by plotting IGF-1 blood concentration values as a function of age.

The present invention provides a method for calculating blood IGF-1 standard deviation scores. The method generally involves performing a series of calculations on blood IGF-1 concentrations from individuals of various ages, and genders, to obtain standard deviation score for each age. The method generally involves performing the following steps: a) perform a power transformation on IGF-1 blood concentration values for each age; b) generate a smooth mean curve as a function of age, using the transformed IGF-1 blood concentration values from step (a); c) derive the standard deviation for each age. The SD score for each subject in the corresponding normative sample is computed as $SDS=(x^p-mean_{age})\div SD_{age}$, where x is the blood IGF-1 concentration, and $x^p$ is the power transformed IGF-1 value.

Step (a) involves generating a power transformation. A power transformation on IGF-1 concentration values for each age is performed using any standard method, e.g., as described in Brabant et al. Brabant et al. ((2003) *Horm Res.* 60(2):53-60); or Kuczmarski et al. ((2002) *Vital Health Stat* 11(246):1-190). Typically, this involves empirically determining the power to which the IGF-1 concentration must be raised to reduce the skewness and kurtosis to as close to zero as possible.

Step (b) involves generating a smooth mean curve as a function of age, using the transformed IGF-1 blood concentration values from step (a). In many embodiments, a loess-based regression method is used. For example, the smoothing function LOESS in the R open-source software package may be used. The source code for the regression algorithm, which runs under the open-source statistical package R, is available on the Internet at the following World Wide Web site: r-project.org. LOESS is derived from the S statistical function LOWESS, which uses a locally weighted least squares estimate of a regression fit. Cleveland W S (1979) Robust Locally Weighted Regression and Smoothing Scatterplots, *Journal of the American Statistical Association* 74:829-836. For example, a linear (or quadratic) regression line is fit to continuous sections of the data. The function is then applied in continuity to the rest of the data set, using a moving window of local data points to derive a fit line, the result being a smoothed curvilinear regression line. The amount of fitting and smoothing that takes place is governed by the span parameter of the LOESS function which sets the proportion of the total data set to be used in each window for local fitting.

Step (c) involves determining the standard deviation for each age. The mean absolute deviations from the smoothed mean from step (b) are fit using loess, as described for step (b). This is used to derive the standard deviation for each age.

In some embodiments, the method further involves d) determining the SD score for each subject (e.g., IGF-1 value for each subject), using the formula:

SDS=(power transformed IGF-1 value−smoothed mean for age)÷smoothed standard deviation for age.

Thus, for a given individual, the standard deviation score= $(x^p-mean_{age})\div SD_{age}$, where x is the IGF-1 concentration (e.g., the IGF-1 blood concentration).

In some embodiments, the method further involves e) plotting the SD scores from step (d) by age, and evaluating the characteristics of the SD scores by their overall mean, skewness, and kurtosis, each of which should be close to or at zero, and standard deviation, which should be close to or about 1; and by the Wilk-Shapiro test for fit to the normal distribution.

In some embodiments, the method further involves repeating steps (a)-(e) for several different power transformations (p values) and different levels of smoothing.

In some embodiments, the p value ranges from about 0.2 to about 0.5, including from about 0.21 to about 0.49, from about 0.22 to about 0.48, from about 0.23 to about 0.47, from about 0.24 to about 0.46, from about 0.25 to about 0.45, from about 0.26 to about 0.44, from about 0.27 to about 0.43, from about 0.28 to about 0.42, from about 0.29 to about 0.41, from about 0.30 to about 0.40, from about 0.31 to about 0.39, from about 0.32 to about 0.38, from about 0.33 to about 0.37, from about 0.34 to about 0.36, including about 0.35. In particular embodiments, the p value is about 0.3, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.48, about 0.5.

A change in IGF-1 SDS following GH stimulation can be used to determine an appropriate therapy for the subject. An IGF-1 SDS is determined at each of baseline and post-therapy, and a change in the IGF-1 SDS can be calculated. A change in IGF-1 SDS of at least +1.0, and especially +2.0 or more, indicates the subject is responsive to GH therapy. However, where the change in IGF-1 SDS is less than +1.0, then the subject is not responsive to GH and therapy with IGF-1 can be indicated. Where the change in IGF-1 SDS is borderline, e.g., +0.5 to +1.5, then a combination therapy of, for example, GH and IGF-1 is indicated.

Furthermore, the IGF-1 blood level and the IGFBP-3 blood level, as further described below, can be used to calculate the IGF-1 production rate, which can then be used in the IGF-1 SDS calculator to provide an IGF-1 PR SDS. In addition, the IGF-2 blood level can be taken into account when determining the IGF-1 production rate, which can be used in the IGF-1 SDS calculator to provide an "IGF-2 adjusted" IGF-1 PR SDS.

Computer Program Product

The above-described steps for transforming an IGF-1 concentration to an IGF-1 SDS can be carried out by a human, e.g., manually performing each step. Alternatively, the above-described steps can be completely or partially performed by a computer program product. The present invention thus provides a computer program product including a computer readable storage medium having a computer program stored on it. The program can, when read by a computer, executes transformation of an IGF-1 blood concentration to an IGF-1 SDS, e.g., calculates an IGF-1 SDS based on the IGF-1 blood concentration. The computer program product has stored therein a computer program for performing the above-described algorithm on an IGF-1 concentration.

Method and Device for Transforming an IGF-1 Concentration to an IGF-1 SDS

A subject algorithm is applied to any given IGF-1 blood concentration, to determine whether the IGF-1 blood concentration is within the normal range, or whether the IGF-1 blood concentration is below or above normal (e.g., below or above a normal mean IGF-1 blood concentration, or below or above a normal range of IGF-1 blood concentration (e.g., a SD of −2.0 to +2.0), in response to GH. The algorithm can be applied to an IGF-1 concentration manually (e.g., by an individual). Alternatively, the algorithm can be applied to an IGF-1 concentration by a computer. Accordingly, the present invention provides a computer program that carries out the transformation of an IGF-1 concentration to an IGF-1 SDS.

Transforming IGF-1 Blood Level to an IGF-1 Production Rate SDS

In some embodiments, IGF-1 blood concentration can be used along with the IGF-1 clearance, which is calculated from the IGFBP-3 blood concentration, to calculate the IGF-1 production rate. Such an IGF-1 production rate more accurately reflects the subject's clinical status, particularly in the context of IGF-1 induction (also referred to as IGF-1 generation or IGF-1 production) after therapy (e.g., such as that which results by administration of growth hormone (GH)).

This "IGF-1 production rate" is of particular value in analyzing whether IGF-1 is generated in a subject in response to growth hormone or other agent that increases IGF-1 (particularly an agent that also increases IGFBP-3 blood concentration). Thus, in some embodiments, the present invention provides an SDS calculator for determining an IGF-1 production rate SDS ("IGF-1 PR SDS") based on the amount of IGF-1 generated in response to increasing blood GH levels or increasing the activity of the GH receptor. The method generally involves performing a series of calculations on blood IGF-1 concentrations, IGFBP-3 blood concentrations (and, optionally, IGF-2 blood concentrations), and IGF-1 production rates from individuals of various ages, and genders, to obtain standard deviation score for each age and gender to provide a normative dataset (which may be produced using methods known in the art, e.g., the normalization methods described above). Such a normative dataset can then be used in the methods of the subject invention to evaluate the responsiveness of a subject to GH therapy.

This aspect of the invention is based in part on the observation that IGF-1 Binding Protein-3 (IGFBP-3) binds free IGF-1, forming an IGFBP-3/IGF-1 complex, which then binds to the Acid Labile Subunit (ALS) forming a trimeric complex, which is then cleared very slowly from the blood. It is shown in this application that the concentration of the IGFBP-3 in blood determines almost all the variation in the clearance of IGF-1 from the blood. In this invention the relationship between the concentration of IGFBP-3 and the clearance of IGF-1 is precisely defined using new data generated by administering IGF-1 to patients with a broad range of IGFBP-3 concentrations. With this new knowledge, of the mathematical relationship between the concentration of IGFBP-3 in the blood and the clearance of IGF-1, it is possible for the first time to calculate the production rate of IGF-1 with precision. This can be accomplished by measuring the concentration of IGF-1 and IGFBP-3 in the blood of a patient and then applying an algorithm described herein.

One advantage of this new method can be illustrated by example. For example, two patients A and B of the same age and sex may have equal and low blood IGF-1 concentrations, and therefore equal and low IGF-1 SDS scores. Such patients may thus be seen as equally IGF-1 deficient. However, patient A has a blood IGFBP-3 concentration that is only 10% of that of patient B. This is known to occur, as blood IGF-1 and IGFBP-3 concentrations are separately regulated and so do not always change in concentration in a coordinate manner.

From the above discussion it can now be seen that the low IGFBP-3 concentration in patient A, in the presence of low IGF-1 concentrations, predicts that patient A will have a higher rate of IGF-1 generation compared to patient B. The situation in these 2 patients following GH levels being increased as part of an IGF-1 induction test (which may also be referred to as an IGF-1 generation test) also needs to be considered. In one situation, blood IGF-1 levels might increase to the same level in both patients, yielding the same IGF-1 SDS score after stimulation by GH. In this situation the amount of IGF-1 generated in patient A will be seen to be greater than in patient B due to the higher blood IGFBP-3 levels in patient B prolonging the half-life of the IGF-1 generated in patient B.

Another complexity is that IGFBP-3 levels are closely and chiefly regulated by blood GH concentrations, GH exposure and the GH receptor being activated. Therefore following an IGF-1 generation test or IGF-1 production test where blood GH concentrations are increased it is likely that IGFBP-3 levels will also increase. It can be seen that an increase in blood IGFBP-3 levels could increase blood IGF-1 levels and increase the IGF-1 SDS score in the absence of a change in IGF-1 production, or possibly even in the presence of a fall in IGF-1 production. There is therefore a need to take account of IGFBP-3 levels when determining IGF-1 blood levels, particularly in the context of IGF-1 generation, IGF-1 production or IGF-1 exposure which is clearly apparent.

Figure 5A:
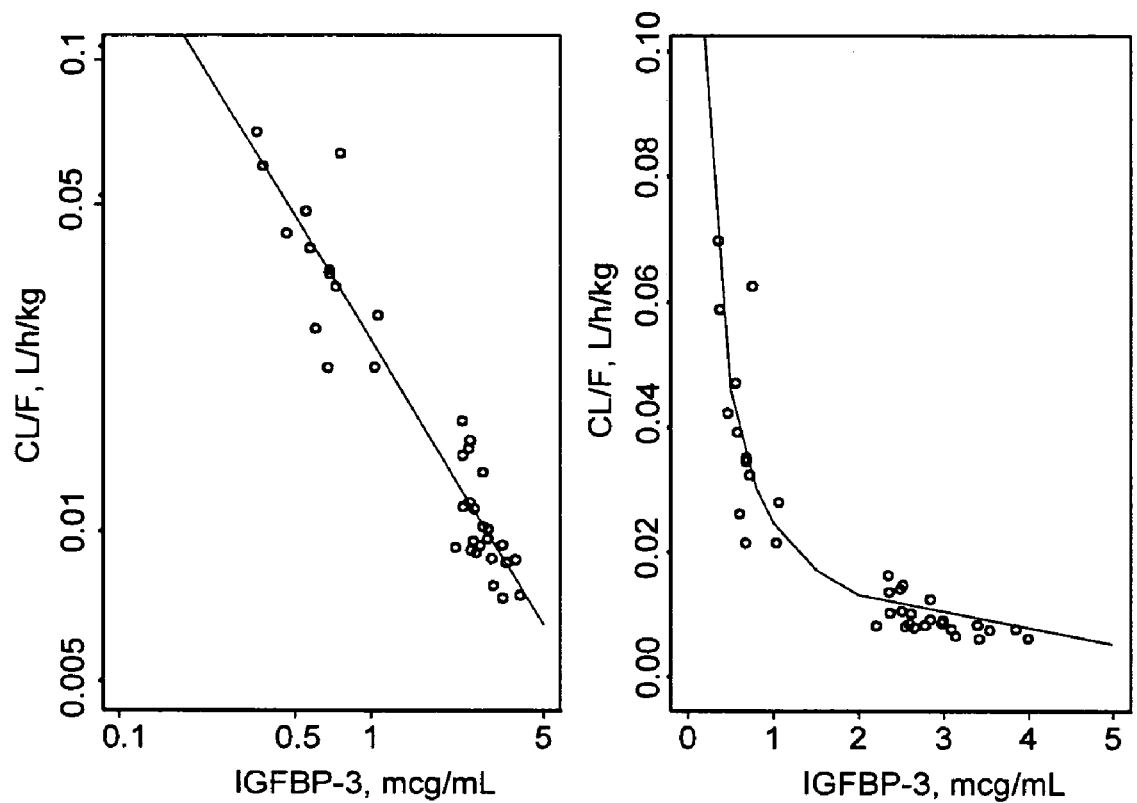
FIG. 5A is set of graphs depicting the relationship between IGF-1 Binding Protein-3 (IGFBP-3) and IGF-1 clearance. Log-log scale is represented in left panel, while linear scale is represented in right panel. The solid line represents the model-predicted function.

An IGFBP-3-adjusted IGF-1 blood level, which takes into account a blood level of IGFBP-3 can be calculated as provided herein. The IGFBP-3 concentration is measured, and from the relationship between IGFBP-3 and IGF-1 clearance as established in this application (see, e.g., FIG. 5A), the clearance rate of IGF-1 determined. The production rate of IGF-1 can then be calculated using the following equation:

$$\text{IGF-1}_{production\ rate} = (\text{IGF-1}_{blood\ conc.})(\text{clearance rate of (IGF-1)})$$

where IGF-1 production (mcg/kg/hr) is the adjusted IGF-1 blood level, IGF-1$_{blood\ conc.}$ is a blood level of IGF-1 (e.g., in mg/kg), and clearance rate of (IGF-1) is the clearance rate of IGF-1 as determined using FIG. 5A.

The determination of IGF-1$_{production}$ is shown by the following example. For example a blood sample is taken from two patients of the same age and gender and the levels of IGF-1 and IGFBP-3 may be as follows:

|           | IGF-1 blood level | IGFBP-3 blood level |
|-----------|-------------------|---------------------|
| Patient A | 100 ng/ml         | 3 micrograms/ml     |
| Patient B | 100 ng/ml         | 0.5 micrograms/ml   |

Using an IGF-1 SDS, these two patients would have the same IGF-1 SDS. However based on the different IGFBP-3 level in their blood, the expected clearance of IGF-1 would be different, thereby affecting the overall level of IGF-1 in their blood over time. Using FIG. 5A, by inspection, the clearance rate (clearance (IGF-1)) can be obtained as follows.

|           | IGFBP-3 blood level | Systemic Clearance (CL/F) |
|-----------|---------------------|---------------------------|
| Patient A | 3 micrograms/ml     | 0.01 L/hr/kg              |
| Patient B | 0.5 micrograms/ml   | 0.05 L/hr/kg              |

Therefore, using the formula IGF-1$_{Adj}$=(IGF-1$_{blood\ conc.}$)(clearance(IGF-1)), the adjusted IGF-1 blood level for the two patients would be as follows:

IGF-1$_{Adj}$=(100 ng/ml×0.01 L/hr/kg)=1 ug/kg/hr     Patient A

IGF-1$_{Adj}$=100 ng/ml×0.05 L/hr/kg)=5 ug/kg/hr     Patient B

Accordingly, these patients would have a 5-fold difference in IGF-1 production rate.

In further embodiments, exposure of the subject to GH (or other agent administered to stimulate IGF-1 production) is taken into account in the methods of the invention, particularly when assessing IGF-1 production rate as described herein. In this embodiment, the blood level of GH (or other agent) is assessed after administration, preferably at a time point after $T_{max}$ (time to $C_{max}$, the maximum serum concentration e.g., at least about 2 hrs after subcutaneous GH administration). The blood level of GH is then taken into account when determining responsiveness to GH as assessed by IGF-1 production rate. For example, if the GH blood concentration is less than a selected cut-off blood concentration, then failure of the subject to respond to GH therapy by production of IGF-1 may be explained by insufficient exposure of the patient to GH rather than to the presence of a GH resistant condition in the patient.

A normative data set for GH exposure over time for varying ages and genders can be generated by measuring GH blood concentration and IGF-1 production rate in normal individuals, and GH blood concentration plotted against IGF-1 production rate. The normative dataset can be generated and/or analyzed using methods known in the art, e.g., the normalization methods described above. The GH blood concentration and IGF-1 production rate in a patient can then be compared to this normative data set. If the GH blood concentration in the patient is high and the IGF-1 production rate low, then a diagnosis of primary IGFD can be made. If the IGF-1 production rate is below normal (e.g., below the normal mean, or below the normal range) and the GH blood concentration is a concentration that when compared with the normative data set would not be expected to stimulate IGF-1 production, then no diagnosis can be made.

Adjusting IGF-1 blood concentration for IGFBP-3 blood concentration is of particular importance in the context of determining subject's responsiveness or sensitivity to therapy with GH or other similar agent which can induce both IGF-1 and IGFBP-3 generation. In general, an amount of growth hormone (GH) will be administering to the individual effective to stimulate IGF-1 production in a normal subject of the same age and gender as the individual. By "normal subject" is meant a subject that non-IGF-1 deficient. For example, in an IGF-1 production test (also referred to as a generation test) the amount of IGF-1 generated at baseline is calculated using the following formula, where IGFBP-3 concentration at baseline is used to calculate $t_{1/2}$(IGF-1):

$$\text{IGF-1}_{baseline\ production\ rate} = (\text{IGF-1}_{blood\ conc.})(\text{clearance rate IGF-1})).$$

The amount of IGF-1 generated or produced following increasing the blood GH concentrations is calculated using the following formula, where the IGFBP-3 concentration after GH (or other GH-inducing agent) administration is used to calculate IGF-1 clearance:

$$\text{IGF-1}_{post\text{-}therapy\ production\ rate} = (\text{IGF-1}_{post\text{-}therapy\ blood\ conc.})(\text{clearance rate IGF-1}).$$

The amount of IGF-1 generated or produced after GH administration can then be calculated qualitatively or quantitatively by, for example, using the following:

$$\text{IGF-1}_{therapy\ stimulated\ production\ rate} = \frac{\text{IGF-1}_{post\text{-}therapy\ production\ rate}}{\text{IGF-1}_{baseline\ production\ rate}}.$$

IGF-1$_{post\text{-}therapy\ production\ rate}$ will thus reflect whether a subject is responsive to therapy by production of IGF-1 in a meaningful way, e.g., whether the IGF-1 generated will be available to provide for a beneficial clinical effect. The ordinarily skilled artisan will appreciate that this IGF-1 generation test, adjusted for IGFBP-3 stimulation, can be conducted so as to take into account timing of therapy administration (e.g., time after GH administration), the dosage form used (e.g., bolus injection, sustained release formulation, etc.), as well as dose of agent administered, and can be repeated so as to take such factors into account. For example the GH concentration in blood can be used at the time that the IGF-1 and IGFBP-3 concentrations are measured to measure the degree of GH exposure that lead to the therapy stimulated IGF-1 production.

In another embodiment, the IGF-1 production at each of baseline and post-therapy are each used in the SDS calculator above to provide a baseline IGF-1 PR SDS and a post-therapy IGF-1 PR SDS, and a change in the IGF-1 PR SDS can be calculated.

The IGF-1$_{post-therapy\ stimulated\ production\ rate}$ can be used to determine an appropriate therapy for the subject. In some embodiments, where the stimulated rate of IGF-1 production is determined using IGF-1 PR SDS and therapy administered is GH, a change in IGF-1 PR SDS of at least +1.0, such as +2.0 or more, indicates the subject is responsive to GH therapy. However, where the change in IGF-1 PR SDS is less than +1.0, then the subject is not responsive to GH and therapy with IGF-1 can be indicated. Where the change in IGF-1 PR SDS is borderline, e.g., +0.5 to +1.5, then a combination therapy of, for example, GH and IGF-1 is indicated.

Computer Program Product

The above-described steps for transforming a blood IGF-1 concentration and a blood IGFBP-3 concentration to an IGF-1 PR SDS can be carried out by a human, e.g., manually performing each step. Alternatively, the above-described steps can be carried out by a computer program product. The present invention thus provides a computer program product including a computer readable storage medium having a computer program stored on it. The program can, when read by a computer, execute transformation of a blood IGF-1 concentration and a blood IGFBP-3 concentration to an IGF-1 PR SDS, e.g., calculates the IGF-1 PR SDS based on the blood IGF-1 concentration and a blood IGFBP-3 concentration. The computer program product has stored therein a computer program for performing the above-described algorithm on an IGF-1 concentration. In some embodiments, the program can also take IGF-2 blood concentrations into account in calculating the IGF-1 PR SDS.

Method and Device for Transforming an IGF-1 Blood Level to an IGF-1 Production Rate SDS A subject algorithm is applied to any given IGF-1 blood concentration and a blood IGFBP-3 concentration to an IGF-1 PR SDS, to determine whether the IGF-1 production rate is within the normal range (e.g., within +2 or −2 SD of the mean), or whether the IGF-1 production rate is below or above normal (e.g., more than −2 SD below the mean or +2 SD above the mean, respectively), in response to GH. The algorithms described herein can be applied manually (e.g., by an individual) or can be completely or partially performed by a computer. Alternatively, the algorithm can be applied to an IGF-1 concentration and an IGFBP-3 concentration by a computer. Accordingly, the present invention provides a computer program that carries out the transformation of an IGF-1 concentration and an IGFBP-3 concentration to an IGF-1 PR SDS.

Measuring IGF-1 Blood Levels

As discussed above, in some embodiments, the IGF-1 SDS is determined based on the IGF-1 concentration in a biological sample (e.g., blood). In other embodiments, the IGF-1 PR SDS is determined based on the amount of IGF-1 generated per unit time (e.g., μg/kg/hr). As discussed above, the amount of IGF-1 generated is determined based on the IGF-1 concentration and the IGFBP-3 concentration in a biological sample (e.g., blood). In yet other embodiments the "IGF-2 adjusted" IGF-1 PR SDS is determined based on the amount of IGF-1 generated per unit time (e.g., μg/kg/hr), adjusted for the level of IGF-2 in the blood.

Typically, the IGF-1 concentration or the amount of IGF-1 generated is measured in a biological sample (e.g., blood) following administration of GH, which stimulates production of IGF-1 under normal conditions. Where the individual is GH deficient (e.g., as in secondary IGFD), the level of IGF-1 is expected to increase in response to GH administration. Where the individual is GH resistant (e.g., as in primary IGFD), the level of IGF-1 does not rise to the level that would be expected in a subject who is GH deficient or in a normal individual.

In some embodiments, GH is administered by subcutaneous injection daily for a period of about seven days. IGF-1 concentration is measured at a time point(s) following administration of GH, e.g., at day 5. In other embodiments, GH is administered continuously, or substantially continuously, or in a form or manner so as to maintain a relatively constant level of blood GH. For example, in some embodiments, GH is administered using a depot. In other embodiments, a long-acting GH is administered.

Any known method can be used to measure IGF-1 concentration in a biological sample. In many embodiments, the assay is an immunological assay, e.g., an enzyme-linked immunosorbent assay (ELISA), a radioimmunoassay (RIA), immunoprecipitation, Western blotting, and the like, using one or more antibodies specific for IGF-1. In general, quantitation is accomplished by comparing the level of IGF-1 detected in the sample with the amount of IGF-1 present in a standard curve.

Non-limiting examples of assays for measuring IGF-1 include the following. Total IGF-1 in the blood can be determined by commercially available radioimmunoassays (Medgenix Diagnostics, Brussels, Belgium; IGF-1 RIA Kit, Nichols Institute, San Juan Capistrano, Calif.), e.g., after the extraction of the blood sample using acid ethanol to remove binding proteins which interfere with the detection of the IGF-1 by competing with anti-IGF-1 antibody.

Suitable antibodies specific for IGF-1 include polyclonal antibodies and monoclonal antibodies. In some embodiments, an IGF-1-specific antibody is one that distinguishes between IGF-1 and IGF-2. In other embodiments, an IGF-1-specific antibody is one that binds IGF-1 and cross-reacts with IGF-2, but not with other, non-IGF-1 and non-IGF-2, polypeptides.

Antibodies to IGF-1 are known in the art, and some such antibodies are commercially available. Any known antibody specific for IGF-1 is suitable for use in detecting an IGF-1 concentration in a biological sample.

As used herein, the term "determining" refers to both quantitative and qualitative determinations and as such, the term "determining" is used interchangeably herein with "assaying," "measuring," and the like. Thus, e.g., "determining" an IGF-1 concentration includes measuring an IGF-1 concentration.

Detection with a specific antibody is carried out using well-known methods. In general, the antibody is detectably labeled, either directly or indirectly. Direct labels include radioisotopes (e.g., $^{125}I$; $^{35}S$, and the like); enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Fluorescent proteins include, but are not limited to, a green fluorescent protein (GFP), e.g., a GFP derived from *Aequoria victoria* or a derivative thereof; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973; and the like.

Indirect labels include second antibodies specific for an IGF-1-specific antibody, wherein the second antibody is labeled as described above; and members of specific binding pairs, e.g., biotin-avidin, and the like.

Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

Antibodies are prepared in accordance with conventional ways, where the expressed polypeptide or protein is used as an immunogen, by itself or conjugated to known immunogenic carriers, e.g. KLH, HBsAg, other viral or eukaryotic proteins, or the like. Various adjuvants may be employed, with a series of injections, as appropriate. For monoclonal antibodies (MAbs), after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

In some embodiments, an IGF-1-specific antibody is bound, directly or via a linker, to an insoluble support. Insoluble supports are known in the art and include, but are not limited to, a bead (e.g, magnetic beads, polystyrene beads, and the like); a membrane (e.g., nylon, nitrocellulose, polyvinylpyrrolidone, and the like); a lateral flow test strip; a plastic surface (e.g., a surface of a multi-well plate, such as a polystyrene plate, a polypropylene plate, a polycarbonate plate, etc.) and the like. Insoluble supports that are suitable for use are described in a variety of publications, including, e.g., See, e.g., U.S. Pat. Nos. 5,569,608; 6,297,020; and 6,403,383.

Another method involves measuring the level of "free" or active IGF in blood. For example, one method is described in U.S. Pat. No. 5,198,340, herein expressly incorporated by reference in its entirety. An additional method is described in U.S. Pat. No. 6,251,865, issued Jun. 26, 2001, herein expressly incorporated by reference in its entirety, for detecting endogenous or exogenous IGF bound to an IGF binding protein or the amount of a compound that binds to an IGF binding protein and does not bind to a human IGF receptor bound to an IGF binding protein or detecting the level of unbound IGF in a biological fluid. This method comprises: (a) contacting the fluid with 1) a means for detecting the compound that is specific for the compound (such as a first antibody specific for epitopes on the compound) attached to a solid-phase carrier, such that in the presence of the compound the IGF binding sites remain available on the compound for binding to the IGF binding protein, thereby forming a complex between the means and the IGF binding protein; and 2) the compound for a period of time sufficient to saturate all available IGF binding sites on the IGF binding protein, thereby forming a saturated complex; (b) contacting the saturated complex with a detectably labeled second means which is specific for the IGF binding protein (such as a second antibody specific for epitopes on the IGFBP) which are available for binding when the compound is bound to the IGF binding protein; and (c) quantitatively analyzing the amount of the labeled means bound as a measure of the IGFBP in the biological fluid, and therefore as a measure of the amount of bound compound and IGF binding protein, bound IGF and IGF binding protein, or active IGF present in the fluid.

U.S. Pat. Nos. 5,593,844 and 5,210,017, herein expressly incorporated by reference in their entireties, disclose a ligand-mediated immunofunctional binding protein assay method that can be used to quantitate the amount of IGFBP in a liquid sample by the use of antibodies, where complex formation takes place between one of these binding proteins and the ligand that binds to it.

The quantitative technique mentioned above using antibodies, called the ligand-mediated immunofunctional method (LIFA), is described for determining the amount of IGFBP by contact with IGF in U.S. Pat. No. 5,593,844.

The following is a non-limiting example of an assay for IGF-1 blood concentration. A capture antibody specific for an epitope in the C-terminal 62-70 amino acids of IGF-1 is biotinylated for capture by streptavidin; and a second, detection antibody specific for an epitope in amino acids 1-23 and 42-61 is labeled with acridinium ester for detection. The biological sample being tested is acidified to separate soluble (free; e.g., not bound to an IGF-1 binding protein) from IGF-1 binding proteins. Individual acidified samples are contacted, in separate wells of a multi-well plate, with the biotinylated capture antibody in the presence of acridinium ester-labeled detection antibody, forming a reaction mixture. After the incubation period, streptavidin-coated magnetic particles (e.g., beads) are added to the reaction mixture. Free labeled antibody is separated from labeled antibody bound to the magnetic particles by aspiration and subsequent washing, while a strong magnetic force keeps the magnetic particles in the well. An acid hydrogen peroxide solution and a sodium hydroxide solution are added to the well to initiate the chemiluminescence reaction. See, e.g. Brabant et al. (2003), supra.

Measuring IGFBP-3 Levels

IGFBP-3 can be measured using commercially available immunoradiometric assays (IRMAs) for measuring IGFBP-1 and IGFBP-3 (Diagnostic System Laboratories Inc., Webster, Tex.). Any known method can be used to measure IGFBP-3 concentration in a biological sample (e.g., blood). In many embodiments, the assay is an immunological assay, e.g., an enzyme-linked immunosorbent assay (ELISA), a radioimmunoassay (RIA), immunoprecipitation, Western blotting, and the like, using one or more antibodies specific for IGFBP- 3. In general, quantitation is accomplished by comparing the level of IGFBP-3 detected in the sample with the amount of IGFBP-3 present in a standard curve. Antibodies and assay design are analogous to those described above for IGF-1 detection.

Measuring IGF-2 Levels

Any known method can be used to measure IGF-2 concentration in a biological sample (e.g., blood). In many embodiments, the assay is an immunological assay, e.g., an enzyme-linked immunosorbent assay (ELISA), a radioimmunoassay (RIA), immunoprecipitation, Western blotting, and the like, using one or more antibodies specific for IGF-2. In general, quantitation is accomplished by comparing the level of IGF-2 detected in the sample with the amount of IGF-2 present in a standard curve. Antibodies and assay design are analogous to those described above for IGF-1 detection.

Systems and Devices

The present invention provides a device for generating an IGF-1 SDS, based on a detected level of IGF-1 in a biological sample (e.g., blood). The detected level of IGF-1 may further be adjusted to account for the level of IGFBP-3 in the blood for generating an IGF-1 production rate SDS (IGF-1 PR SDS), and may also be further adjusted to account for the level of IGF-2 in the blood for generating an "IGF-2 adjusted" IGF-1 PR SDS.

The present invention also provides a device for generating a change in IGF-1 SDS, e.g., in response to administered GH, for example generating a change in an IGF-1 SDS based on a detected level of IGF-1 at baseline in a biological sample (e.g., blood) and a level of IGF-1 generated post stimulation, e.g., in response to administered GH. In some embodiments, the detected level of IGF-1 in the blood may be adjusted for the amount of IGFBP-3 in the blood prior to calculating a change generated in IGF-1 PR SDS. In other embodiments the detected level of IGF-1 in the blood may be adjusted for the amount of IGFBP-3 in the blood as well as the amount of IGF-2 in the blood, which adjusted IGF-1 blood concentration are used in calculating a change generated in an "IGF-2 adjusted" IGF-1 PR SDS.

In some embodiments, the device is a computing means, which may be part of a diagnostic system.

The present invention provides a diagnostic system for diagnosing primary and secondary insulin-like growth factor-1 deficiency (IGFD). The system generally comprises: a) a central computing environment; b) an input device, connected to the computing environment, to receive patient data, wherein the patient data include age, insulin-like growth factor-1 (IGF-1) blood concentration, IGF-2 blood concentration, and IGFBP-3 blood concentration; c) an output device, connected to the computing environment, to provide information to a user; and d) an algorithm executed by the central computing environment (e.g., a processor), where the algorithm is executed based on the data received by the input device, and wherein the algorithm transforms one or more of i) the IGF-1 blood concentration to an IGF-1 standard deviation score (SDS), ii) IGF-1 blood concentration and, based on the IGFBP-3 concentration, the IGF-1 clearance rate to an IGF-1 PR SDS, and iii) IGF-1 blood concentration, IGF-2 blood concentration, and IGF-1 clearance rate to an "IGF-2 adjusted" IGF-1 PR SDS. The SDS and/or PR SDS values are communicated to the output device. FIG. 2A depicts an exemplary embodiment of such a system.

Figure 2B:
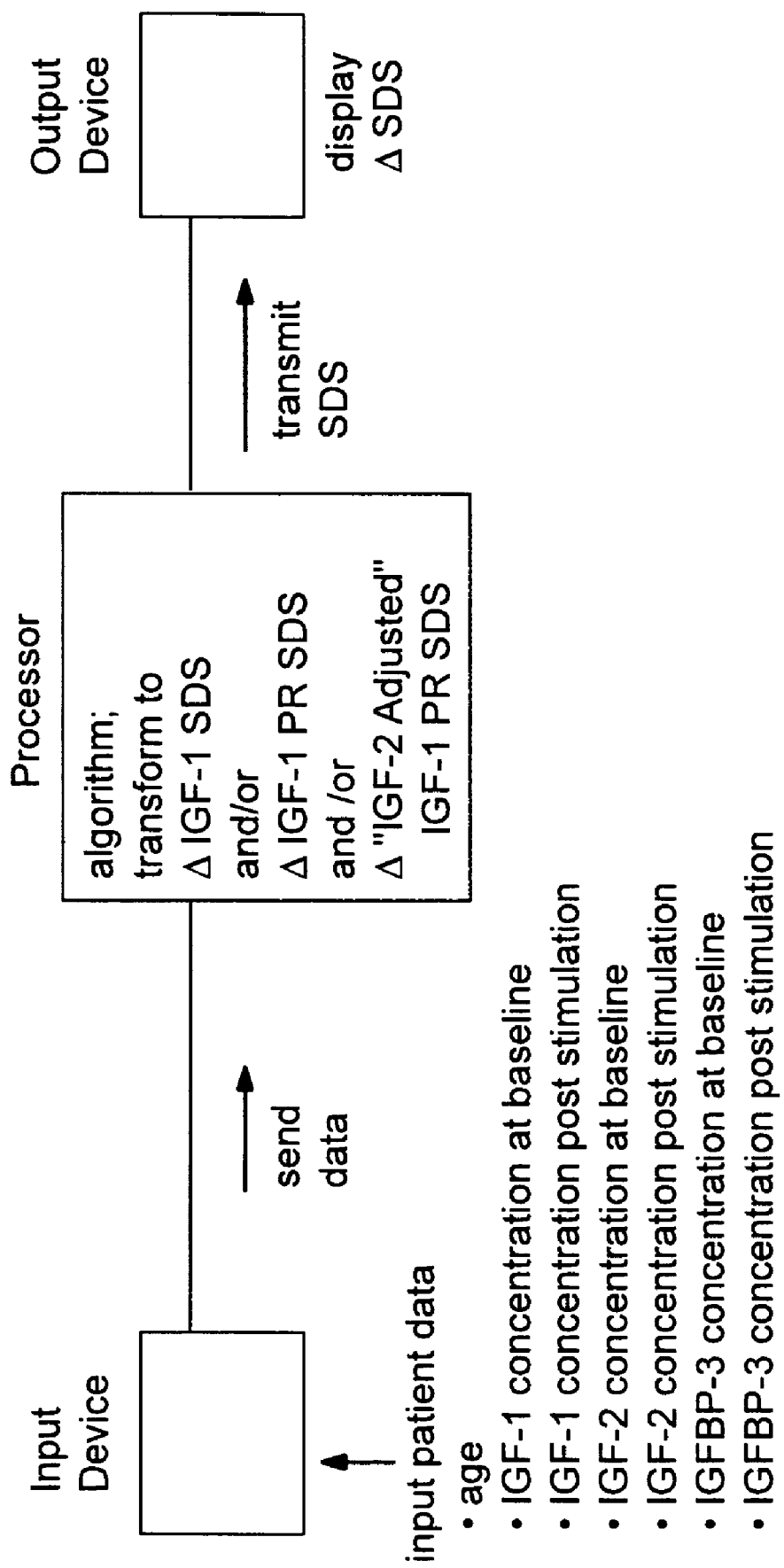

In some embodiments, diagnostic system will include generating a change in SDS, wherein the change IGF-1 blood concentration is determined based on an amount of IGF-1 at baseline and an amount of IGF-1 generated in response to stimulation, e.g., following administration of growth hormone. In such embodiments the patient data received by the input device will include blood concentrations of IGF-1, IGFBP-3, and/or IGF-2 at baseline (before stimulation) and after stimulation (e.g., after administration of a GH). In these embodiments, the processor further comprises an algorithm for computing the change in SDS based on an initial SDS at baseline and a second SDS following stimulation, by for example administration of GH. In some embodiments, the change in IGF-1 SDS is generated based on IGF-1 blood concentration unadjusted for either IGFBP-3 or IGF-2. In other embodiments, the change in IGF-1 PR SDS is generated based on the amount of IGF-1 and IGFBP-3 in the blood; In yet other embodiments, the change in "IGF-2 adjusted" IGF-1 PR SDS is generated based on an adjusted amount of IGF-1 taking into account the amount of IGFBP-3 in the blood as well as the amount of IGF-2 in the blood. FIG. 2B depicts an exemplary embodiment of such a system.

In some embodiments, the processor further comprises a computer program for making a diagnosis. The differential diagnostic program is configured such that, an SDS of at least about −2.0 SD below the normal mean, is indicative of an IGF-1 deficiency.

Figure 2C:
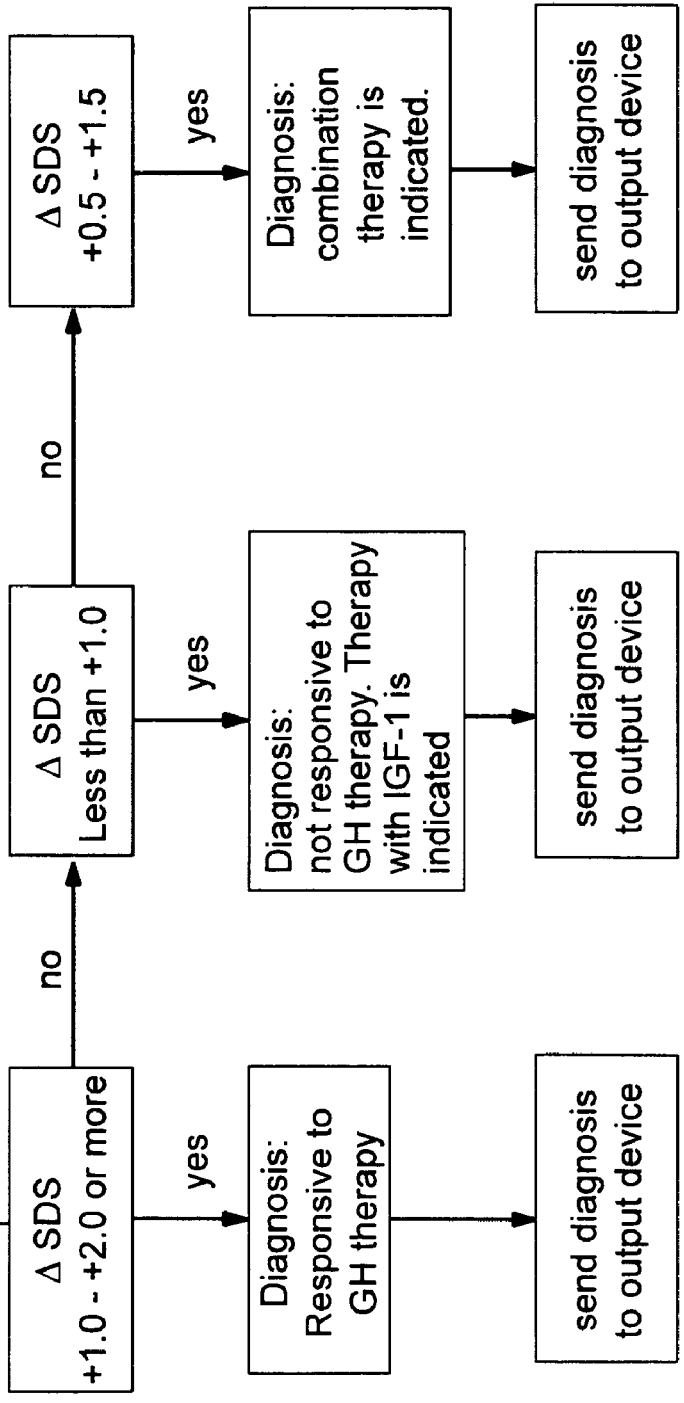

In the context of a test to determine a subject's responsiveness to GH (a generation or stimulation test), the differential diagnosis program is configured such that when GH administration results in a change in SDS or PR SDS of at least +1.0, such as +2.0 or more, the program indicates the subject is responsive to GH therapy. Further the program is configured such that when GH administration results in a change in SDS or PR SDS of less than +1.0, the program indicates the subject is not responsive to GH therapy and therapy with IGF-1 can be indicated. Where the change in IGF-1 SDS or IGF-1 PR SDS is borderline (e.g., +0.5 or +1.5), then a combination therapy of, for example, GH and IGF-1, is indicated. FIG. 2C depicts an exemplary embodiment of such a system.

Apparatus

The instant invention further provides a diagnostic apparatus. In some embodiments, the apparatus is a portable apparatus comprising a computer readable medium (e.g., a processor) for transforming one or more of i) the IGF-1 blood concentration to an IGF-1 standard deviation score (SDS), ii) IGF-1 blood concentration and, based on the IGFBP-3 concentration, the IGF-1 clearance rate to an IGF-1 PR SDS, and iii) IGF-1 blood concentration, IGF-2 blood concentration, and IGF-1 clearance rate to an "IGF-2 adjusted" IGF-1 PR SDS. In other embodiments, the diagnostic apparatus provides a change in the SDS in response to stimulation, e.g., prior to and following administration with a GH, as described in further detail above.

In some embodiments, a subject apparatus (e.g., a portable apparatus) comprises: a) a device for receiving and storing patient data, where the data include the age of the patient and insulin-like growth factor-1 (IGF-1) blood concentration in a biological sample from the patient, IGF-2 blood concentration, and IGFBP-3 blood concentration; b) a data output device; and c) an algorithm stored within the computer program product within the apparatus, which algorithm is executed to transform one or more of i) the IGF-1 blood concentration to an IGF-1 standard deviation score (SDS), ii) IGF-1 blood concentration and based on the IGFBP-3 concentration, the IGF-1 clearance rate to an IGF-1 PR SDS, and iii) IGF-1 blood concentration, IGF-2 blood concentration, and IGF-1 clearance rate to an "IGF-2 adjusted" IGF-1 PR SDS, which are transmitted to the data output device, where the output device displays the value(s) to a user. A subject apparatus will also typically include instructions for use in practicing a subject method. FIG. 3 depicts an exemplary embodiment of such an apparatus.

The data input device (also referred to as an operator input device) may be, e.g., a keyboard, a mouse, and the like. The processor has access to a memory, which may be any suitable device in which the processor can store and retrieve data, such as magnetic, optical, or solid state storage devices (including magnetic or optical disks or tape or RAM, or any other suitable device). The processor can include a general purpose digital microprocessor (such as is typically used in a programmable computer) suitably programmed to execute an algorithm as described above, or any hardware or software combination which will perform the required functions.

In some embodiments, the processor will be programmed to transform one or more of i) the IGF-1 blood concentration to an IGF-1 standard deviation score (SDS), ii) IGF-1 blood concentration and based on the IGFBP-3 blood concentration, the IGF-1 clearance rate to an IGF-1 PR SDS, and iii) IGF-1 blood concentration, IGF-2 blood concentration, and IGF-1 clearance rate to an "IGF-2 adjusted" IGF-1 production rate SDS. The corresponding value(s) will be transmitted to the output device, where it will be displayed. In some of these embodiments, the processor will be further programmed to determine, based on the calculated values, whether the diagnosis is primary IGFD, severe primary IGFD, or secondary IGFD. The calculated value(s) (SDS, PR SDS, IGF-2 adjusted PR SDS) and/or the diagnosis will be transmitted to the output device for display to a user.

In some embodiments, diagnostic system will include generating a change in SDS, wherein the change IGF-1 blood concentration is determined based on an amount of IGF-1 at baseline and an amount of IGF-1 generated in response to stimulation, e.g., following administration of growth hormone. In such embodiments the patient data received by the input device will include concentrations of IGF-1, IGFBP-3, and calculated IGF-1 clearance rate, and IGF-2 at baseline (before stimulation) and after stimulation (e.g., after administration of a GH). In these embodiments, the processor further comprises an algorithm for computing the change in SDS based on an initial SDS at baseline and a second SDS following stimulation, by for example administration of GH. In some embodiments, the change in IGF-1 SDS is generated based on an unadjusted amount IGF-1 in the blood. In other embodiments, the change in IGF-1 PR SDS is generated taking into account the amount of IGFBP-3 in the blood. In yet other embodiments, the change in "IGF-2 adjusted" IGF-1 PR SDS is generated based on an adjusted amount of IGF-1 taking into account the amount of IGFBP-3 in the blood and the IGF-1 clearance rate as well as the amount of IGF-2 in the blood. FIG. 2B depicts an exemplary embodiment of such a system.

In other embodiments, the processor will be programmed to generate a change in SDS, wherein the change in SDS is calculated based on the amount of IGF-1 produced in response to stimulation, for example, following administration of GH. The change in SDS is generated using a baseline (before stimulation) concentration of IGF-1 and a concentration following stimulation. In some embodiments, the change in IGF-1 SDS is generated based on an unadjusted amount IGF-1 in the blood. In other embodiments, the change in IGF-1 PR SDS is generated based on an adjusted amount of IGF-1 taking into account the amount of IGFBP-3 in the blood. In yet other embodiments, the change in "IGF-2 adjusted" IGF-1 PR SDS is generated based on an adjusted amount of IGF-1 taking into account the amount of IGFBP-3 in the blood as well as the amount of IGF-2 in the blood. The SDS will be transmitted to the output device, where it will be displayed. In further embodiments, the processor will be programmed to determine, based on the SDS, whether the diagnosis is primary IGFD, severe primary IGFD, or secondary IGFD. The SDS and/or the diagnosis will be transmitted to the output device for display to a user.

Figure 4:
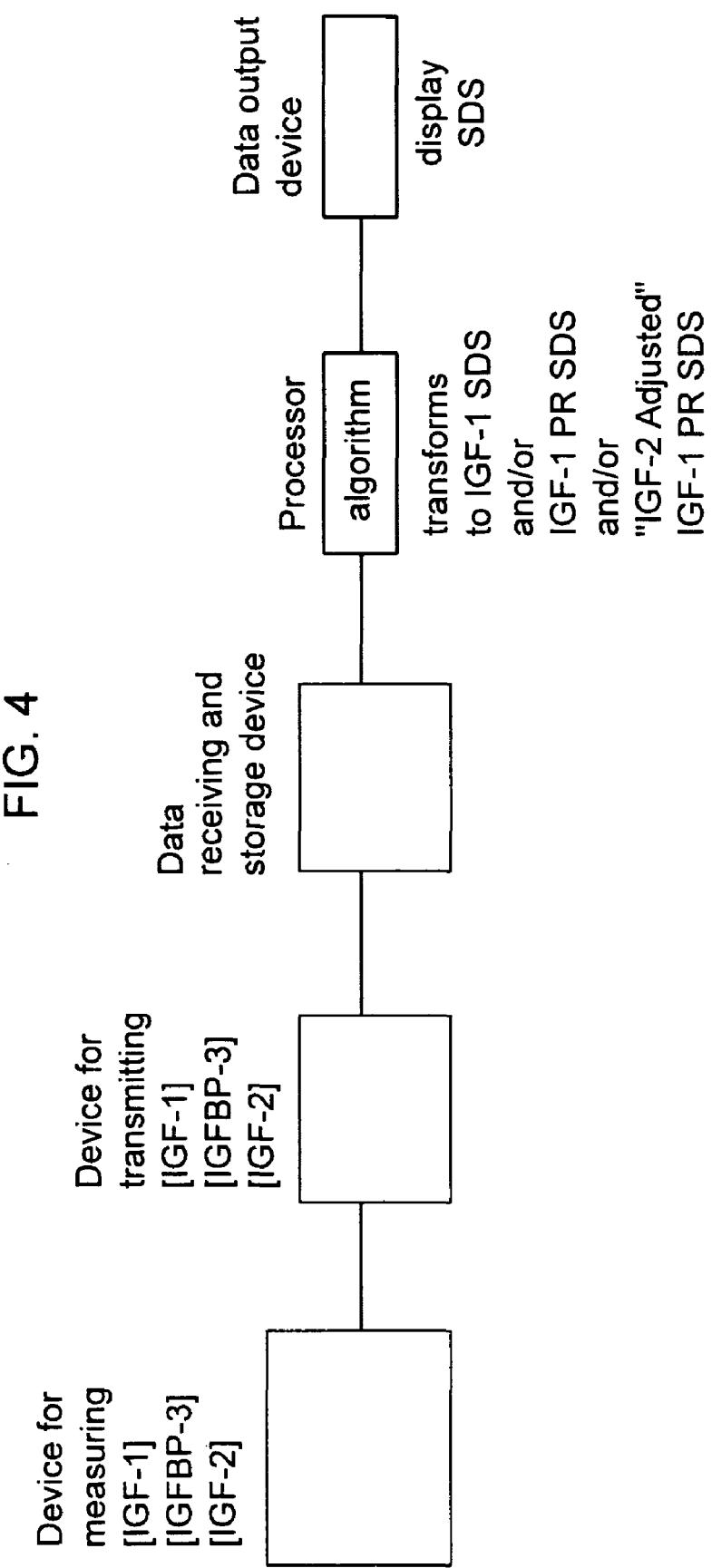
FIG. 4 depicts a further embodiment of a subject apparatus.

In other embodiments, a subject portable apparatus comprises: a) a device for measuring the blood concentration of IGF-1 and optionally one or both of IGF-2 and IGFBP-3 in the biological sample; b) a device for communicating (e.g., transmitting) the measured blood concentration(s) to the receiving and storage device; c) a device for receiving and storing patient data, where the data can include, for example, the age of the patient, the gender of the patient, and IGF-1, IGF-2, and IGFBP-3 concentrations in a biological sample from the patient; d) a data output device; and e) an algorithm stored within a computer program product within the apparatus, which algorithm is executed to transform the IGF-1 blood concentration, received from the receiving means, to an IGF-1 standard deviation score (SDS), and/or transform one or more of i) the IGF-1 blood concentration to an IGF-1 standard deviation score (SDS), ii) IGF-1 blood concentration and, based on the IGFBP-3 concentration, the IGF-1 clearance rate to an IGF-1 PR SDS, and iii) IGF-1 blood concentration, IGF-2 blood concentration, and IGF-1 clearance rate to an "IGF-2 adjusted" IGF-1 PR SDS. The value(s) calculated from this transformation is transmitted to the data output device, where the output device displays the calculated value(s) to a user. FIG. 4 depicts an exemplary embodiment of such an apparatus. Suitable devices for measuring the IGF-1, IGF-2, and IGFBP-3 concentrations include, but are not limited to, an enzyme-linked immunosorbent assay, a chemiluminescent assay, and a radioimmunoassay.

The device for detecting (e.g., measuring) an IGF-1 concentration in a biological sample includes at least one component for detecting a level of IGF-1 in a biological sample, as described above. As such, in certain embodiments, the device for detecting an IGF-1 concentration in a biological sample will include a detectably labeled antibody specific for IGF-1. In other embodiments, the device for detecting an IGF-1 concentration in a biological sample will include a detectably labeled antibody specific for IGF-1 and one or more reagents for developing the assay. In other embodiments, the device for detecting an IGF-1 concentration in a biological sample will include a detectably labeled antibody specific for IGF-1; and a capture antibody specific for IGF-1, which capture antibody does not interfere with the detectably labeled antibody for binding to IGF-1. In yet other embodiments, the device for detecting an IGF-1 concentration in a biological sample will further includes one or more additional components necessary for carrying out the IGF-1 concentration detection, such as sample preparation reagents, buffers, labels, and the like. As such, the device for detecting an IGF-1 concentration in a biological sample will in some embodiments include one or more containers such as vials or bottles, with each container containing a separate component for the assay, and reagents for carrying out a determination of IGF-1 concentration in a biological sample, e.g., an ELISA, an RIA, and the like. The device for detecting an IGF-1 concentration in a biological sample will in some embodiments also include one or more of a protease inhibitor(s); a wash medium/media; an enzyme substrate; one or more reagents for generating a labeled sample such as a detectably labeled secondary antibody; negative and positive controls; and written instructions for using the array assay devices for carrying out an array based assay.

In some embodiments, the device for detecting (e.g., measuring) an IGFBP-3 concentration in a biological sample includes at least one component for detecting a level of IGFBP-3 in a biological sample, as described above. As such, in certain embodiments, the device for detecting an IGFBP-3 concentration in a biological sample will include a detectably labeled antibody specific for IGFBP-3. In other embodiments, the device for detecting an IGFBP-3 concentration in a biological sample will include a detectably labeled antibody specific for IGFBP-3 and one or more reagents for developing the assay. In other embodiments, the device for detecting an IGFBP-3 concentration in a biological sample will include a detectably labeled antibody specific for IGFBP-3; and a capture antibody specific for IGFBP-3, which capture antibody does not interfere with the detectably labeled antibody for binding to IGFBP-3.

In yet other embodiments, the device for detecting an IGFBP-3 concentration in a biological sample will further includes one or more additional components necessary for carrying out the IGFBP-3 concentration detection, such as sample preparation reagents, buffers, labels, and the like. As such, the device for detecting an IGFBP-3 concentration in a biological sample will in some embodiments include one or more containers such as vials or bottles, with each container containing a separate component for the assay, and reagents for carrying out a determination of IGFBP-3 concentration in a biological sample, e.g., an ELISA, an RIA, and the like. The device for detecting an IGFBP-3 concentration in a biological sample will in some embodiments also include one or more of a protease inhibitor(s); a wash medium/media; an enzyme substrate; one or more reagents for generating a labeled sample such as a detectably labeled secondary antibody; negative and positive controls; and written instructions for using the array assay devices for carrying out an array based assay.

In other embodiments, the device for detecting (e.g., measuring) an IGF-2 concentration in a biological sample includes at least one component for detecting a level of IGF-2 in a biological sample, as described above. As such, in certain embodiments, the device for detecting an IGF-2 concentration in a biological sample will include a detectably labeled antibody specific for IGF-2. In other embodiments, the device for detecting an IGF-2 concentration in a biological sample will include a detectably labeled antibody specific for IGF-2 and one or more reagents for developing the assay. In other embodiments, the device for detecting an IGF-2 concentration in a biological sample will include a detectably labeled antibody specific for IGF-2; and a capture antibody specific for IGF-2, which capture antibody does not interfere with the detectably labeled antibody for binding to IGF-2.

In yet other embodiments, the device for detecting an IGF-2 concentration in a biological sample will further includes one or more additional components necessary for carrying out the IGF-2 concentration detection, such as sample preparation reagents, buffers, labels, and the like. As such, the device for detecting an IGF-2 concentration in a biological sample will in some embodiments include one or more containers such as vials or bottles, with each container containing a separate component for the assay, and reagents for carrying out a determination of IGF-2 concentration in a biological sample, e.g., an ELISA, an RIA, and the like. The device for detecting an IGF-2 concentration in a biological sample will in some embodiments also include one or more of a protease inhibitor(s); a wash medium/media; an enzyme substrate; one or more reagents for generating a labeled sample such as a detectably labeled secondary antibody; negative and positive controls; and written instructions for using the array assay devices for carrying out an array based assay.

In general, a subject apparatus will include a computer readable medium including programming for transforming one or more of i) the IGF-1 blood concentration to an IGF-1 standard deviation score (SDS), ii) IGF-1 blood concentration and, based on the IGFBP-3 concentration, the IGF-1 clearance rate to an IGF-1 PR SDS, and iii) IGF-1 blood concentration, IGF-2 blood concentration, and IGF-1 clearance rate to an "IGF-2 adjusted" IGF-1 PR SDS, as discussed above, and instructions for use. An IGF-1 SDS algorithm according to the present invention can be recorded on computer readable media, e.g., any medium that can be read and accessed directly or indirectly by a computer. Such media include, but are not limited to: magnetic tape; optical storage such as compact disc-read only memory (CD-ROM) and digital versatile disk (DVD); electrical storage media such as random access memory (RAM) and read-only memory (ROM); and hybrids of these categories such as magnetic/optical storage media. One of skill in the art can readily appreciate how any of the presently known computer readable media can be used to create a manufacture that includes a recording of the present programming/algorithms for carrying out the above-described methodology. In certain embodiments, the programming is further characterized in that it provides a user interface, where the user interface presents to a user the option of selecting among one or more different, including multiple different, criteria, e.g., age of individual, etc. The instructions may include installation or setup directions. The instructions may include directions for use of the invention.

In addition, a subject apparatus will typically include instructions for using the apparatus to carry out a subject method. The instructions of the above-described apparatus are generally recorded on a suitable recording medium. For example, the instructions may be printed on a substrate, such as paper or plastic, etc. As such, the instructions may be present in the apparatus as a package insert, or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the apparatus, but means for obtaining the instructions from a remote source, e.g. via the Internet, are provided. An example of this embodiment is an apparatus that includes a web address where the instructions can be viewed and/or from which the instructions can be downloaded. Conversely, means may be provided for obtaining the subject programming from a remote source, such as by providing a web address. Still further, the apparatus may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

Diagnostic Methods

The present invention provides a method of diagnosing primary IGFD and secondary IGFD. The method generally involves at least one of i) determining an IGF-1 SDS for the individual, based on an IGF-1 concentration in a biological sample (e.g., blood) from the individual; ii) determining an IGF-1 PR SDS for the individual, based on IGF-1 and IGFBP-3 concentrations in a biological sample (e.g., blood) from the individual; and iii) determining an "IGF-2 adjusted"

IGF-1 PR SDS for the individual, based on IGF-1, IGF-2, and IGFBP-3 concentrations in a biological sample (e.g., blood) from the individual. IGF-1 SDS, IGF-1 PR SDS, and "IGF-2 adjusted" IGF-1 PR SDS are determined using an algorithm as described above. The method further include making a diagnosis of primary IGFD or secondary IGFD based on the IGF-1 SDS, IGF-1 PR SDS, and/or "IGF-2 adjusted" IGF-1 PR SDS.

In some embodiments, the method involves detecting a concentration of IGF-1 in a biological sample (e.g., blood) from an individual being tested; determining an IGF-1 SDS for the individual, based on the detected level IGF-1 concentration, where the IGF-1 SDS is determined using an algorithm as described above; and, based on the determined IGF-1 SDS value, making a diagnosis of primary IGFD or secondary IGFD.

In other embodiments, the method involves detecting a concentration of IGF-1 and an IGFBP-3 concentration in a biological sample (e.g., blood) from an individual being tested; determining an IGF-1 PR SDS for the individual, based on the detected level IGF-1 concentration and (based on the IGFBP-3 concentration) the IGF-1 clearance rate, where the IGF-1 PR SDS is determined using an algorithm as described above; and, based on the determined IGF-1 PR SDS value, making a diagnosis of primary IGFD or secondary IGFD.

In other embodiments, the method involves detecting a concentration of IGF-1, a concentration of IGF-2, and a concentration of IGFBP-3 in a biological sample (e.g., blood) from an individual being tested; determining an "IGF-2 Adjusted" IGF-1 PR SDS for the individual, based on the detected IGF-1, IGF-2, and IGFBP-3 concentrations, where the "IGF-2 Adjusted" IGF-1 PR SDS is determined using an algorithm as described above; and, based on the determined "IGF-2 Adjusted" IGF-1 PR SDS value, making a diagnosis of primary IGFD or secondary IGFD.

In one embodiment, a diagnosis of IGF-1 deficiency is made where the subject has an IGF-1 blood concentration that is at least −1.0, −1.5, −2.0, −2.5, −3.0 or more SD below the normal mean (where normal is generally defined as having an IGF-1 blood concentration in the range of from above −2.0 to about +2.0 SD above the normal mean)

In yet other embodiments, the method involves determining a change in SDS for the individual, based on the amount of IGF-1 generated in a biological sample (e.g., blood) in response to administered GH, where the SDS is determined using an algorithm as described above; and, based on the determined IGF-1 SDS, making a diagnosis of primary IGFD or secondary IGFD and responsiveness to therapy, particularly where the therapy is one that causes generation of one or more of IGF-1, IGF-2 and IGFBP-3.

An IGF-1 SDS is determined at each of baseline and post-therapy, and a change in the IGF-1 SDS can be calculated. A change in IGF-1 SDS of at least +1.0, such as +2.0 or more, indicates the subject is responsive to GH therapy. However, where the change in IGF-1 SDS is less than +1.0, then the subject is not responsive to GH and therapy with IGF-1 can be indicated. Where the change in IGF-1 SDS is borderline, e.g., +0.5 to +1.5, then a combination therapy of, for example, GH and IGF-1 is indicated.

In some embodiments, the diagnosis is carried out manually by applying the above-described algorithm to the IGF-1 blood concentration or the amount of IGF-1 generated. In other embodiments, the diagnosis is carried out using a computer readable medium including programming for transforming an IGF-1 concentration to an IGF-1 SDS (an "IGF-1 SDS algorithm"), as discussed above.

In other embodiments, the diagnosis is carried out manually by applying the above-described algorithm to the IGF-1 and IGFBP-3 blood concentrations. In yet other embodiments, the diagnosis is carried out using a computer readable medium including programming for transforming IGF-1 and IGFBP-3 concentrations to an IGF-1 PR SDS as discussed above.

In yet other embodiments, the diagnosis is carried out manually by applying the above-described algorithm to the IGF-1, IGF-2, and IGFBP-3 blood concentrations. In yet other embodiments, the diagnosis is carried out using a computer readable medium including programming for transforming IGF-1, IGF-2, and IGFBP-3 concentrations to an "IGF-2 Adjusted" IGF-1 PR SDS as discussed above.

An IGF-1 SDS algorithm according to the present invention can be recorded on computer readable media, e.g., any medium that can be read and accessed directly or indirectly by a computer. Such media include, but are not limited to: magnetic tape; optical storage such as compact disc-read only memory (CD-ROM) and digital versatile disk (DVD); electrical storage media such as random access memory (RAM) and read-only memory (ROM); and hybrids of these categories such as magnetic/optical storage media. One of skill in the art can readily appreciate how any of the presently known computer readable media can be used to create a manufacture that includes a recording of the present programming/algorithms for carrying out the above-described methodology. In certain embodiments, the programming is further characterized in that it provides a user interface, where the user interface presents to a user the option of selecting among one or more different, including multiple different, criteria, e.g., age of individual, sex of individual, etc. The instructions may include installation or setup directions. The instructions may include directions for use of the invention.

Treatment Methods

The instant invention further provides a method of treating an individual having an IGFD disorder. The method generally involves determining whether an individual will be likely to respond to treatment with IGF-1, an agent that increases GH blood concentration, or a combination of IGF-1 and an agent that increases GH blood concentration; and administering an effective amount of IGF-1, an effective amount of an agent that increases GH blood concentration, or a combination of IGF-1 and an agent that increases GH blood concentration in amounts that in combination are effective to treat IGFD. In many embodiments, the determining step involves determining an IGF-1 SDS for the individual, as described above. In other embodiments, the IGF-1 blood concentration is determined taking into account the IGFBP-3 blood concentration so as to determine an IGFBP-3 adjusted IGF-1. In yet other embodiments, the IGF-1 blood concentration is determined taking into account the IGFBP-3 and IGF-2 blood concentrations so as to determine an IGF-2/IGFBP-3 adjusted IGF-1.

As such, a subject treatment method will in some embodiments comprise: a) determining an IGF-1 SDS based on an IGF-1 blood concentration in a biological sample from the individual and/or determining an IGF-1 PR SDS based on IGF-1 and IGFBP-3 blood concentrations in a biological sample from the individual and/or determining an "IGF-2 Adjusted" IGF-1 PR SDS based on IGF-1, IGF-2, and IGFBP-3 blood concentrations in a biological sample from the individual; b) based on the value determined in a), administering to the individual an effective amount of IGF-1, an IGF-1 analog, or an IGF-1 variant; administering to the individual an effective amount of an agent that increases the blood concentration of growth hormone (GH); or administering to the individual IGF-1, an IGF-1 analog, or an IGF-1 variant, and an agent that increases the blood concentration of GH in combined effective amounts to treat the IGFD disorder.

In one embodiment, subjects treated for IGF-1 deficiency are those having an IGF-1 blood concentration that is at least −1.0, −1.5, −2.0, −2.5, −3.0 or more SD below the normal mean (where normal is generally defined as having an IGF-1 blood concentration in the range from −2.0 to +2.0 SD below and above the normal mean)

As discussed above, therapy can also be selected according to the results of a GH stimulation test, which examines the amount of IGF-1 generated in a biological sample (e.g., blood) in response to administered GH, and uses the SDS or production rate SDS and corresponding algorithms described above. An IGF-1 SDS (or production rate SDS) is determined at each of baseline and post-therapy, and a change in the IGF-1 SDS can be calculated. A change in IGF-1 SDS (or production rate SDS) of at least +1.0, such as +2.0 or more, indicates the subject is responsive to GH therapy. However, where the change in IGF-1 SDS is (or PR SDS) less than +1.0, then the subject is not responsive to GH and therapy with IGF-1 can be indicated. Where the change in IGF-1 SDS (or production rate SDS) is borderline, e.g., +0.5 to +1.5, then a combination therapy of, for example, GH and IGF-1 is indicated.

Agents that Increase a Blood Level of Active IGF-1

In some embodiments, a subject treatment method involves administering to an individual an effective amount of an agent that increases a blood level of active IGF-1. As used herein, the term "IGF-1" includes any naturally-occurring or synthetic molecule that exhibits at least one biological activity of a naturally-occurring IGF-1 polypeptide, e.g., that bind to and function as agonists of an IGF-1 receptor. As used herein, the term "IGF-1" includes naturally-occurring IGF-1; synthetic IGF-1; an IGF-1 variant; a biologically active IGF-1 analog; a biologically active truncated IGF-1 polypeptide; and an IGF-1 agonist.

In another embodiment, IGF-1 agonist molecules that can effectively inhibit the interaction of IGF-1 with its binding proteins, allowing IGF-1 to bind to the IGF receptor for activity. See U.S. Pat. No. 6,251,865, issued Jun. 26, 2001, herein expressly incorporated by reference in its entirety. These IGF-1 agonist molecules can effectively displace IGF-1 bound to IGFBP. The IGF binding proteins (IGFBPs) are a family of at least six proteins (See Jones and Clemmons, 1995, Endocr Rev, 16: 3-34; Bach and Rechler, 1995, Diabetes Reviews, 3: 38-61), with other related proteins also possibly binding the IGFs. The IGFBPs bind IGF-1 and IGF-2 with varying affinities and specificities. See Jones and Clemmons, supra; Bach and Rechler, supra. For example, IGFBP-3 binds IGF-1 and IGF-2 with a similar affinity, whereas IGFBP-2 and IGFBP-6 bind IGF-2 with a much higher affinity than they bind IGF-1. See Bach and Rechler, supra; Oh et al., 1993, Endocrinology, 132, 1337-1344.

WO 94/04569 discloses a specific binding molecule, other than a natural IGFBP, that is capable of binding to IGF-1 and can enhance the biological activity of IGF-1.

IGF-1 point variants which bind to IGFBP-1 or IGFBP-3, thus inhibiting the interaction of endogenous IGF-1 with IGFBPs are described in U.S. Pat. No. 6,509,443.

IGF displacers that are peptides and discovered by phage display have also been described in, e.g., U.S. Pat. Nos. 6,420, 518; 6,251,865; and 6,121,416, all of which are hereby expressly incorporated by reference in their entireties.

Small molecule nonpeptide inhibitors can also release biologically active IGF-1 from the IGF-1/IGFBP-3 complex. For example, isoquinoline analogues have been found to be effective (See Chen C et al., 2001, J Med Chem 44:4001-10).

Additional compounds can be found using high throughput screening and the IGFBP Radioligand binding assay as described (see id.).

Other IGF-1 agonists include, but are not limited to; small molecules; synthetic drugs; peptides; polypeptides; proteins; nucleic acids (e.g., DNA and RNA nucleotides including, but not limited to, antisense nucleotide sequences, triple helices and nucleotide sequences encoding biologically active proteins, polypeptides or peptides); antibodies; synthetic or natural inorganic molecules; mimetic agents; and synthetic or natural organic molecules. WO 96/33216 describes a truncated variant having residues 1-69 of authentic IGF-1. European Patent No. 742,228 discloses two-chain IGF-1 superagonists which are derivatives of the naturally occurring single-chain IGF-1 having an abbreviated C domain. The IGF-1 analogs are of the formula: BC"A wherein B is the B domain of IGF-1 or a functional analog thereof, C is the C domain of IGF-1 or a functional analog thereof, n is the number of amino acids in the C domain and is from about 6 to about 12, and A is the A domain of IGF-1 or a functional analog thereof.

Suitable IGF-1 variants are those described in U.S. Pat. No. 5,077,276 issued Dec. 31, 1991; U.S. Pat. Nos. 5,164,370; 5,470,828; in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. An exemplary variant has the first three amino acids from the N-terminus deleted (variously designated as brain IGF, tIGF-1, des(1-3)-IGF-1, or des-IGF-1). Other compounds are the IGF-1 displacers compounds as described below, and in U.S. Pat. Nos. 6,121,416, 6,251,865, and 6,420,518.

IGF-1 variants can be designed that retain efficient binding to the type I IGF receptor, yet would have reduced binding to serum carrier proteins, e.g. IGFBPs. In one aspect, the design of these variants is based on the observation that insulin does not bind to serum carrier proteins. See U.S. Pat. No. 4,876, 242, issued Oct. 24, 1989, herein expressly incorporated by reference in its entirety. Evidence from synthetic, insulin-like two chain analogs suggests that amino acids of IGF-1 responsible for carrier protein binding are in the B region of IGF-1. Therefore a synthetic gene for human IGF-1 can be modified to encode an IGF-1 variant in which the first 16 amino acids of hIGF-1 are replaced by the first 17 amino acids of the B chain of human insulin. The synthetic gene is then placed in a yeast recombinant DNA expression system and the peptide analog which is produced by the modified yeast cells is extracted therefrom and purified. Additional modifications of the IGF-1 molecule have been carried out leading to additional analogs, all of which have substantial IGF-1 type I receptor binding and reduced binding to serum carrier proteins.

Other IGF-1 variants have been disclosed. For example, in the patent literature, WO 96/33216 describes a truncated variant having residues 1-69 of authentic IGF-1. EP 742,228 discloses two-chain IGF-1 superagonists which are derivatives of the naturally occurring single-chain IGF-1 having an abbreviated C domain. The IGF-1 analogs are of the formula: BC",A wherein B is the B domain of IGF-1 or a functional analog thereof, C is the C domain of IGF-1 or a functional analog thereof, n is the number of amino acids in the C domain and is from about 6 to about 12, and A is the A domain of IGF-1 or a functional analog thereof.

Additionally, Cascieri et al. (1988, Biochemistry 27:3229-3233) discloses four mutants of IGF-1, three of which have reduced affinity to the Type I IGF receptor. These mutants are:

(Phe$^{23}$, Phe$^{24}$, Tyr$^{25}$)IGF-1 (which is equipotent to human IGF-1 in its affinity to the Types 1 and 2 IGF and insulin receptors), (Leu$^{24}$)IGF-1 and (Ser$^{24}$)IGF-1 (which have a lower affinity than IGF-1 to the human placental Type I IGF receptor, the placental insulin receptor, and the Type I IGF receptor of rat and mouse cells), and desoctapeptide (Leu$^{24}$)IGF-1 (in which the loss of aromaticity at position 24 is combined with the deletion of the carboxyl-terminal D region of hIGF-1, which has lower affinity than (Leu$^{24}$)IGF-1 for the Type I receptor and higher affinity for the insulin receptor). These four mutants have normal affinities for human serum binding proteins.

Bayne et al. (1988, J Biol Chem 264:11004-11008) discloses three structural analogs of IGF-1: (1-62)IGF-1, which lacks the carboxyl-terminal 8-amino-acid D region of IGF-1; (1-27,Gly$^4$,38-70)IGF-1, in which residues 28-37 of the C region of IGF-1 are replaced by a four-residue glycine bridge; and (1-27,Gly$^4$, 38-62) IGF-1, with a C region glycine replacement and a D region deletion. Peterkofsky et al. (1991, Endocrinology, 128: 1769-1779) discloses data using the Gly$^4$ mutant of Bayne et al., supra. U.S. Pat. No. 5,714,460 refers to using IGF-1 or a compound that increases the active concentration of IGF-1 to treat neural damage.

Cascieri et al. (1989, J Biol Chem, 264: 2199-2202) discloses three IGF-1 analogs in which specific residues in the A region of IGF-1 are replaced with the corresponding residues in the A chain of insulin. The analogs are: (Ile$^{41}$, Glu$^{45}$, Gln$^{46}$, Thr$^{49}$, Ser$^{50}$, Ile$^{51}$, Ser$^{53}$, Tyr$^{55}$, Gln$^{56}$)IGF-1, an A chain mutant in which residue 41 is changed from threonine to isoleucine and residues 42-56 of the A region are replaced; (Thr$^{49}$,Ser$^{50}$,Ile$^{51}$)IGF-1; and (Tyr$^{55}$, Gln$^{56}$)IGF-1.

IGF-1 point variants which bind to IGFBP-1 or IGFBP-3, this inhibiting the interaction of endogenous IGF-1 with IGFBPs are described in U.S. Pat. No. 6,509,443.

Agents that Increase a Blood Concentration of GH

In some embodiments, a subject treatment method involves administering to an individual an effective amount of an agent that increases a blood concentration of GH. Agents that increase the blood level of GH in an individual include, but are not limited to, GH, a GH releasing peptide (GHRP), a GH releasing factor (GHRF), a GH releasing hormone (GHRH), a GH secretagogue, and the like.

Growth-promoting agents for this purpose include, but are not limited to, GH secretagogues that promote the release of endogenous GH in mammals to increase concentrations of the IGF in the blood. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206,235. See also, e.g., WO 96/15148 published May 23, 1996. Other growth-promoting agents include GHRPs, GHRFs, GH and their analogs. For example, GHRPs are described in WO 95/17422 and WO 95/17423 both published Jun. 29, 1995; Bowers, J. Pediatr. Endocrinol., 6: 21-31 (1993); and Schoen et al., Annual Reports in Medicinal Chemistry, 28: 177-186 (1993. GHRFs and their analogs are described, for example, in WO 96/37514 published Nov. 28, 1996.

In some embodiments, a long-acting depot formulation of GH to achieve steady-state levels of GH in the blood is used. Any means of achieving steady-state levels of GH in the blood can be used. An exemplary form of a long-acting or depot hGH is the Nutropin Depot® [somatropin (rDNA origin) for injectable suspension, Genentech, South San Francisco, Calif.], a long-acting dosage form of recombinant human growth hormone (rhGH). Somatropin has 191 amino acid residues and a molecular weight of 22,125 daltons. The amino acid sequence of the product is identical to that of pituitary-derived human growth hormone. The protein is synthesized by a specific laboratory strain of *E. coli* as a precursor consisting of the rhGH molecule preceded by the secretion signal from an *E. coli* protein. This precursor is directed to the plasma membrane of the cell. The signal sequence is removed and the native protein is secreted into the periplasm so that the protein is folded appropriately as it is synthesized.

The Nutropin Depot formulation consists of micronized particles of rhGH embedded in biocompatible, biodegradable polylactide-coglycolide (PLG) microspheres. Nutropin Depot is packaged in vials as a sterile, white to off-white, preservative-free, free-flowing powder. Before administration, the powder is suspended in Diluent for Nutropin Depot (a sterile aqueous solution).

Each 13.5 mg 3 cc single-use vial of Nutropin Depot contains 13.5 mg somatropin, 1.2 mg zinc acetate, 0.8 mg zinc carbonate, and 68.9 mg PLG. Each 18 mg 3 cc single-use vial of Nutropin Depot contains 18 mg somatropin, 1.6 mg zinc acetate, 1.1 mg zinc carbonate, and 91.8 mg PLG. Each 22.5 mg 3 cc single-use vial of Nutropin Depot contains 22.5 mg somatropin, 2.0 mg zinc acetate, 1.4 mg zinc carbonate, and 114.8 mg PLG. Each dosage size contains an overage of rhGH microspheres to ensure delivery of labeled contents. Each 1.5 mL single-use vial of Diluent for Nutropin Depot contains 30 mg/mL carboxymethylcellulose sodium salt, 1 mg/mL polysorbate 20, 9 mg/mL sodium chloride, and sterile water for injection; pH 5.8-7.2.

Other long-acting formulations of GH include PEGylated forms, including PEGylation at cysteine residues as described by U.S. Pat. No. 6,608,183, herein incorporated by reference in its entirety; poly(D,L-lactic-co-glycolic acid) (PLGA) microencapsulation; and the like.

Stabilizing agents, such as polyoxyethylene-polyoxypropylene block copolymer non-ionic surfactants, taurocholic acids, and methylcellolose derivatives, may be added as described in U.S. Pat. No. 6,593,296. Formulations of GH useful in a subject treatment method also include GH contained within a polymeric matrix of a biocompatible polymer as described in U.S. Pat. Nos. 4,041,155, 5,842,927, 6,429, 296 and 6,500,448.

Combination Therapy

Combination therapy with IGF-1 and one or more other appropriate reagents, such as those that increase total IGF-1 in the blood or enhance the effect of the IGF-1, or increase the concentration of IGFBP-3 in the blood, is also part of this invention. In one embodiment, these additional reagents generally allow an excess of blood IGF-1 over the amount of IGFBPs in blood or the IGF-1 to be released from IGFBPs, and include growth-promoting agents.

Growth-promoting agents for this purpose include, but are not limited to, growth hormone (GH) its natural variants such as 20 k hGH, placental GH or other variant of hGH or molecules that activate the hGH receptor, GH secretagogues that promote the release of endogenous GH in mammals to increase concentrations of the IGF in the blood. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206, 235. See also, e.g., WO 96/15148 published May 23, 1996. Other growth-promoting agents include GHRPs, GHRHs, GH and their analogs. For example, GHRPs are described in WO 95/17422 and WO 95/17423 both published Jun. 29, 1995; Bowers, J, 1993, Pediatr Endocrinol, 6:21-31; and Schoen et al., 1993, Annual Reports in Medicinal Chemistry, 28: 177-186. GHRHs and their analogs are described, for example, in WO 96/37514 published Nov. 28, 1996.

The reagent can be co-administered sequentially or simultaneously with IGF-1, and may be administered in the same, higher, or a lower dose than if used alone depending on such factors as, for example, the type of reagent used, the purpose for which the reagent and compound are being used, and clinical considerations. In addition, other means of manipulating IGF status, such as regimens of diet or exercise, are also considered to be combination treatments as part of this invention.

In one embodiment, IGF-1 is appropriately administered together with GH, such as for example human native-sequence, mature GH with or without a methionine at its N-terminus, recombinant hGH, i.e., that produced by means of recombinant DNA technology, recombinant hGH (rhGH), methionyl human growth hormone (met-hGH) produced in E. coli, e.g., by the process described in U.S. Pat. No. 4,755,465 issued Jul. 5, 1988 and Goeddel et al., Nature, 282: 544 (1979). Formulations comprising IGF-1 and GH are further described in U.S. Pat. Nos. 5,374,620 and 5,597,802, incorporated herein by reference in their entirety.

As a general proposition, the total pharmaceutically effective amount of each of the IGF-1 and GH administered parenterally per dose will be in the range of about 1 µg/kg/day to about 100 mg/kg/day of patient body weight, although this will be subject to a great deal of therapeutic discretion. In certain embodiments, this dose is at least 0.1 mg/kg/day, including at least 1 mg/kg/day for each hormone. If given continuously, the IGF-1 and GH are each typically administered at a dose rate of about 1 µg/kg/hour to about 50 µg/kg/hour, either by 1 to 4 injections per day or by continuous subcutaneous infusions, for example, using a minipump.

In one particularly embodiment, the composition comprises IGF-1 and GH in a weight ratio of IGF-1:GH of between about 2:1 and 100:1 (w/w), about 0.05 mM to about 0.3 mM of an osmolyte, such as an inorganic salt and/or sugar alcohol, about 0.1 mg/ml to about 10 mg/ml of at least one stabilizer, about 1 mg/ml to about 5 mg/ml of a surfactant, and about 5 mM to about 100 mM of a buffer at about pH 5-6. In certain embodiments, the amounts of IGF-1 and GH in such a composition are about 2 mg/ml to about 20 mg/ml IGF-1 and about 0.2 mg/ml to about 10 mg/ml GH. In further embodiments, the weight ratio of IGF-1:GH is about 3:1 to 50:1, including about 3:1 to 30:1, such as about 3:1 to 25:1, and about 5:1 to 20:1.

In further embodiments, the composition containing both IGF-1 and GH is the following: about 7 mg/ml to about 10 mg/ml of IGF-1, about 0.2 mg/ml to about 1.5 mg/ml of GH at a weight ratio of IGF-1:GH of about 3:1 to 20:1, about 5 mg/ml to about 7 mg/ml of sodium chloride, about 0.1 mg/ml to about 3 mg/ml of phenol and/or about 6 mg/ml to about 10 mg/ml of benzyl alcohol, about 1 mg/ml to about 3 mg/ml of polysorbate, about 2.5 mg/ml to about 4 mg/ml of sodium acetate, and about 0.1 mg/ml to about 1 mg/ml of sodium citrate, pH about 5.4.

In another embodiment, IGF-1 is appropriately administered together with any one or more of its binding proteins, for example, IGFBP-1, IGFBP-2, IGFBP-3, IGFBP-4, IGFBP-5, or IGFBP-6. Without being bound by a mechanism, co-administration of IGF-1 and an IGFBP may provide a greater response than IGF-1 alone by increasing the half-life of IGF-1.

A binding protein suitable for use is IGFBP-3, which is described in U.S. Pat. No. 5,258,287 and by Martin and Baxter, 1986, J Biol Chem, 261: 8754-8760. This glycosylated IGFBP-3 protein is an acid-stable component of about 53 Kd on a non-reducing SDS-PAGE gel of a 125-150 Kd glycoprotein complex found in human plasma that carries most of the endogenous IGFs and is also regulated by GH.

The administration of the IGF binding protein with IGF-1 may be accomplished by the method described in U.S. Pat. No. 5,187,151. Briefly, the IGF-1 and IGFBP are administered in effective amounts by subcutaneous bolus injection in a molar ratio of from about 0.5:1 to about 3:1, including about 0.75:1 to about 2:1, such as about 1:1.

Formulations, Dosages, and Routes of Administration

An active agent (e.g., IGF-1, an agent that increases blood GH levels, etc.) is administered to individuals in a formulation with a pharmaceutically acceptable excipient(s). The terms "active agent," "agent," and "therapeutic agent" are used interchangeably herein. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20$^{th}$ edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, the active agents may be administered to the host using any convenient means capable of resulting in the desired therapeutic effect. Thus, the agents can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, subcutaneous, intramuscular, transdermal, intratracheal, etc., administration. In some embodiments, two different routes of administration are used. For example, where a subject treatment method is a combination therapy, IGF-1 is administered by subcutaneous injection, while GH or a GH secretagogue is administered using a depot.

Subcutaneous administration of a therapeutic agent, e.g., IGF-1, an agent that increases blood GH levels, etc., can be accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a therapeutic agent to a patient through the port is referred to herein as "a subcutaneous injection port delivery system." In some embodiments, subcutaneous administration is achieved by a combination of devices, e.g., bolus delivery by needle and syringe, followed by delivery using a continuous delivery system.

An active agent (e.g., IGF-1, an agent that increases blood GH levels, etc.) may be administered to the mammal by any suitable technique, including oral, parenteral (e.g., intramuscular, intraperitoneal, intravenous, or subcutaneous injection or infusion, or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the peptide, the type of peptide being administered, and the particular disorder to be corrected. In some embodiments, the administration is by continuous infusion (using, e.g., slow-release devices or minipumps such as osmotic pumps or skin patches), or by injection (using, e.g., intravenous or subcutaneous means).

In some embodiments, a therapeutic agent, (e.g., IGF-1, an agent that increases blood GH levels, etc.), is delivered by a continuous delivery system. The terms "continuous delivery system," "controlled delivery system," and "controlled drug delivery device," are used interchangeably to refer to controlled drug delivery devices, and encompass pumps in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725, 852; 5,820,589; 5,643,207; 6,198,966; and the like. In general, the present methods of drug delivery can be accomplished using any of a variety of refillable, pump systems. Pumps provide consistent, controlled release over time. Typically, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are often used because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360, 019; 4,487,603; 4,360,019; 4,725,852, and the like. In general, the present methods of drug delivery can be accomplished using any of a variety of refillable, non-exchangeable pump systems. Pumps and other convective systems are often used due to their generally more consistent, controlled release over time. Osmotic pumps are in some embodiments used due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845, 770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, a therapeutic agent (e.g., IGF-1, an agent that increases blood GH levels, etc.) is delivered using an implantable drug delivery system, e.g., a system that is programmable to provide for administration of a therapeutic agent. Exemplary programmable, implantable systems include implantable infusion pumps. Exemplary implantable infusion pumps, or devices useful in connection with such pumps, are described in, for example, U.S. Pat. Nos. 4,350, 155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

In pharmaceutical dosage forms, the active agents may be administered in the form of their pharmaceutically acceptable salts, or they may also be used alone or in appropriate association, as well as in combination, with other pharmaceutically active compounds. The following methods and excipients are merely exemplary and are in no way limiting.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, an active agent (e.g., IGF-1, an agent that increases blood GH levels, etc.) is formulate alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives, and flavoring agents.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the agent(s) in a composition as a solution in sterile water, normal saline or another pharmaceutically acceptable carrier.

Dosages

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

The peptide to be used in the therapy will be formulated and dosed in a fashion consistent with good medical practice, taking into account the clinical condition of the individual patient (especially the side effects of treatment with the peptide), the site of delivery, the method of administration, the scheduling of administration, and other factors known to practitioners. The "effective amounts" of the peptide for purposes herein are thus determined by such considerations and must be amounts that result in bioavailability of the drugs to the mammal and the desired effect.

Given the above methods for determining dosages, in general, the amount of peptide that may be employed can be estimated, i.e., from about 10 .mu.g/kg/day to 200 .mu.g/kg/day might be used, based on kg of patient body weight, although, as noted above, this will be subject to a great deal of therapeutic discretion.

The peptide is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., Biopolymers, 22, 547-556 (1983), poly(2-hydroxyethyl methacrylate) (Langer et al., J. Biomed. Mater. Res., 15: 167-277 (1981), and Langer, Chem. Tech., 12: 98-105 (1982), ethylene vinyl acetate (Langer et al., supra) or poly-D-(−)-3-hydroxybutyric acid (EP 133,988). Sustained-release compositions also include a liposomally entrapped peptide. Liposomes containing the peptide are prepared by methods known per se: DE 3,218,121; Epstein et al., Proc. Natl. Acad. Sci. U.S.A., 82: 3688-3692 (1985); Hwang et al., Proc. Natl. Acad. Sci. U.S.A., 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated peptides having a longer life can also be employed, based on, e.g., the conjugate technology described in WO 95/32003 published Nov. 30, 1995.

For parenteral administration, in one embodiment, the peptide is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation typically does not include oxidizing agents and other peptides that are known to be deleterious to polypeptides.

Generally, the formulations are prepared by contacting the peptide uniformly and intimately with liquid carriers or finely divided solid carriers or both. Then, if necessary, the product is shaped into the desired formulation. In some embodiments, the carrier is a parenteral carrier, e.g., a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The peptide typically formulated in such vehicles at a pH of from or about 4.5 to 8. It will be understood that use of certain of the foregoing excipients, carriers, or stabilizers will result in the formation of salts of the peptide. The final preparation may be a stable liquid or lyophilized solid.

Typical formulations of the peptides as pharmaceutical compositions are discussed below. About 0.5 to 500 mg of the peptide or mixture of peptides, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

The peptide to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The peptide ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous solution of peptide, and the resulting mixture is lyophilized. The infusion solution is prepared by reconstituting the lyophilized peptide using bacteriostatic Water-for-Injection.

As discussed above the replacement dose of IGF-1 can be calculated for each patient based on the calculated amount of IGF-1 generated compared to the amount of IGF-1 generated for a normal individual of the same age and sex. This can be based on the difference between the microgram/kg/hr production rate in a normal individual and the microgram/kg/hr production rate in the patient. Replacement can be by once or twice daily subcutaneous injections of rhIGF-1 or by the administration of a slow release form of rhIGF-1 which could be administered once daily or less frequently.

Subjects Suitable for Treatment

Subjects suitable for treatment with a subject treatment method include individuals having an IGFD disorder or having short stature.

An IGFD disorder that can be treated with a subject method include short stature (in children); and metabolic disorders (e.g., in adults). In some embodiments, the subject will be a child whose long bone epiphyseal plates are open to that the subject can respond to a growth promoting therapy by increasing in height. In some embodiments, any of the above-mentioned individuals has a height standard deviation score for his or her age that is <−2. In some embodiments, any of the above-mentioned individuals has displayed a growth rate in the previous year that is <$50^{th}$ percentile for his or her age. Typically, no other reason for growth failure can be determined, e.g., other reasons for growth failure such as malnutrition, and the like, have been ruled out.

Other IGFD disorders that can be treated with a subject treatment method include, but are not limited to, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, undesirable symptoms associated with aging such as obesity and increased fat mass-to-lean ratios, immunological disorders such as immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., disease of the central nervous system including Alzheimer's disease, Parkinson's disease, or multiple sclerosis, and diseases of the peripheral nervous system and musculature, including peripheral neuropathy, multiple sclerosis, muscular dystrophy, or myotonic dystrophy, and catabolic states, associated with wasting caused by any condition, including, e.g., trauma or wounding or infection such as with a bacterium or human virus such as HIV, wounds, skin disorders, gut structure and function that need restoration, and so forth. Disorders of bone and cartilage growth in children, including short stature, and in children and adults disorders of cartilage and bone, including arthritis and osteoarthritis. The disorder being treated may be a combination of two or more of the above disorders. Specific disorders of interest targeted for treatment herein are diabetes and obesity, heart dysfunctions, kidney disorders, neurological disorders, bone disorders, whole body growth disorders, and immunological disorders.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

The IGF-1 SDS Generation Test: A Diagnostic Test to Identify GH-Responsive Patients and Patients Who are GH Non-Responsive Patients IGF-1 is the central mediator of statural growth, and IGF-1 deficiency (IGFD) is associated with short stature. Although IGFD can occur as a result of either GH insensitivity (primary IGFD) or GH deficiency (secondary IGFD), clinical phenotypes and serum IGF-1 levels are usually inadequate to distinguish between these two types of IGFD. Because serum IGF-1 is controlled by GH, the IGF-1 generation test should be well suited to discriminate between rhGH non-responsive patients with primary IGFD, and rhGH-responsive patients with secondary IGFD. Previously, Buckway et al. ((2001) *J Clin Endocrinol Metab.* 86(11):5176-83) concluded that overlap existed in IGF-1 concentrations in the generation test results between cohorts with primary IGFD (GHI) and secondary IGFD (GHD). The data were re-analyzed after first transforming all baseline and stimulated IGF-1 levels into standard deviation scores (SDS) using the SDS calculator described in Example 4.

Methods: Twenty-three subjects with classic GHD, 22 subjects with GHI homozygous for the E180 splice mutation of the GH receptor, 65 subjects heterozygous for the mutation, and 72 normal subjects were given, in random order, an IGF-1 generation test with low dose (25 μg/kg/d) and high dose (50 μg/kg/d) rhGH for seven days. Blood samples were taken on day 5 and 8 after starting rhGH. Receiver operating characteristic (ROC) analyses were used to assess the sensitivity and specificity of IGF-1 SD scores to discriminate GHD from the GH resistant patient groups.

Results: The ROC analysis showed complete discrimination (AUC value of 1.00) in primary IGFD patients compared to heterozygotes and normal subjects at day 8 after the high dose for all basal and rhGH-stimulated IGF-1 SDS. Table 1 shows ROC AUC values for discrimination between primary IGFD and secondary IGFD. Therefore Primary and secondary IGFD could be discriminated with maximal sensitivity (95.7%) and specificity (95.7%) being achieved using an IGF-1 SDS cut-off point of −2.5 using the high rhGH dose at both 5 and 8 days. It is therefore recommended that if an IGF-1 SDS score does not increase above −2.5 then a patient can be diagnosed with primary IGFD and should not therefore be treated with GH. In a similar manner it can be seen that if the IGF-1 SDS score does not change by a fixed amount a similar diagnosis can also be made.

TABLE 1

|  | Baseline | Low dose GH/day 5 | Low dose GH/day 8 | High dose GH/day 5 | High dose GH/day 8 |
| --- | --- | --- | --- | --- | --- |
| ROC AUC 2° vs 1° IGFD | 0.696 | 0.983 | 0.981 | 0.978 | 0.988 |

Conclusions: In IGFD children with short stature, the ROC analyses show near perfect discrimination between rhGH non-responsive patients with primary IGFD, and rhGH-responsive patients with secondary IGFD. In this example if the IGF-1 SDS score did not increase above −2.0 then the diagnosis of primary IGFD could be made. Moreover, where the IGF-1 SDS did not increase above −2.5, then the diagnosis of primary IGFD could be made with near certainty. The same conclusion could also be reached if the IGF-1 SDS did not increase by a specified change in the IGF-1 SDS score. The "IGF-1 SDS generation test" is a useful tool in determining those patients who should benefit from rhGH therapy, versus those who are unlikely to benefit from rhGH and for whom alternative therapies such as rhIGF-1 should be considered.

Example 2

A Pharmacokinetic Study to Assess the Parameters Controlling the Clearance of IGF-1 and the Dosing Requirements for Recombinant Human IGF-1 (rhIGF-1) in Patients, Especially Those with Primary IGF-1 Deficiency (IGFD)

In children with primary IGFD (defined as short stature and low blood IGF-1 concentrations in the presence of sufficient growth hormone secretion) physiologic replacement therapy with rhIGF-1 should correct IGF-1 concentrations to age- and gender-appropriate levels. Across the spectrum of IGFD, there is a direct correlation between serum IGF-1 and IGFBP-3 concentrations. IGFBP-3 is also inversely related to rhIGF-1 clearance (as discussed in detail below; data presented in FIG. 5A). Thus, rhIGF-1 dosing may need to be adjusted to prevailing IGFBP-3 levels. A single-dose rhIGF-1 PK study was conducted in subjects who had a wide range of IGF-1 and IGFBP-3 concentrations.

The objectives were to determine the pharmacokinetic (PK) parameters of a subcutaneous injection of recombinant human IGF-1 (rhIGF-1); to determine the dependence of the PK parameters on serum IGFBP-3; and to determine the safety of a single subcutaneous (sc) dose of rhIGF-1.

Methods: Twelve subjects with an extreme form of primary IGFD (Laron syndrome; LS, with severe IGFD, IGF-1 SDS <−3), 12 with moderate primary IGFD (IGF-1 SDS <−2, and normal GH secretion), and 12 normal subjects (IGF-1 SDS >−2) were randomized to receive 15, 30, 60 or 120 µg/kg rhIGF-1 as a single SC dose. Key inclusion criteria included: body mass of ≧10 kg; and age <5 years. PK parameters for each subject were estimated with WinNonlin (Pharsight Corp., Mountain View, Calif.). A model was developed that accounted for endogenous IGF-1 production (or generation) and the effect of IGFBP-3 on serum IGF-1 retention. Model simulations were used with individual subject PK parameters to estimate IGF-1 concentrations after two weeks of BID dosing. IGF-1 concentrations were transformed to IGF-1 SD scores using the SDS calculator, described in Example 4, specific for the IGF-1 assay.

Cohorts, doses, and numbers of subjects are shown in Table 2.

TABLE 2

| Cohort | 15 µg/kg | 30 µg/kg | 60 µg/kg | 120 µg/kg |
|---|---|---|---|---|
| Severe primary IGFD IGF-1 SDS < −3 | 3 | 3 | 3 | 3 |
| Primary IGFD IGF-1 SDS −3 to −2 | 3 | 3 | 3 | 3 |
| Normal IGF-1 IGF-1 SDS −2 to +2 | 3 | 3 | 3 | 3 |

Figure 6:
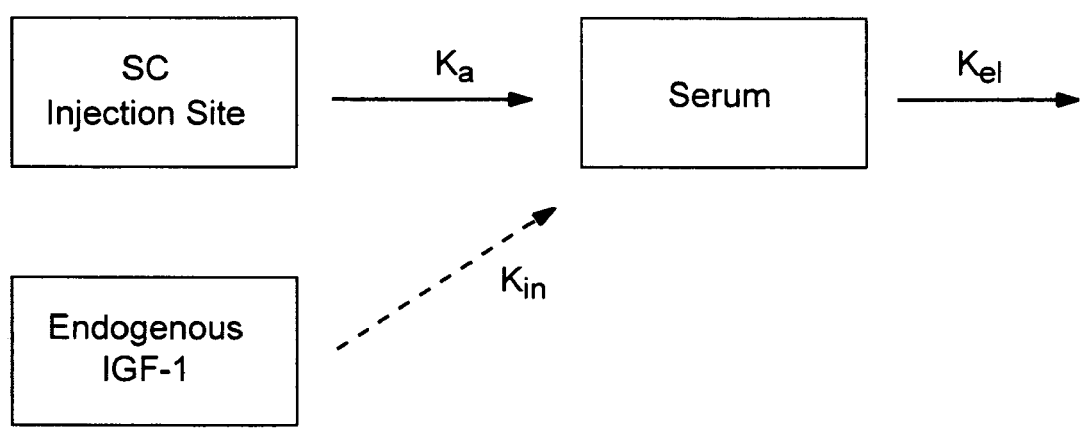
FIG. 6 is a schematic representation of an IGF-1 pharmacokinetic model.

Population PK Model Development. The one-compartment model with first-order SC absorption and elimination was used to characterize pharmacokinetics of IGF-1, as shown in FIG. 6. A zero-order input rate ($K_{in}$) was used to characterize the endogenous formation rate of IGF-1.

PK parameters, absorption rate constant ($K_a$), IGF-1 generation rate ($K_{in}$), volume of distribution ($V_d$) and clearance (CL) are modeled as follows:

$$K_a = \theta_1 \cdot \exp(BSV_1)$$

$$K_{in} = \theta_2 \cdot \exp(BSV_2)$$

$$CL = \theta_3 \cdot \exp(BSV_3)$$

$$V_d = \theta_4 \cdot \exp(BSV_4)$$

$$K_{el} = CL/V_d$$

where $\theta i$ are the fixed-effect parameters and $BSVi$ are between-subject random-effect parameters estimated by NONMEM. Exponential error models were employed for the between subject variability of Ka, Kin, CL, and Vd.

Results: The calculated PK parameter values by cohort and dose group are shown in Tables 3 and 4. IGF-1 AUC was directly related to dose (r=0.53, p=0.001) and IGFBP-3 level (r=0.44, p=0.008), where 'r' is a partial correlation coefficient reflecting adjustment for cohort. The log of IGFBP-3 was inversely related to both IGF-1 clearance (r=−0.91) and Kel (r=−0.92), both p<0.0001. Compared to severe primary IGFD subjects, primary IGFD subjects had higher AUC and lower Kel suggesting lower rhIGF-1 doses are possible as replacement therapy. Values for Kel are low, so simulations of two weeks of BID dosing predict an accumulation of IGF 1.

TABLE 3

Calculated AUCs by Cohort and Dose

| | 15 µg/kg | | | 30 µg/kg | | | 60 µg/kg | | | 120 µg/kg | | |
|---|---|---|---|---|---|---|---|---|---|---|---|---|
| Cohort | N | AUC | SD | N | AUC | SD | N | AUC | SD | N | AUC | SD |
| Severe Primary IGFD IGF-1 SDS < −3 | 3 | 717 | 250 | 3 | 944 | 461 | 3 | 2082 | 1111 | 3 | 2932 | 1475 |
| Primary IGFD IGF-1 SDS −3 to −2 | 3 | 4404 | 3033 | 3 | 5132 | 3544 | 3 | 4338 | 2634 | 3 | 9049 | 4567 |
| Normal IGF-1 IGF-1 SDS −2 to +2 | 3 | 4079 | 648 | 3 | 7160 | 2441 | 3 | 10256 | 4550 | 3 | 9549 | 2740 |

TABLE 4

PK Parameter Values

| Cohort | Vd (L/kg) | Clearance (mL/min/kg) | $K_{el}$ (hr$^{-1}$) | IGFBP-3 (µg/mL) | $K_{in}$ (µg/kg/hr) |
|---|---|---|---|---|---|
| Severe Primary IGFD IGF-1 SDS < −3 | 0.257 | 0.700 | 0.173 | 0.62 | 0.94 |
| Primary IGFD IGF-1 SDS −3 to −2 | 0.258 | 0.217 | 0.052 | 2.71 | 1.80 |
| Normal IGF-1 IGF-1 SDS −2 to +2 | 0.259 | 0.183 | 0.043 | 2.87 | 2.80 |

Figure 7:
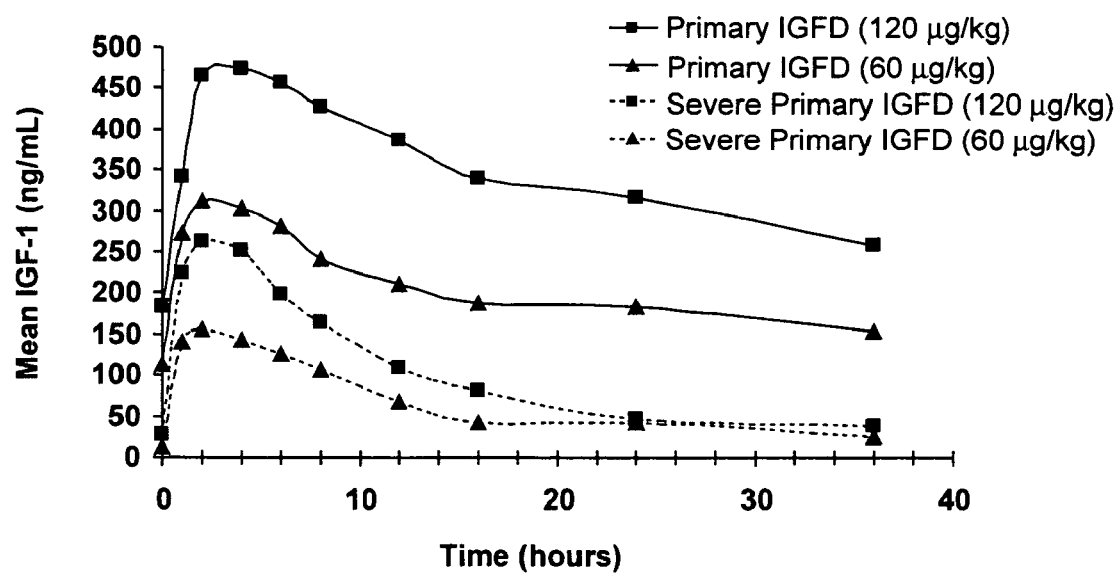
FIG. 7 is a graph depicting IGF-1 concentrations in subjects with primary IGFD after rhIGF-1 dose (60 μg/kg or 120 μg/kg).
Figure 8:
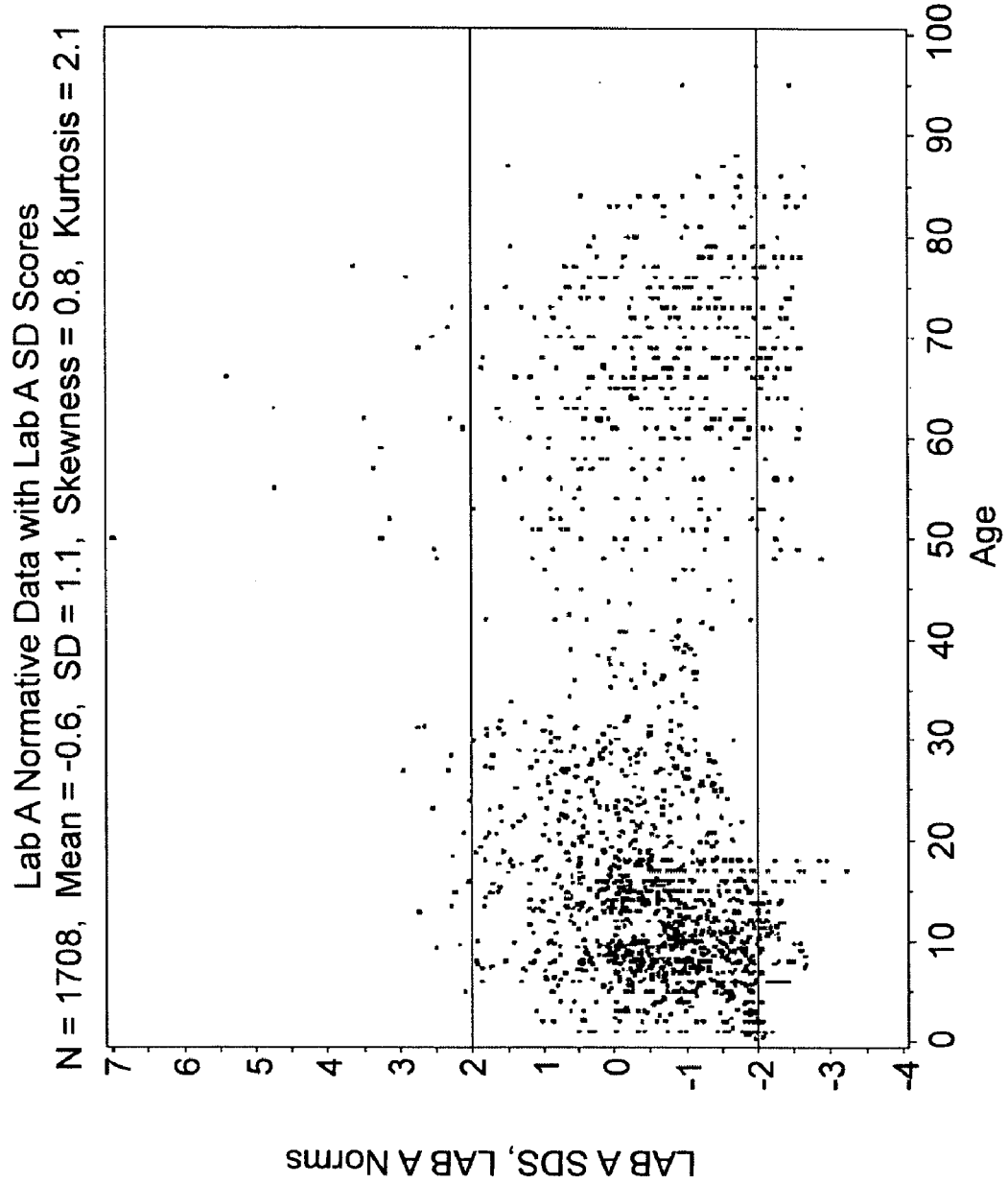
FIG. 8 depicts Laboratory A (Lab A) normative data and the Lab A SD score.
Figure 9:
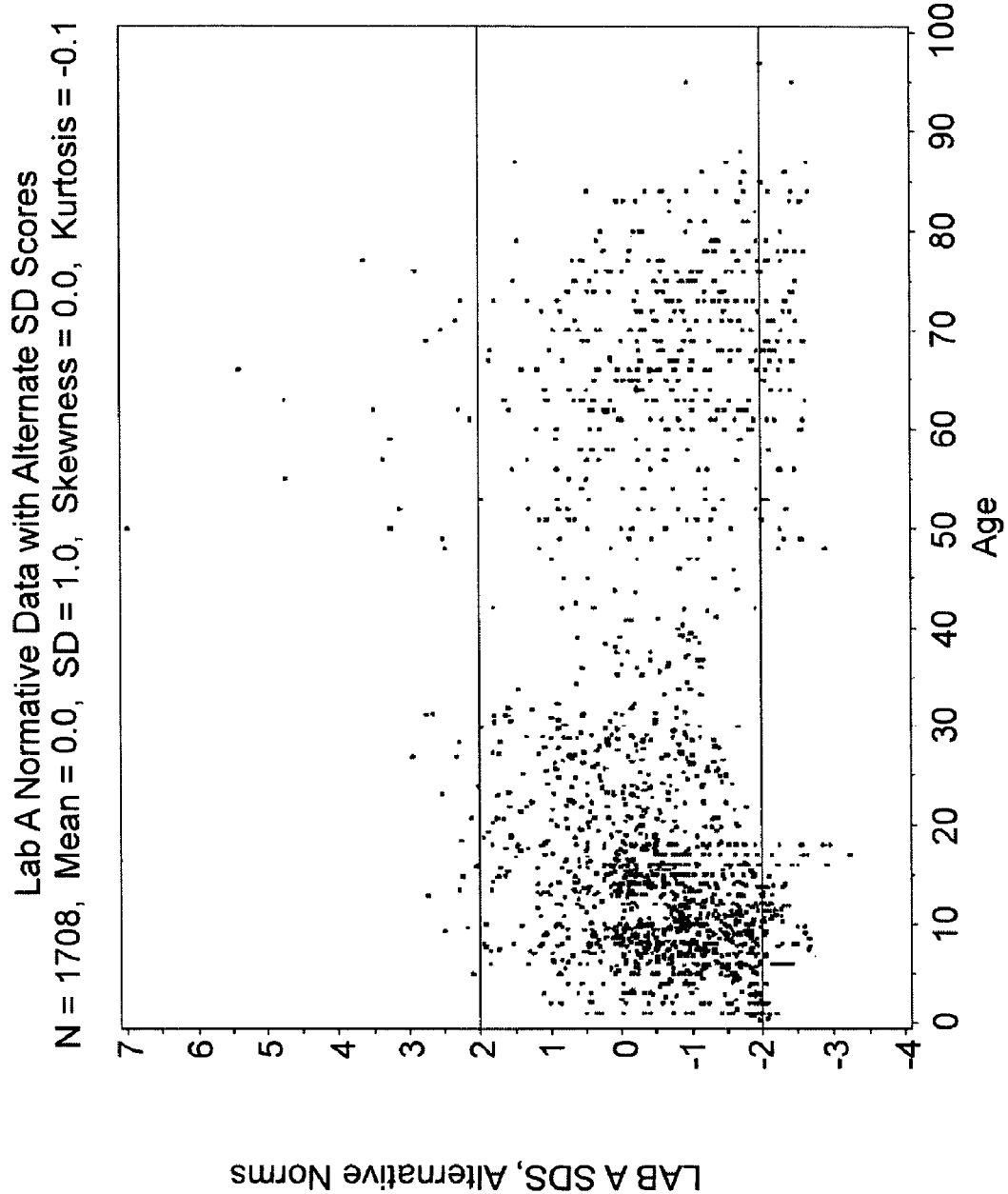
FIG. 9 depicts Lab A normative data and the IGF-1 SD score derived using a subject IGF-1 SDS calculator.
Figure 10:
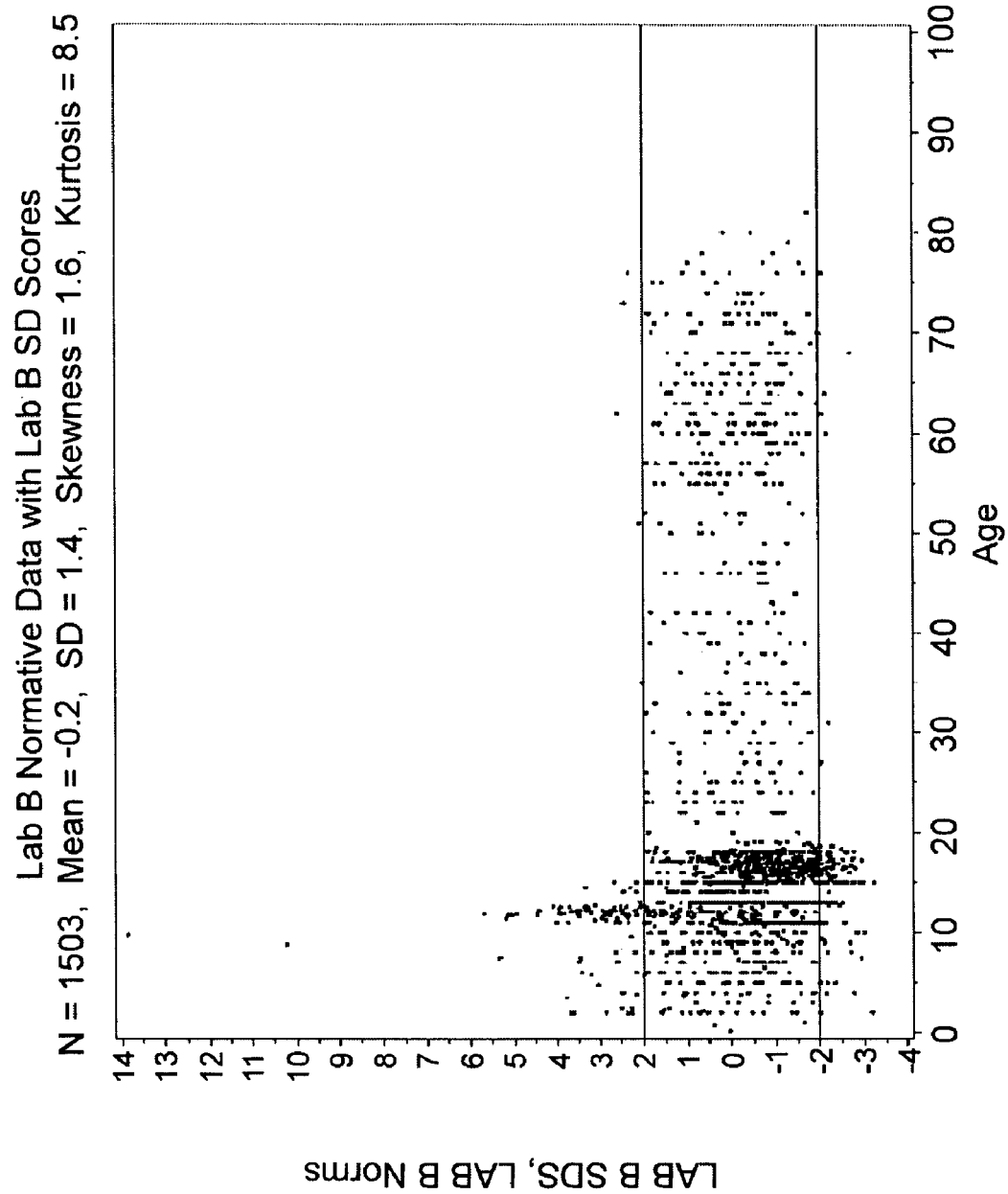
FIG. 10 depicts Laboratory B (Lab B) normative data and the Lab B SD score.
Figure 11:
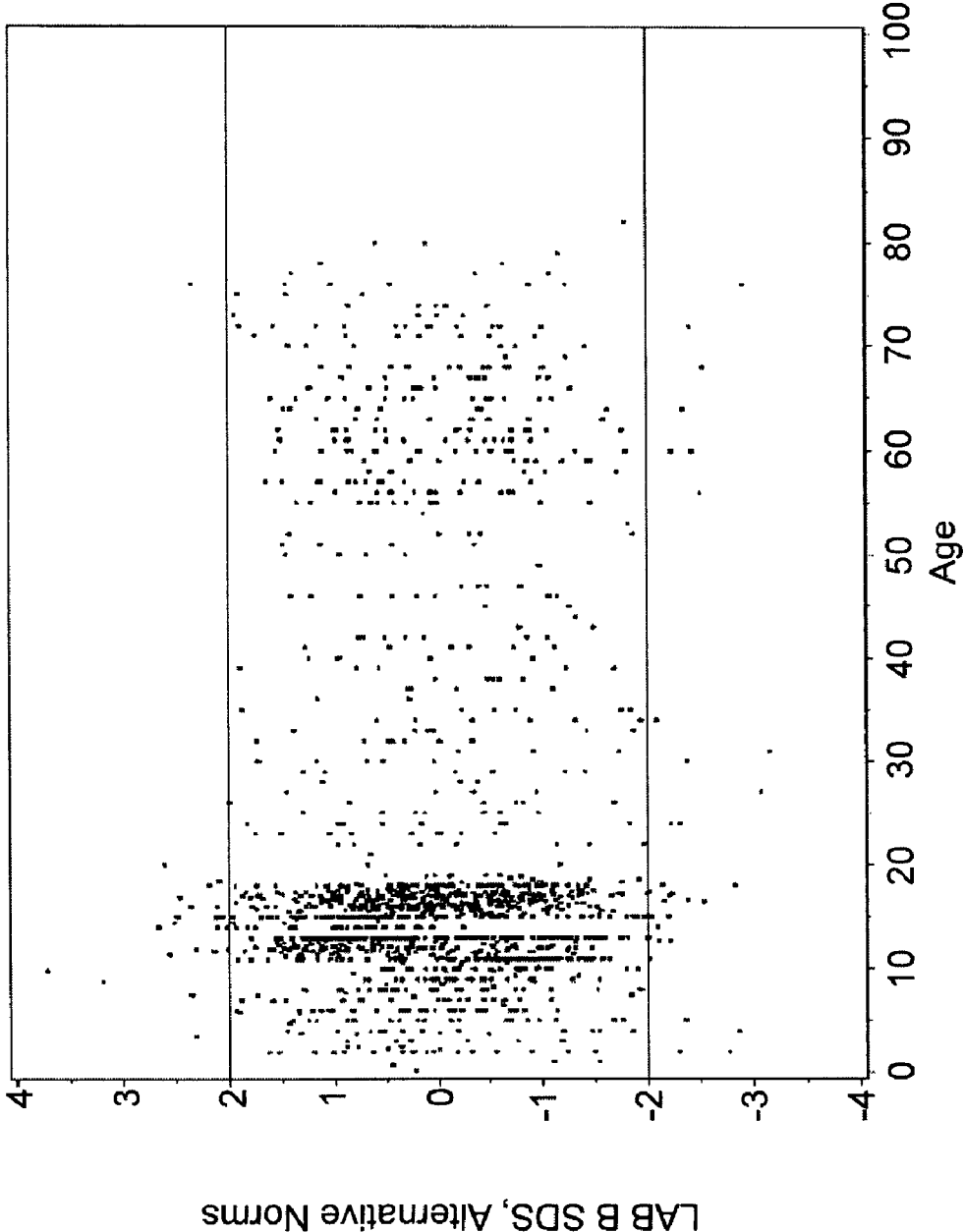
FIG. 11 depicts Lab B normative data and the IGF-1 SD score derived using a subject IGF-1 SDS calculator.

Conclusions: IGFBP-3 levels can aid in the selection of doses that produce physiologic excursions in IGF-1 in all subject groups. Based on time-dependent total serum IGF-1 concentration curves obtained at each dose (FIG. 7), the PK model also shows that children with IGFD may be candidates for once-daily dosing with rhIGF-1.

Example 3

Population Pharmacokinetic Analysis IGF-1 and IGFBP-3 Concentrations and Clearance 36 subjects including 19 females and 17 males were included in the study. All subjects were Hispanic and ranged in age from 9 to 25 years, with 11 subjects less than 18 years of age. The three IGF-1 cohorts were well balanced with respect to mean age. A higher proportion of females were enrolled in the Severe IGFD cohort (75%) compared with the Moderate IGFD (33%) or the IGF-1 Normal (50%) cohorts. Table 5 summarizes the key demographic and baseline characteristics for the 36 randomized subjects.

TABLE 5

Demographic and Baseline Characteristics: All Randomized Subjects

| Parameter | Severe IGFD (n = 12) | Moderate IGFD (n = 12) | IGF-1 Normal (n = 12) | Total (n = 36) |
|---|---|---|---|---|
| Gender, no. M/F | 3/9 | 8/4 | 6/6 | 17/19 |
| Age, Mean (yr) | 17.2 | 18.1 | 19.6 | 18.3 |
| (Range) | (12-22) | (9-25) | (11-25) | (9-25) |
| Race, no. Hispanic | 12 | 12 | 12 | 36 |
| Height, Mean (cm) | 118 | 154 | 161 | 144.4 |
| (Range) | (105-127) | (130-179) | (147-173) | (105-179) |
| Weight, Mean (kg) | 29.7 | 50.1 | 60.6 | 46.8 |
| (Range) | (20.0-36.5) | (25.2-72.0) | (39.8-77.8) | (20.0-77.8) |
| IGF-1, Mean (ng/mL) | 24.4 | 154.7 | 247.2 | 142.1 |
| (Range) | (<10-47) | (36-225) | (156-345) | (<10-345) |
| IGF-1 SD Score | −6.1 | −2.0 | −0.7 | −2.9 |
| (Range) | (−8.6- −3.7) | (−5.1- −0.4) | (−2.2- 0.9) | (−8.6- 0.9) |
| IGFBP-3, Mean (ng/mL) | 558 | 2400 | 2458 | 1806 |
| (Range) | (300-900) | (1100-3400) | (1700-3600) | (300-3600) |

TABLE 5-continued

Demographic and Baseline Characteristics: All Randomized Subjects

| Parameter | Severe IGFD (n = 12) | Moderate IGFD (n = 12) | IGF-1 Normal (n = 12) | Total (n = 36) |
|---|---|---|---|---|
| IGFBP-3 SD Score | −8.8 | −1.6 | −1.5 | −4.0 |
| (Range) | (−11.1- −6.1) | (−5.6- 0.5) | (−3.1- 0.6) | (−11.1- 0.6) |

Data source: Listing 16.2.3.

As expected, the mean height and body weight of subjects was considerably less in the Severe IGFD cohort compared with the other two cohorts. Height was between 4.8 SD and 7.6 SD below age- and gender-adjusted means among subjects in the Severe IGFD cohort. Consistent with study eligibility criteria, there was a progressive decline in baseline serum IGF-1 concentrations from the IGF-1 Normal to Severe IGFD cohorts, and the mean baseline IGFBP-3 level was less in the Severe IGFD cohort than in the Moderate IGDF or the IGF-1 Normal cohorts. No subject had clinically significant $T_4$ or TSH findings at screening. Few subjects had abnormal ECG findings at screening, none of which were considered clinically significant.

Mean total IGF-1 population pharmacokinetic parameters estimated by the NONMEM program are presented in Table 6; in this table, parameter precision is expressed as the coefficient of variance (% CV).

TABLE 6

Population Pharmacokinetics Parameters of Total IGF-1 in IGFD Subjects (Model 16)

| Parameter | Mean (% CV) | BSV (% CV) |
|---|---|---|
| $K_a$ (h-1) | 0.93 (11) | 46 (37) |
| $K_{in}$ in Severe IGFD, (µg/kg/h) | 0.95 (14) | 19 (97) |
| $K_{in}$ in Moderate IGFD, (µg/kg/h) | 1.81 (22) | Same as above |
| $K_{in}$ in IGF-1 Normal, (µg/kg/h) | 2.81 (18) | Same as above |
| Vd/F (L/kg)$^b$ | 0.258 (4) | 8.5 (72) |
| CL/F (L/h/kg)$^c$ | 0.0103 (18) | 23 (36) |
| Effect of IGFBP-3 on CL/F | −0.83 (17) | — |
| Effect of Dose on Vd/F | 0.33 (13) | — |

Residual error 9.0%.
Data source:
$^a$BSV = between-subject variability.
$^b$Estimate of Vd/F at 45 µg/kg dose of rhIGF.
$^c$Estimate of CL/F at 3 µg/mL IGFBP-3.

The potential effects of age, gender, IGFBP-3 level, and rhIGF-1 dose covariates on pharmacokinetics of serum IGF-1 after a single SC dose of rhIGF-1 were evaluated. As expected, the rate of formation of endogenous serum IGF-1 was considerably different among the three cohorts of subjects, and was inversely related to level of IGFD. The rates of formation of serum IGF-1 were 0.95, 1.81, and 2.81 µg/kg/h in the Severe IGFD, Moderate IGFD, and IGF-1 Normal cohorts, respectively. There was no significant effect of age on the formation rate of IGF-1, possibly due to the narrow range of ages among subjects participating in this study. Males and females were almost equally represented in the overall study population (17 males, 19 females). No any significant gender difference was found in pharmacokinetics of IGF-1.

Clearance of IGF-1 was 0.0103 L/h/kg (0.165 mL/min/kg) at 3 µg/mL IGFBP-3, and decreased with increasing IGFBP-3 level as shown in FIG. 3. The volume of distribution for IGF-1 increased somewhat with increasing rhIGF-1 dose (see FIG. 5A).

Figure 5B:
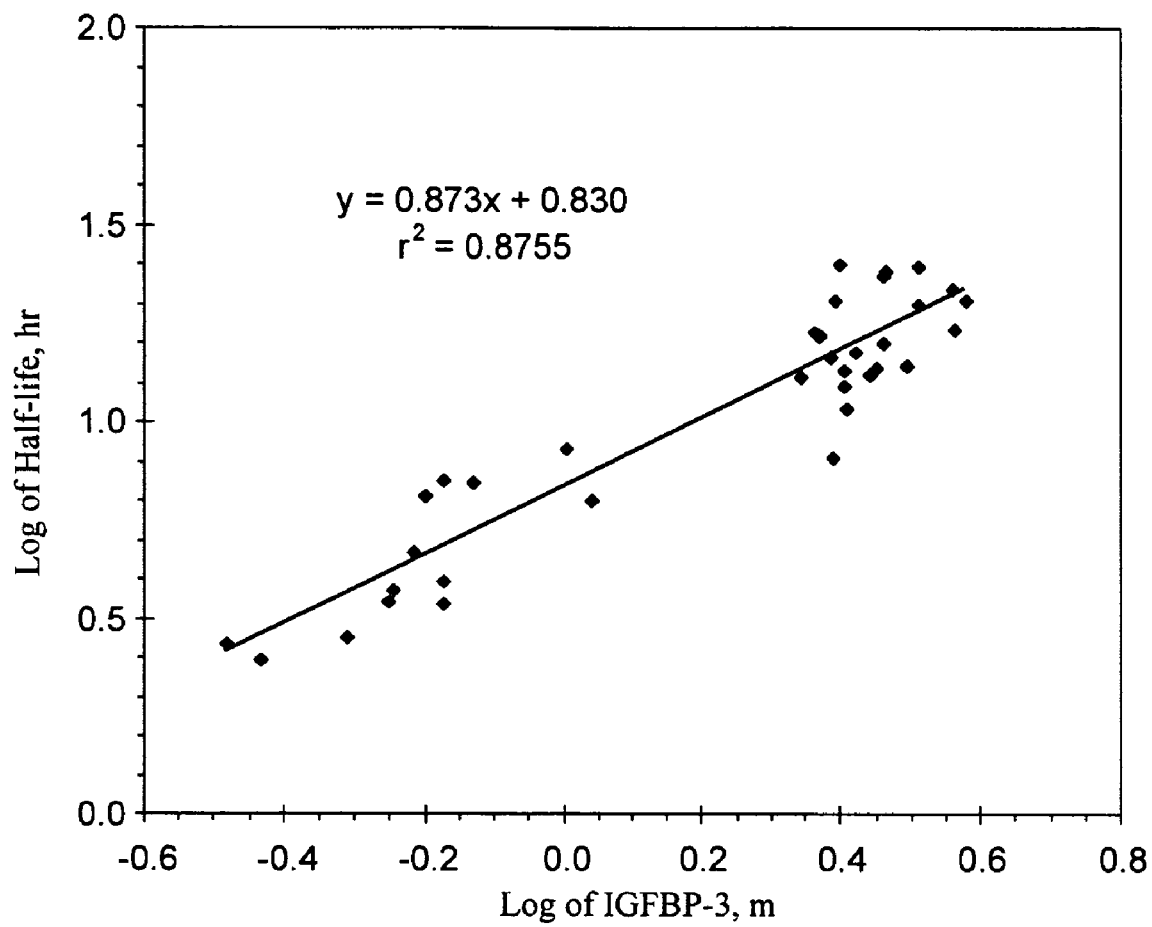
FIG. 5B is a graph of the relationship between IGFBP-3 and IGF-1 half-life and log-log scale. The solid line represents the model-predicted function.
Figure 5C:
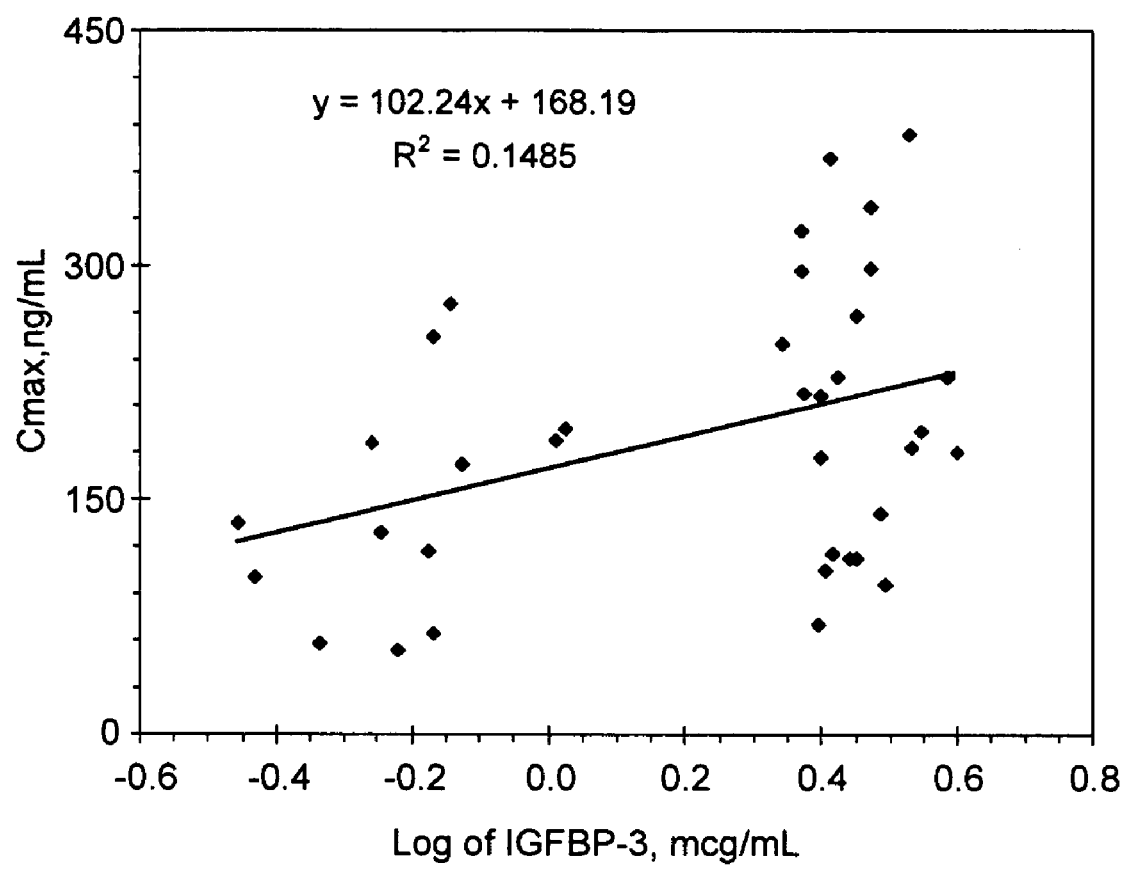
FIG. 5C is a graph of the relationship between IGFBP-3 and IGF-1 peak concentrations. The solid line represents the model-predicted function.

The effects of IGFBP-3 and rhIGF-1 dose were expressed as a power function using the equations in the example above. The log transformation in both axes linearized the relationship between IGFBP-3 and CL/F and the relationship between rhIGF-1 dose and Vd/F, respectively. Furthermore, the log of IGFBP-3 was inversely related to the log of IGF-1 half-life and IGF-1 $C_{max}$ as shown in FIGS. 5B and 5C, respectively.

Example 4

Calculation of Serum IGF-1 Standard Deviation Scores

IGF-1 levels vary with age and gender. Estimates of the mean and standard deviation (SD) for IGF-1 at a given age and gender can be used to calculate SD scores and establish a firm diagnosis of IGF-1 deficiency. Since IGF-1 values are not normally distributed, accurate estimation of mean and SD requires prior data transformation. The statistical distribution of SD scores across age and sex ideally has a mean of zero, a standard deviation of one, skewness of zero, and kurtosis of zero.

Methods: Normative IGF-1 values were obtained from four leading commercial labs. Plots of the distribution of SD scores computed using the norms and methods provided from the respective laboratories showed non-homogeneous variance and/or skewness. Opportunities for improvement in SD score formulas were observed after inspection of these plots. In order to obtain improved SD scores, seven steps were used for each assay and gender: (1) A power transformation (e.g., as discussed in Brabant et al. (2003) *Horm Res.* 60(2):53-60); Kuczmarski et al. (2002) *Vital Health Stat* 11(246):1-190); and Löfqvist et al. (2001) *J Clin Endocrinol Metab.* 86(12): 5870-6) was chosen to cope with the skewness in values for any age and gender. (2) A smooth mean curve was fit as a function of age through the transformed IGF-1 values using the "loess" procedure in SAS. (3) The mean absolute deviations from the smoothed mean were fit using loess, from which the standard deviation was derived for each age. (4) The SD score for each subject in the corresponding normative sample was computed as SDS=(power transformed IGF-1 value−smoothed mean for age)/smoothed standard deviation for age. (5) The resulting SD scores were plotted by age and the characteristics of these SD scores were evaluated by their overall mean, standard deviation, skewness, and kurtosis (which should all be 0) and by the Wilk-Shapiro test for fit to the normal distribution. (6) Steps 1-5 were repeated for several different power transformations and different levels of smoothing. (7) The power transformation resulting in SD scores with characteristics closest to the standard normal distribution was retained for the assay and gender in question.

Results: The distribution of SD scores for the four laboratories estimated using the original SDS and the SDS calculators derived from the power transformation described above are shown in FIGS. 8-11 and Tables 7 (original calculators) and 8 (new calculators).

TABLE 7

|  | Mean | SD | Skewness | Kurtosis |
|---|---|---|---|---|
| Lab A | −0.6 | 1.1 | 0.8 | 2.1 |
| Lab B | −0.2 | 1.4 | 1.6 | 8.5 |

TABLE 7-continued

|  | Mean | SD | Skewness | Kurtosis |
|---|---|---|---|---|
| Lab C | 0.0 | 1.0 | 0.1 | 0.6 |
| Lab D | 0.0 | 1.1 | −0.7 | 1.7 |

TABLE 8

|  | Mean | SD | Skewness | Kurtosis |
|---|---|---|---|---|
| Lab A | 0.0 | 1.0 | 0.0 | −0.1 |
| Lab B | 0.0 | 1.0 | −0.1 | −0.1 |
| Lab C | 0.0 | 1.0 | 0.0 | 0.5 |
| Lab D | −0.1 | 1.0 | 0.0 | 0.0 |

Conclusions: Power transformation of serum IGF-1 concentration leads to a valid procedure for the estimation of IGF-1 SD scores based on age- and gender-specific means and standard deviations.

Example 5

The IGF-1 Production Rate SDS Test: A Diagnostic Test to Identify rhGH-Responsive Patients and Patients Who are rhGH Non-Responsive Patients IGF-1 is the central mediator of statural growth, and IGF-1 deficiency (IGFD) is associated with short stature. Although IGFD can occur as a result of either GH insensitivity (primary IGFD) or GH deficiency (secondary IGFD), clinical phenotypes and serum IGF-1 levels are usually inadequate to distinguish between these two types of IGFD. Serum IGF-1 is controlled by GH and by IGFBP-3, so the IGF-1 production rate SDS test which takes account of the IGFBP-3 concentration, should be well suited to discriminate between rhGH non-responsive patients with primary IGFD, and rhGH-responsive patients with secondary IGFD. Previously, Buckway et al. ((2001) *J Clin Endocrinol Metab.* 86(11):5176-83) concluded that overlap existed in IGF-1 concentrations in the generation test results between cohorts with primary IGFD (GHI) and secondary IGFD (GHD). The data were re-analyzed after first calculating the amount of IGF-1 generated (in micrograms/kg/hr) at baseline and after GH stimulation Methods: Twenty-three subjects with classic GHD, 22 subjects with GHI homozygous for the E180 splice mutation of the GH receptor, 65 subjects heterozygous for the mutation, and 72 normal subjects were given, in random order, an IGF-1 generation test with low dose (25 μg/kg/d) and high dose (50 μg/kg/d) rhGH for seven days. Blood samples were taken on day 5 and 8 after starting rhGH and blood concentration of IGF-1 and IGFBP-3 were measured. Receiver operating characteristic (ROC) analyses were used to assess the sensitivity and specificity of IGF-1 generation scores to discriminate GHD from the GH resistant patient groups.

Results: The ROC analysis, as performed above for the IGF-1 SDS scores, showed complete discrimination of primary IGFD patients compared to heterozygotes and normals at day 8 after the high dose for all basal and rhGH-stimulated.

Conclusions: In IGFD children with short stature, the ROC analyses show near perfect discrimination between rhGH non-responsive patients with primary IGFD, and rhGH-responsive patients with secondary IGFD. The "IGF-1 SDS generation test" is a useful tool in determining those patients who should benefit from rhGH therapy, versus those who are unlikely to benefit from rhGH and for whom alternative therapies such as rhIGF-1 should be considered.

Example 6

Algorithm for Defining Standard Deviation Score

The determined SDS value for a given individual is useful for determining whether the IGF-1 blood concentration for the individual, with respect to age, is within the normal range, or outside of the normal range. The SDS for the individual is calculated using the following formula:

$$SDS_{age} = (x^p - \text{mean}_{age}) \div SD_{age}.$$

wherein x was blood concentration of IGF-1, p was the power transformation, and $SD_{age}$ was a value obtained from a smooth mean curve generated by plotting IGF-1 blood concentration values as a function of age. In general, it was assumed that the mean used in defining the SD scores for a given variable, such as the concentration of an analyte (e.g., IGF-1) is dependant on another independent variable, such as age, in a non-linear and possibly non-monotonic manner. In addition, it was also assumed that the statistical distribution of the values of the variable, such as IGF-1 concentration) for any given value of the independent variable is not necessarily normal and that a data transformation is necessary before establishing an appropriate mean and SD score.

An initial SAS macro was developed that was defined in terms of IGF-1 concentration and age for a given gender (see Appendix A). The SAS macro began by reading data files containing IGF-1 blood concentration and age for normal male and female subjects. The initial SAS macro with respect to data for male subject was invoked using the following SAS program:

* malesp40.sas;
%inc "_init.sas";
%newsds (sm=0.3, pow=0.40, pw=p40, sex=Males, sexa=M, sexb=1, sexc=males, minage=0.12, maxage=97);

The initial SAS macro with respect to data for female subject was invoked using the following SAS program:

* femalp40.sas;
%inc "_init.sas";
%newsds (sm=0.25, pow=0.40, pw=p40, sex=Females, sexa=F, sexb=2, sexc=femal, minage=0.0358, maxage=95.57);

Based on the data, the initial SAS macro determined an appropriate data transformation power, fit the mean to the transformed data as a function of age, and fit the standard deviation as a function of age. The text output from execution of the SAS program for males is provided in Appendix B and for females is provided in Appendix C. The SAS technical log output from execution of the SAS macro for males is provided in Appendix D and for females is provided in Appendix E.

Figure 12A:
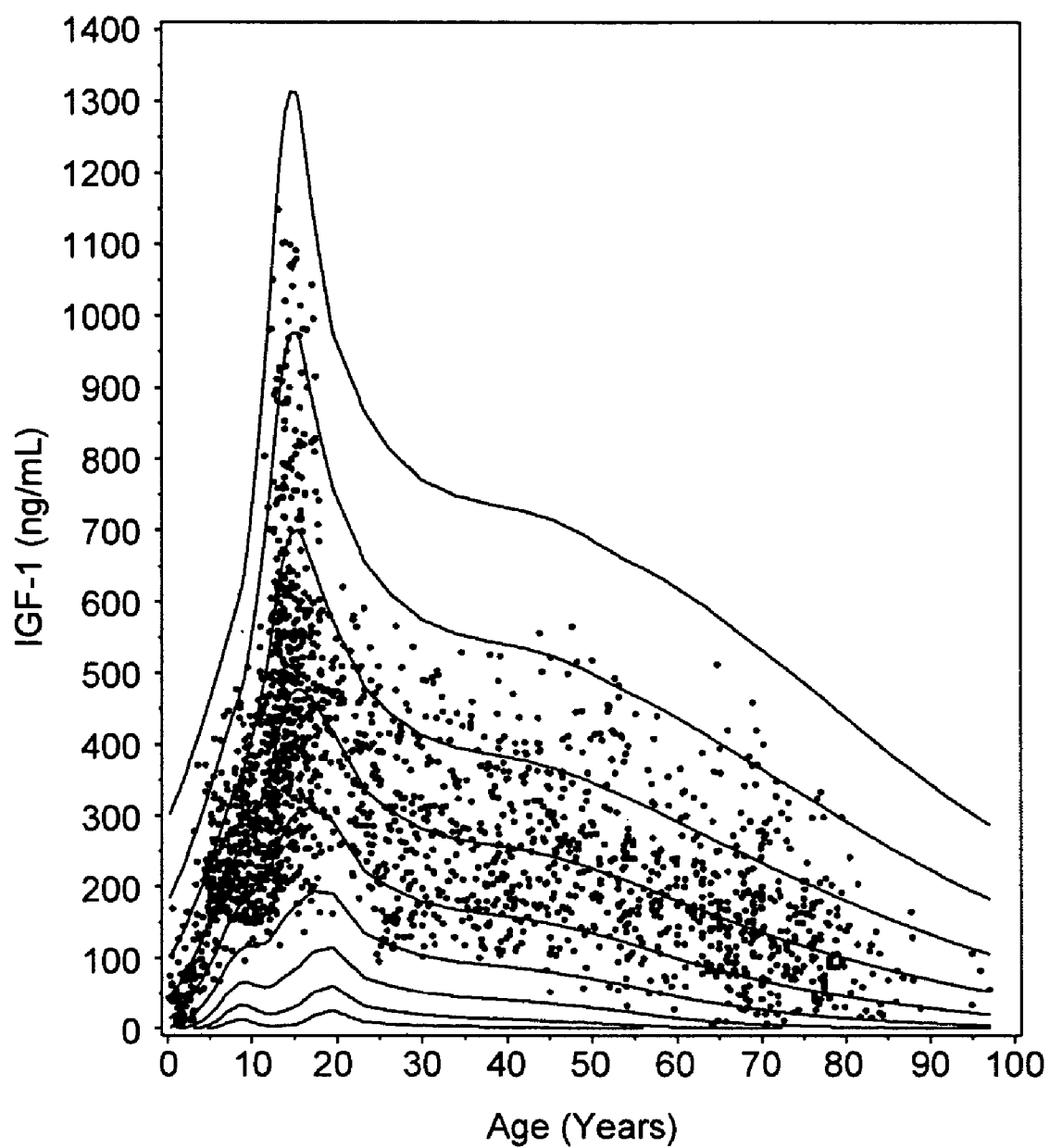
FIG. 12A is a graph of exemplary normative data from a single laboratory for males with IGF-1 blood concentration for SD score levels from −5 to +3.
Figure 12B:
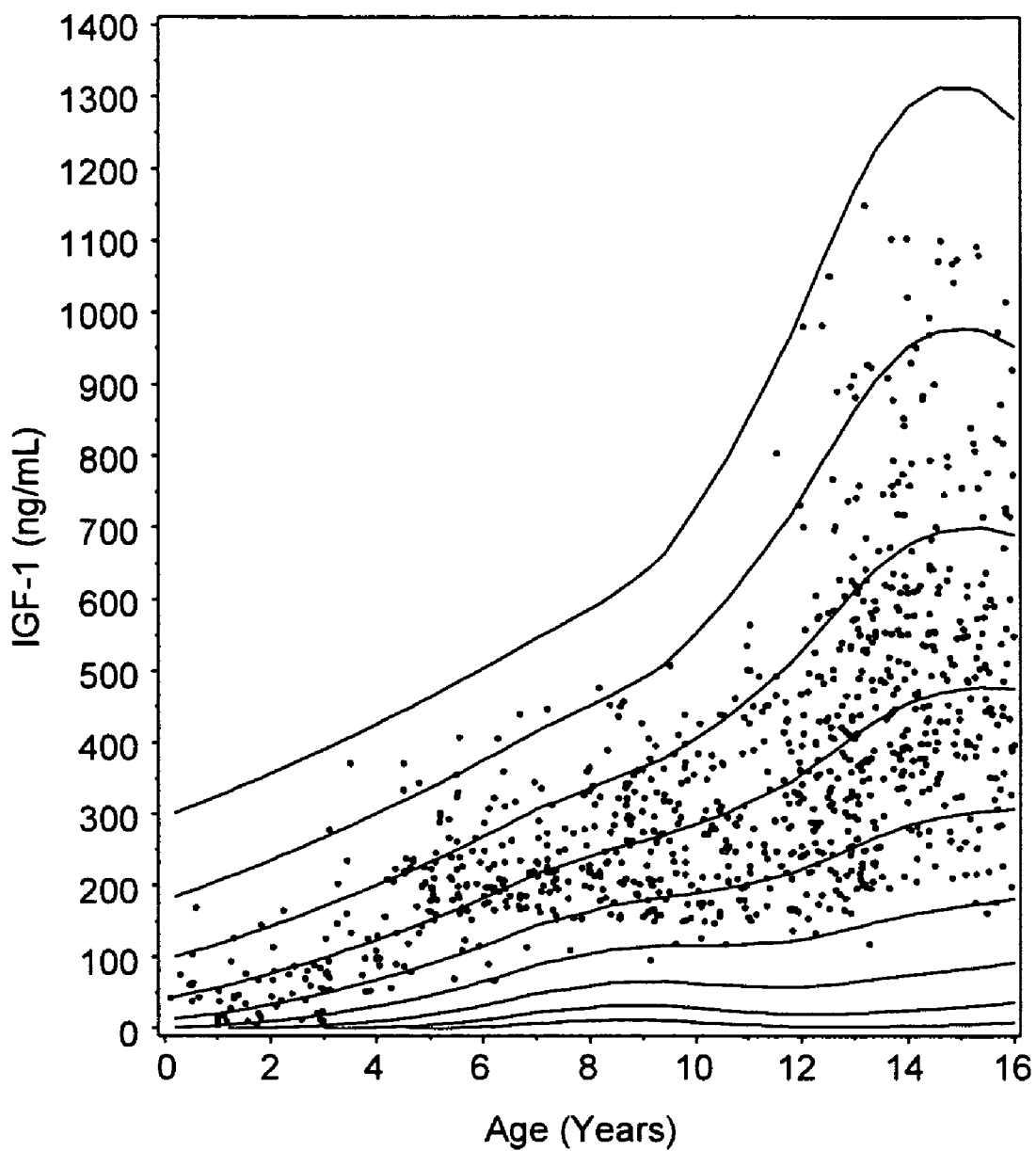
FIG. 12B is a graph of exemplary normative data from a single laboratory for males ages 0 to 16 with IGF-1 blood concentration for SD score levels from −5 to +3.
Figure 12C:
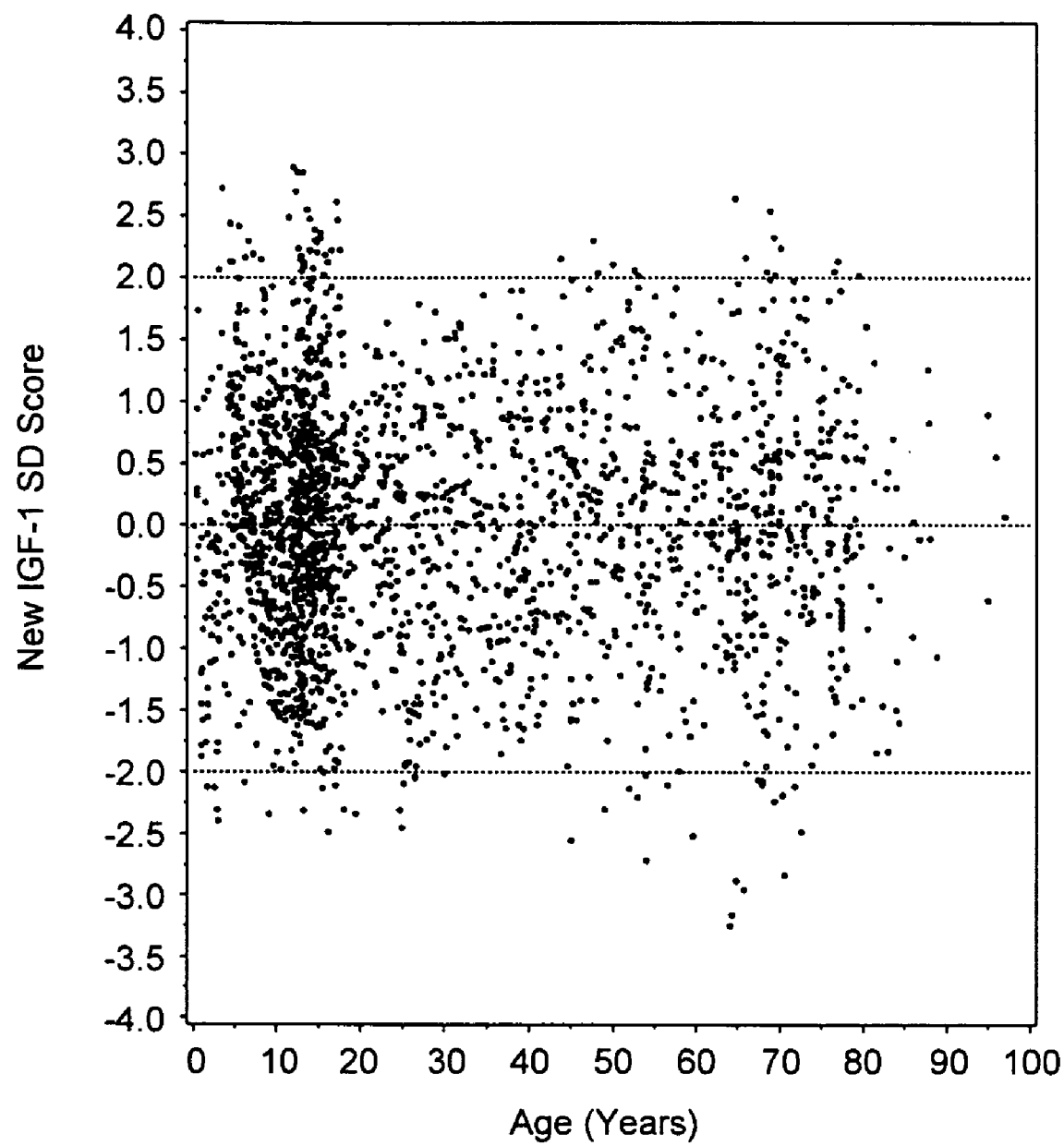
FIG. 12C depicts the IGF-1 SD score for the normative data from a single laboratory for males.

The data output file from the SAS macro for males with respect to age, mean, and SDage on the transformed scale is provided in Appendix F. Graphical output of normative data of IGF-1 blood concentration for males with an SD score levels from −5 to +3 is provided in FIG. 12A. FIG. 12B shows a graph of normative data of IGF-1 blood concentration for males ages 0 to 16 with SD score levels from −5 to +3. FIG. 12C shows the IGF-1 SD score for the normative data for males.

Figure 13A:
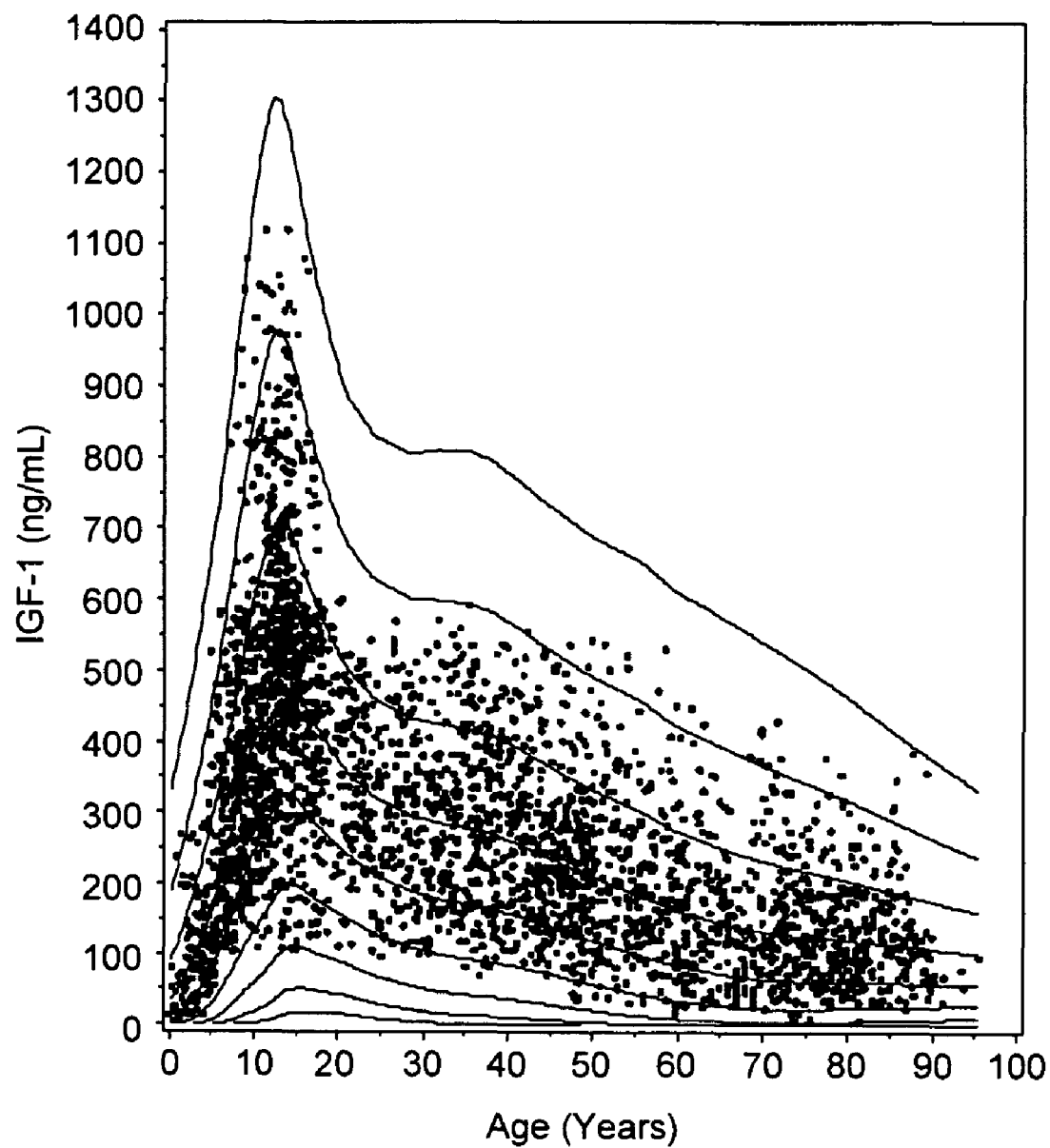
FIG. 13A is a graph of exemplary normative data from a single laboratory for females with IGF-1 blood concentration for SD score levels from −5 to +3.
Figure 13B:
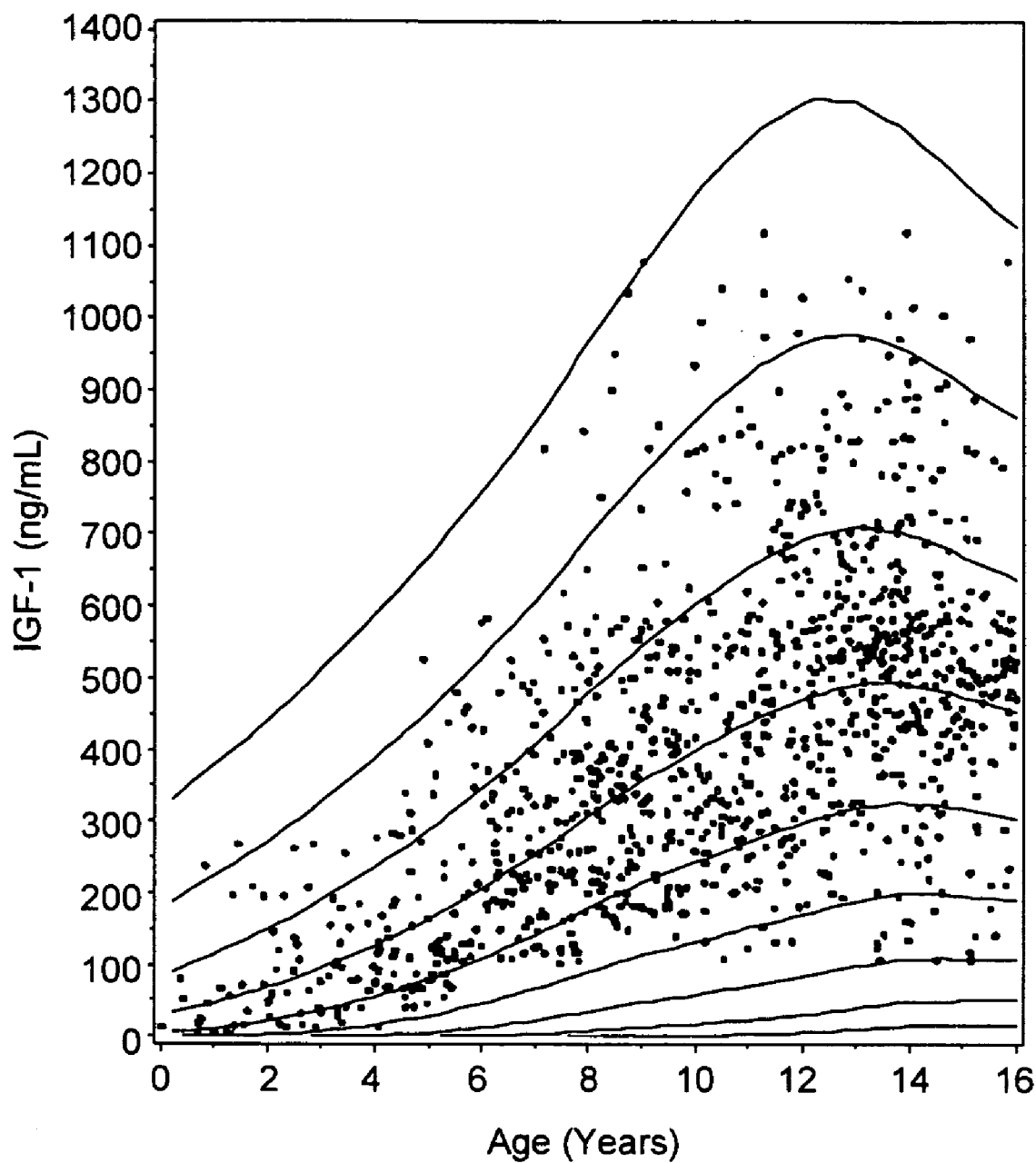
FIG. 13B is a graph of exemplary normative data from a single laboratory for females ages 0 to 16 with IGF-1 blood concentration for SD score levels from −5 to +3.
Figure 13C:
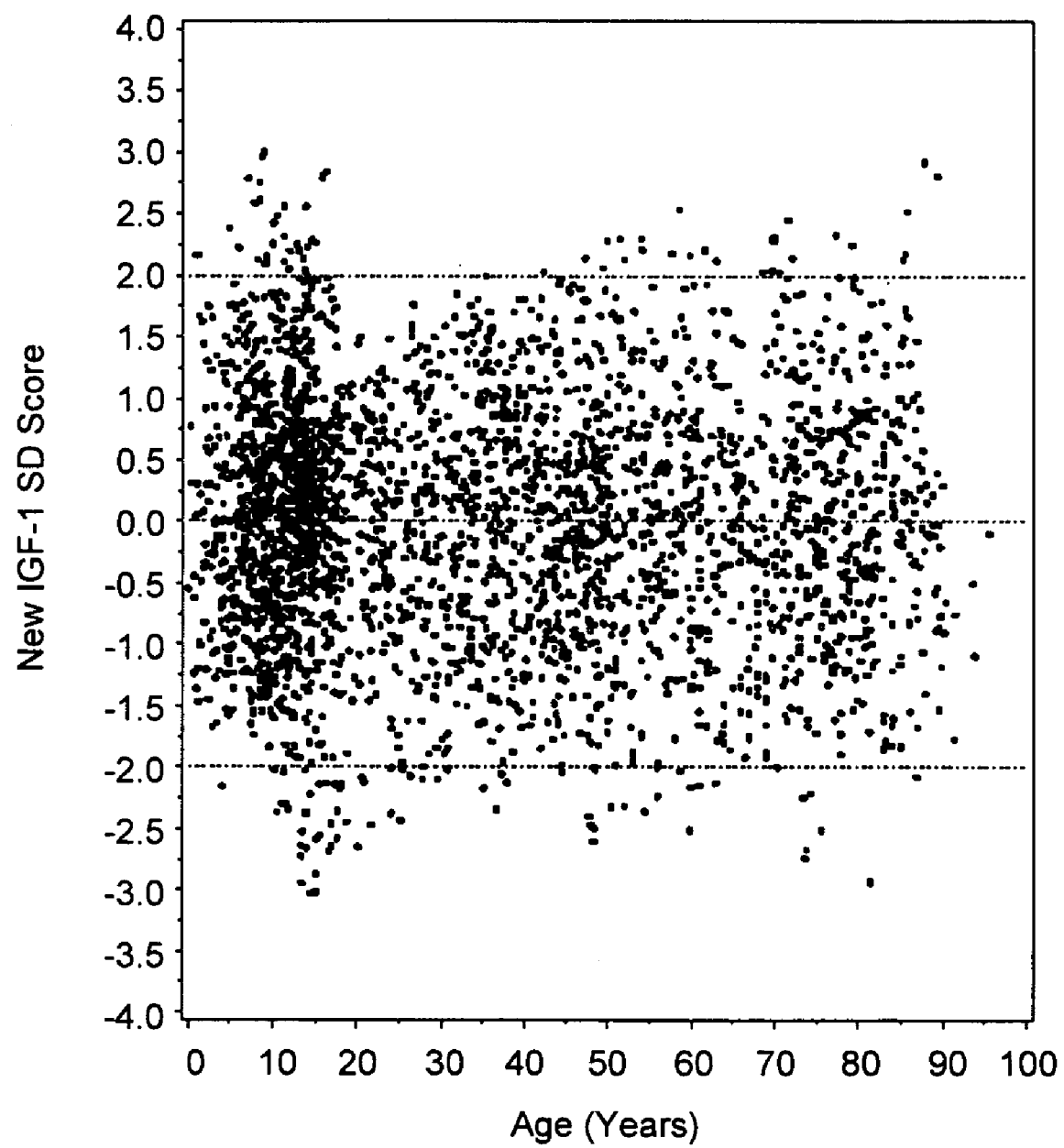
FIG. 13C depicts the IGF-1 SD score for the exemplary normative data from a single laboratory for females.

The data output file from the SAS macro for females with respect to age, mean, and SDage on the transformed scale is provided in Appendix F. Graphical output of normative data of IGF-1 blood concentration for females with an SD score levels from −5 to +3 is provided in FIG. 13A. FIG. 13B shows a graph of normative data of IGF-1 blood concentration for females ages 0 to 16 with SD score levels from −5 to +3. FIG. 13C shows the IGF-1 SD score for the normative data for females.

Based on the normative data for males and females, a patient SDS macro was developed for computing SD scores for patients. The patient SDS macro is provided in Exhibit H. The patient SDS macro was developed to read the mean and standard deviation file for a particular gender that are used to define the SD score on the transformed scale (Appendix F for males and Appendix G for females). The patient SDS macro was programmed to compute the SD score of a patient based on the particular data output file and the data file with respect to the IGF-1 concentration, age, and gender for the particular patient.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating an insulin-like growth factor-1 deficiency (IGFD) disorder in an individual, the method comprising:
   a) calculating an insulin-like growth factor-1 (IGF-1) clearance rate using an IGF-1 binding protein-3 (IGFBP3) concentration measured in a blood, plasma, or serum sample from the individual;
   b) determining an IGF-1 production rate, wherein the IGF-1 production rate is calculated using a computer program that, when read by a computer, executes calculation of an IGF-1 production rate, wherein the IGF-1 production rate is calculated using the algorithm:

$$\text{IGF-1}_{production\ rate} = (\text{IGF-1}_{blood\ conc.})(\text{clearance rate of IGF-1}),$$

wherein said $\text{IGF-1}_{blood\ conc}$ is an IGF-1 concentration measured in a blood, plasma, or serum sample from the individual; and
   c) administering to the individual, based on the determined IGF-1 production rate, an effective amount of IGF 1 or growth hormone (GH), or an effective amount of a combination of GH and IGF-1, said administering being effective to treat IGFD in the individual.

2. The method of claim 1, further comprises transforming the IGF-1 production rate to an IGF-1 production rate standard deviation score (IGF-1 PR SDS); wherein the IGF-1 PR SDS is calculated using the algorithm $$\text{IGF-1 PR SDS} = (x^p - \text{mean}_{age}) \div SD_{age},$$

wherein x is the IGF-1 production rate in blood, wherein the standard deviation score is an IGF-1 production rate standard deviation score (IGF-1 PR SDS), which IGF-1 PR SDS is based on an IGF-1 production rate calculated from the IGF-1 blood concentration in the biological sample from the individual.

3. The method of claim 1, wherein said administering comprises administering to the individual a combination of GH and IGF-1.

4. The method of claim 1, wherein the IGFD disorder is short stature.

5. The method of claim 1, wherein the IGFD disorder is a metabolic disorder.

6. The method of claim 1, wherein said IGF-1 production rate in blood is adjusted for a blood concentration of insulin-like growth factor-2 (IGF-2).

7. The method of claim 2, wherein said determining step further comprises:
   i) determining an IGF-1 production rate in blood at baseline to provide a first IGF-1 PR SDS,
   ii) computing IGF-1 production rate in response to growth hormone (GH) administration to provide a second IGF-1 PR SDS; and
   iii) computing a change in IGF-1 PR SDS between said first and second IGF-1 PR SDS.

8. The method of claim 1, wherein the IGF-1 is recombinant human IGF-1.

9. The method of claim 1, wherein the GH is recombinant human GH.

* * * * *